(12) United States Patent
Zhang et al.

(10) Patent No.: US 10,358,451 B2
(45) Date of Patent: Jul. 23, 2019

(54) HETEROCYCLES USEFUL AS IDO AND TDO INHIBITORS

(71) Applicant: Hangzhou Innogate Pharma Co., Ltd., Hangzhou, Zhejiang (CN)

(72) Inventors: Hancheng Zhang, Zhejiang (CN); Shifeng Liu, Zhejiang (CN)

(73) Assignee: Hangzhou Innogate Pharma Co., Ltd., Zhejiang (CN)

( * ) Notice: Subject to any disclaimer, the term of this patent is extended or adjusted under 35 U.S.C. 154(b) by 0 days.

(21) Appl. No.: 15/566,052

(22) PCT Filed: Apr. 12, 2016

(86) PCT No.: PCT/CN2016/079104
§ 371 (c)(1),
(2) Date: Oct. 12, 2017

(87) PCT Pub. No.: WO2016/165613
PCT Pub. Date: Oct. 20, 2016

(65) Prior Publication Data
US 2018/0127418 A1    May 10, 2018

Related U.S. Application Data

(60) Provisional application No. 62/274,292, filed on Jan. 2, 2016, provisional application No. 62/146,340, filed on Apr. 12, 2015.

(51) Int. Cl.
| | |
|---|---|
| *A61K 31/4188* | (2006.01) |
| *C07D 487/04* | (2006.01) |
| *A61P 37/00* | (2006.01) |
| *A61P 31/18* | (2006.01) |
| *A61P 35/00* | (2006.01) |

(52) U.S. Cl.
CPC ............ *C07D 487/04* (2013.01); *A61P 31/18* (2018.01); *A61P 35/00* (2018.01); *A61P 37/00* (2018.01)

(58) Field of Classification Search
CPC .................... A61K 31/4188; C07D 487/04
USPC ........ 544/115; 546/199; 548/302.4; 514/393, 514/230.8, 322
See application file for complete search history.

(56) References Cited

FOREIGN PATENT DOCUMENTS

| | | |
|---|---|---|
| CN | 105037371 A | 11/2015 |
| WO | 2012142237 A1 | 10/2012 |
| WO | 2014159248 A1 | 10/2014 |
| WO | 2016037026 A1 | 3/2016 |
| WO | 2016051181 A1 | 4/2016 |

OTHER PUBLICATIONS

Int'l Search Report dated Jul. 13, 2016 in Int'l Application No. PCT/CN2016/079104.
Int'l Preliminary Report on Patentability dated Oct. 26, 2017 in Int'l Application No. PCT/CN2016/079104.

*Primary Examiner* — Jeffrey H Murray
(74) *Attorney, Agent, or Firm* — Panitch Schwarze Belisario & Nadel LLP

(57) ABSTRACT

Provided are compounds of Formula (I) shown below using for treatment of diseases or disorders mediated by IDO and/or TDO, pharmaceutical compositions and methods of preparation thereof.

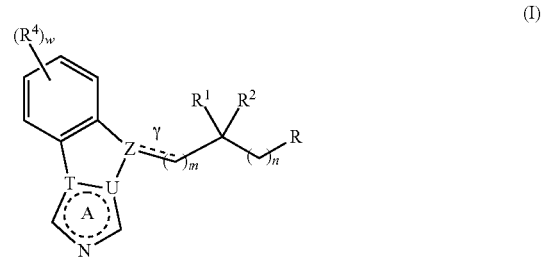

26 Claims, No Drawings

HETEROCYCLES USEFUL AS IDO AND TDO INHIBITORS

CROSS-REFERENCE TO RELATED APPLICATIONS

This application is a Section 371 of International Application No. PCT/CN2016/079104, filed Apr. 12, 2016, which was published in the English language on Oct. 20, 2016, under International Publication No. WO 2016/165613 A1, which claims priority to and benefit of U.S. Provisional Application No. 62/274,292, filed Jan. 2, 2016, and U.S. Provisional Application No. 62/146,340, file Apr. 12, 2015, and the disclosures of which are incorporated herein by reference.

FIELD OF THE INVENTION

The present invention provides, among others, novel heterocyclic compounds, their synthesis, and their uses, e.g., as inhibitors for IDO (indoleamine 2,3-dioxygenase) and/or TDO (tryptophan 2,3-dioxygenase).

BACKGROUND OF THE INVENTION

IDO (indoleamine 2,3-dioxygenase) and/or TDO (tryptophan 2,3-dioxygenase) are heme-containing oxidoreductase enzymes which catalyze the initial and rate limiting step in the degradation of essential amino acid L-tryptophan to N-Formyl kenurenine. TDO is mainly expressed in liver tissue, and is responsible for regulating systemic tryptophan levels. IDO comprises two related enzymes IDO isozymes (IDO1, IDO2), and is widely expressed in numerous cells, such as neurons, astrocytes, microglia, especially antigen-presenting cells (macrophages and dendritic cells) at high level. IDO is also overexpressed in many different types of human tumor, facilitating the escape of malignant tumors from immune surveillance and promoting tumor growth. Three immunosuppressive mechanisms have been proposed for IDO-kenurenine pathway: 1. depletion of tryptophan directly inhibits activation and proliferation of effector T cells; 2. accumulation of toxic kynurenine, binding of kynurenine to the aryl hydrocarbon receptor enhance immune tolerance; 3. the induction of $T_{Reg}$ cell. Tryptophan metabolism is critical for cell proliferation, inflammation and immunoregulation. Accelerated tryptophan breakdown favors tumor immune escape. Therefore IDO may represent an attractive therapeutic target in cancer immunotherapy.

There is also growing evidence that IDO inhibitors have potential therapeutic application in many other diseases, such as for treatment of infectious disease, inflammation, cataracts, endometriosis, pain, atherosclerosis, neurological or neuropsychiatric conditions such as depression, amyotrophic lateral sclerosis, Huntingdon's disease, Alzheimer's disease, multiple sclerosis, Parkinson's disease, etc.

Small molecule IDO inhibitors are being developed to treat the diseases mediated by IDO enzyme, and could be administered alone or in combination with chemotherapy or immunotherapy (PD-1, CTLA-4, PD-L1, etc.).

SUMMARY OF THE INVENTION

The present invention provides, among others, novel heterocyclic compounds and their uses, e.g., as inhibitors for IDO (indoleamine 2,3-dioxygenase) and/or TDO (tryptophan 2,3-dioxygenase).

In one aspect, the present invention provides a compound of Formula (I) or a pharmaceutically acceptable salt, prodrug, deuterated derivative, hydrate, or solvate thereof:

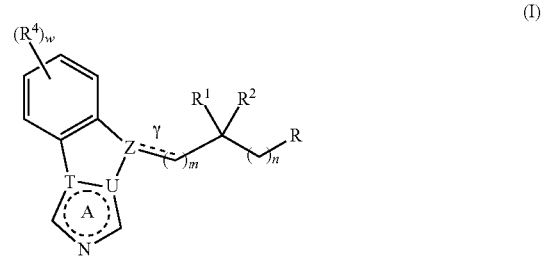

(I)

in Formula (I):

Ring A is a 5-membered aromatic ring, wherein each of T and U independently is N or C;

Z is $CR^3$ or N when bond γ is a single bond; or Z is C when bond γ is a double bond;

each of $R^1$ and $R^2$, independently, is hydrogen, halogen, $C_{1-4}$ alkyl, $C_{2-4}$ alkenyl, $C_{2-4}$ alkynyl, cycloalkyl, $C_{1-4}$ haloalkyl, heterocyclyl, CN, $OR^5$, or $N(R^5)_2$;

or, $R^1$ and $R^2$, together with the carbon atom to which they are attached, form a 3- to 8-membered ring that contains 0-2 heteroatoms each independently being N, O, or S;

w is 0, 1, 2, 3, or 4;

each of m and n independently is 0, 1, 2, 3, or 4;

$R^3$ is hydrogen, fluorine, or $C_{1-4}$ alkyl;

each of $R^4$ is hydrogen, halogen, $C_{1-4}$ alkyl, $C_{2-4}$ alkenyl, $C_{2-4}$ alkynyl, cycloalkyl, $C_{1-4}$ haloalkyl, heterocyclyl, aryl, heteroaryl, CN, $NO_2$, $OR^5$, $N(R^5)_2$, $SR^5$, $C(O)OR^5$, $C(O)N(R^5)_2$, $C(O)R^5$, $S(O)_2R^5$, $S(O)_2N(R^5)_2$, $OC(O)R^5$, $OC(O)OR^5$, $OC(O)N(R^5)_2$, $N(R^5)C(O)R^5$, or $N(R^5)C(O)N(R^5)_2$;

Each $R^5$ independently is hydrogen, $C_{1-4}$ alkyl, cycloalkyl, heterocyclyl, aryl, or heteroaryl;

R is hydrogen, halogen, $C_{1-8}$ alkyl, $C_{2-8}$ alkenyl, $C_{2-8}$ alkynyl, cycloalkyl, heterocyclyl, aryl, heteroaryl, $OR^A$, $C(O)R^A$, $C(OR^B)(R^A)(R^C)$, $C(NHR^B)(R^A)(R^C)$, $C(=N-OR^C)R^A$, or $N(OR^C)(R^A)$, wherein $R^A$ is hydrogen, $C_{1-8}$ alkyl, $C_{2-8}$ alkenyl, $C_{2-8}$ alkynyl, aryl, heteroaryl, cycloalkyl, cycloalkenyl, heterocyclyl, aryl-heterocyclyl, heteroaryl-heterocyclyl, cycloalkyl-heterocyclyl, heterocyclyl-heterocyclyl, or heterocyclyl-aryl, each optionally substituted, wherein, the $C_{1-8}$ alkyl, $C_{2-8}$ alkenyl, $C_{2-8}$ alkynyl, cycloalkyl, cycloalkenyl, heterocyclyl, aryl-heterocyclyl, heteroaryl-heterocyclyl, cycloalkyl-heterocyclyl, heterocyclyl-heterocyclyl, or heterocyclyl-aryl are each optionally substituted by one or two $=R^{42}$ groups and each optionally substituted by one to three $R^{41}$ groups;

the aryl and heteroaryl are each optionally substituted by one to three $R^{41}$ groups;

wherein each $R^{41}$ is independently hydrogen, halogen, $C_{1-4}$ alkyl, $C_{2-4}$ alkenyl, $C_{2-4}$ alkynyl, $C_{1-4}$ haloalkyl, aryl, heteroaryl, cycloalkyl, cycloalkenyl, heterocyclyl, CN, $NO_2$, N-oxide, $OR^5$, $N(R^5)_2$, $SR^5$, $C(O)OR^5$, $C(O)N(R^5)_2$, $C(O)N(OH)R^5$, $C(O)R^5$, $C(NR^6)R^5$, $C(NR^6)N(R^6)R^5$, $S(O)R^5$, $S(O)OR^5$, $S(O)_2R^5$, $S(O)_2N(R^5)_2$, $OC(O)R^5$, $OC(O)OR^5$, $OC(O)N(R^5)_2$, $N(R^5)C(O)R^5$, $N(R^5)C(O)OR^5$, or $N(R^5)C(O)N(R^5)_2$;

=$R^{A2}$ is =O, =S, =N($R^5$), =N(O$R^5$), =C($R^{A3}$)$_2$, =(spiro-cycloalkyl), or =(spiro-heterocyclyl), wherein, each $R^{A3}$ is independently hydrogen, halogen, CN, $C_{1-4}$ alkyl, cycloalkyl, or heterocyclyl; or both $R^{A3}$ taken together with the atom to which they are both attached form a monocyclic cycloalkyl or monocyclic heterocyclyl;

$R^B$ is hydrogen, $C_{1-4}$ alkyl, C(O)$R^A$, C(O)N(H)$R^A$, C(O)(CH$_2$)$_{1-4}$COO$R^5$, C(O)(CH$_2$)$_{1-4}$(N$R^5$)COO$R^5$, C(O)CH(NH$_2$)$R^A$, CH$_2$—OP(O)$_2$(O$R^5$)$_2$, or P(O)(O$R^A$)$_2$;

$R^C$ is hydrogen or $C_{1-4}$ alkyl;

each $R^6$ is independently hydrogen or $C_{1-4}$ alkyl;

each of alkyl, alkenyl, alkynyl, cycloalkyl, heterocyclyl, aryl, and heteroaryl described above is optionally substituted with one to three substituents independently selected from the group consisting of halogen, $C_{1-4}$ alkyl, $C_{2-4}$ alkenyl, $C_{2-4}$ alkynyl, cycloalkyl, heterocyclyl, aryl, heteroaryl, CN, NO$_2$, O$R^5$, S$R^5$, N($R^5$)$_2$, C(O)$R^5$, C(O)O$R^5$, C(O)N($R^5$)$_2$, and S(O)$_2$$R^5$;

with the proviso that when T and U independently is N or C, $R^1$ is H, $R^2$ is H, Z is CH, γ is a single bond, m is 0, 1, 2 or 3, n is 0, 1, 2, or 3, then R is C(O$R^B$)($R^A$)($R^C$) and $R^A$ is a bridged $C_7$-$C_{16}$ cycloalkyl, aryl-heterocyclyl, cycloalkyl-heterocyclyl, heterocyclyl-heterocyclyl, or heterocyclyl-aryl.

In one preferred embodiment, bond γ is a single bond.

In one preferred embodiment, T and U independently is N or C, and Z is C$R^3$ or N.

In one preferred embodiment, Formula (II)

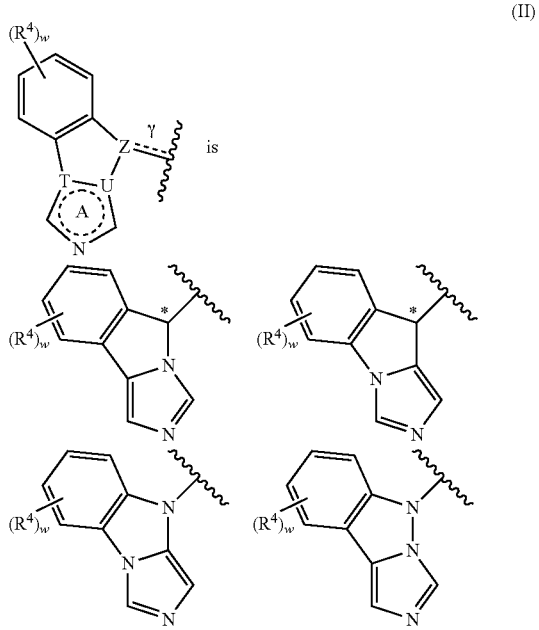

wherein:
each $R^4$ at each occurrence is independently halogen, $C_{1-4}$ alkyl, $C_{1-4}$ haloalkyl, CN, NO$_2$, O$R^5$, N($R^5$)$_2$, S$R^5$ define as above;
w is 0, 1, or 2
"⁓" indicates the point of attachment in Formula (II) to the rest of molecules in Formula (I);
"*" denotes a chiral center.

In one preferred embodiment, T is C, U is N, and Z is CH.

In one preferred embodiment, $R^1$ and $R^2$, together with the carbon atom to which they are attached, form a 3 to 8-membered ring that contains 0-1 heteroatom being N or O.

In one preferred embodiment, $R^1$ and $R^2$, together with the carbon atom to which they are attached, form a $C_{3-6}$ cycloalkyl In one preferred embodiment, each $R^1$ and $R^2$ is independently H or F.

In one preferred embodiment, both $R^1$ and $R^2$ are H or F.

In one preferred embodiment, each of m and n independently is 0 or 1.

In one preferred embodiment, R is cycloalkyl, heterocyclyl, aryl, heteroaryl, O$R^A$, C(O$R^B$)($R^A$)($R^C$), or N(O$R$)($R^A$).

In one preferred embodiment, R is C(O$R^B$)($R^A$)($R^C$).

In one preferred embodiment, R is C(OH)($R^A$)($R^C$).

In one preferred embodiment, R is CH(OH)($R^A$).

In one preferred embodiment, $R^A$ is aryl-heterocyclyl, cycloalkyl-heterocyclyl, heterocyclyl-heterocyclyl, or heterocyclyl-aryl.

In one preferred embodiment, $R^A$ is $C_{6-10}$ aryl-(5-8-membered heterocyclyl), $C_{3-6}$ cycloalkyl-(5-8-membered heterocyclyl), (5-8-membered heterocyclyl)-(5-8-membered heterocyclyl), or (5-8-membered heterocyclyl)-$C_{6-10}$ aryl.

In one preferred embodiment, the 5-8-membered heterocyclyl contains 1 or 2 nitrogen atoms and optionally 1 oxygen atom (preferably 1 nitrogen atom and no oxygen atom), and the rest ring atoms are C.

In one preferred embodiment, the two moieties in aryl-heterocyclyl, cycloalkyl-heterocyclyl, heterocyclyl-heterocyclyl, and heterocyclyl-aryl are linked through an N—C bond.

In one preferred embodiment, $R^A$ is bridged $C_7$-$C_{16}$ cycloalkyl, preferably bridged $C_7$-$C_{14}$ cycloalkyl, more preferably bridged $C_8$-$C_{12}$ cycloalkyl.

In one preferred embodiment, $R^A$ is unsubstituted or substituted adamantyl, unsubstituted or substituted bicyclo[2.2.2]octyl; preferably, the term "substituted" means having 1-3 substituents selected from the group consisting of: halogen, $C_{1-4}$ alkyl, —OH, $C_{1-4}$ alkyloxy, $C_{1-4}$ haloalkyl, $C_{3-6}$ cycloalkyl, CN, N($C_{1-4}$ alkyl)$_2$, C(O)O$C_{1-4}$ alkyl, C(O)N($C_{1-4}$alkyl)$_2$, and C(O)$C_{1-4}$ alkyl;

In one preferred embodiment, the heterocyclyl by itself or as part of another substituent is 3-10 membered heterocyclyl which is optionally substituted by one or two =$R^{A2}$ group and optionally substituted by one to three $R^{A1}$ groups.

In one preferred embodiment, aryl and heteroaryl by itself or as part of another substituent are each optionally substituted by one to three $R^{A1}$ groups.

In one preferred embodiment, each $R^{A1}$ is independently hydrogen, halogen, $C_{1-4}$ alkyl, $C_{1-4}$ haloalkyl, $C_{3-6}$ cycloalkyl, CN, NO$_2$, O$R^5$, N($R^5$)$_2$, C(O)O$R^5$, C(O)N($R^5$)$_2$, C(O)N(OH)$R^5$, or C(O)$R^5$.

In one preferred embodiment, each =$R^{A2}$ is =O.

In another preferred embodiment, C(O$R^B$)($R^A$)($R^C$) is

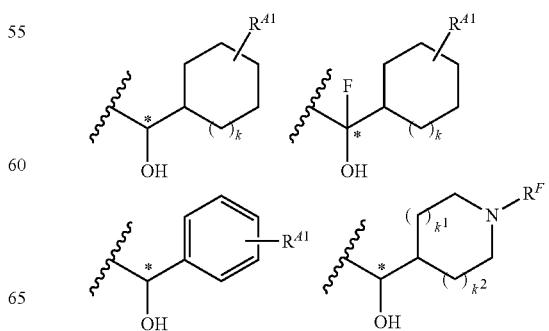

-continued

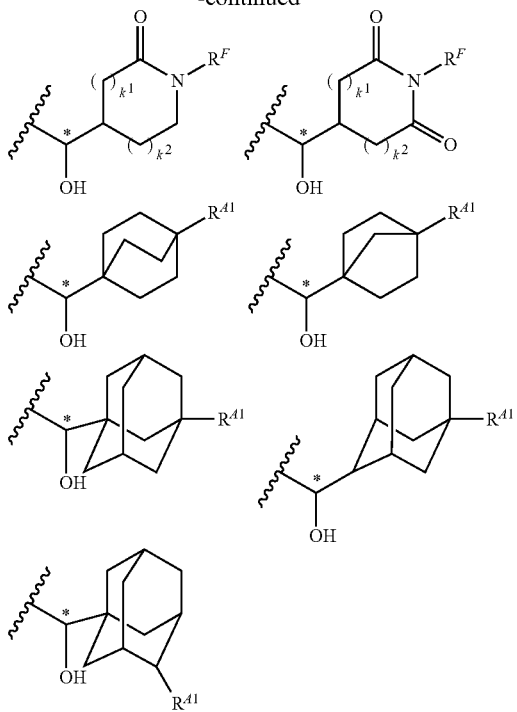

k=0, 1, 2, 3, 4; k¹=0, 1, 2, 3; k²=0, 1, 2, 3.
$R^F$=hydrogen, alkyl,

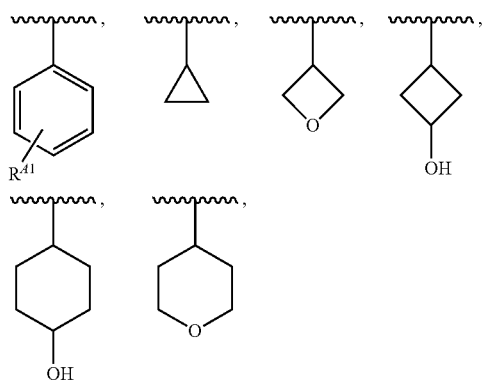

etc.
$R^{A1}$ is defined as above

In one preferred embodiment, the compound is characterized by formula (III):

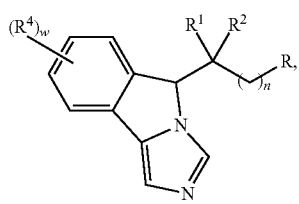

(III)

wherein:
R is $C(OR^B)(R^A)(R^C)$;
n is 0, 1, or 2;

$R^1$ and $R^2$ are each independently hydrogen or halogen;
w is 0, 1, 2, or 3;
$R^4$ at each occurrence is independently halogen, $C_{1-4}$ alkyl, $C_{1-4}$ haloalkyl, CN, $NO_2$, $OR^5$, $N(R^5)_2$, $SR^5$; and
$R^5$ at each occurrence is independently hydrogen or $C_{1-4}$ alkyl.

In one preferred embodiment, the compound wherein n is 0 is further characterized by formula (IV):

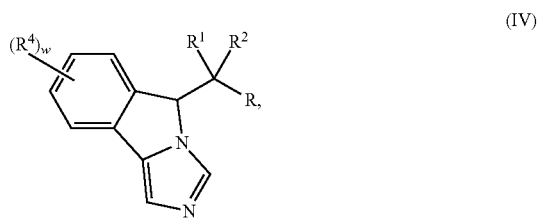

(IV)

wherein R is $C(OR^B)(R^A)(R^C)$ having a structure selected from the group consisting of:

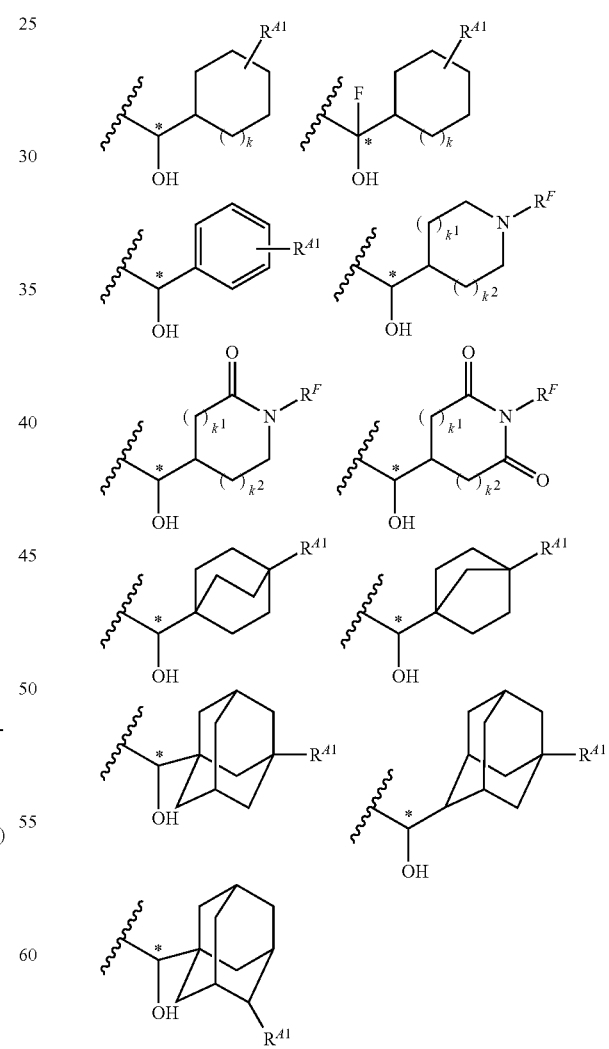

k=0, 1, 2, 3, 4; k¹=0, 1, 2, 3; k²=0, 1, 2, 3.
$R^F$=hydrogen, alkyl,

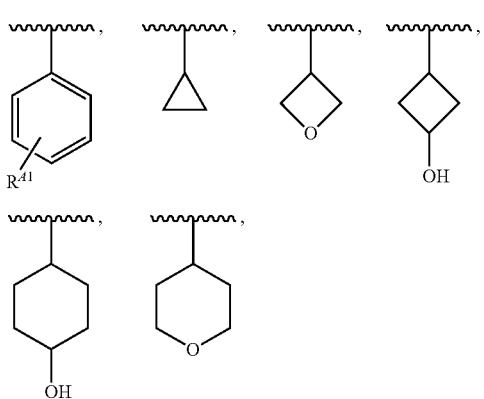

etc.

$R^{A1}$ is defined as above

In one preferred embodiment, the compound, wherein n is 0 and $R^C$ is hydrogen, is further characterized by formula (V):

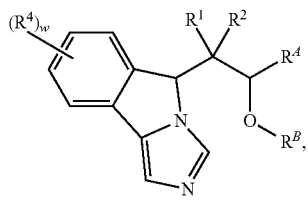

wherein:

$R^4$ is aryl, heteroaryl, cycloalkyl, heterocyclyl, aryl-heterocyclyl, heteroaryl-heterocyclyl, cycloalkyl-heterocyclyl, heterocyclyl-heterocyclyl, or heterocyclyl-aryl, each optionally substituted; and $R^B$ is hydrogen, $C_{1-4}$ alkyl, $C(O)R^{A2}$, or $P(O)(OR^{A2})_2$, wherein $R^{A2}$ is hydrogen or $C_{1-4}$ alkyl.

In one preferred embodiment, $R^4$ is adamantyl, bicyclo[2,2,2]octyl, cyclohexyl, piperidinyl, or phenyl, each optionally substituted; and $R^B$ is hydrogen or $C_{1-4}$ alkyl.

In one preferred embodiment, $R^4$ is selected from the group consisting of:

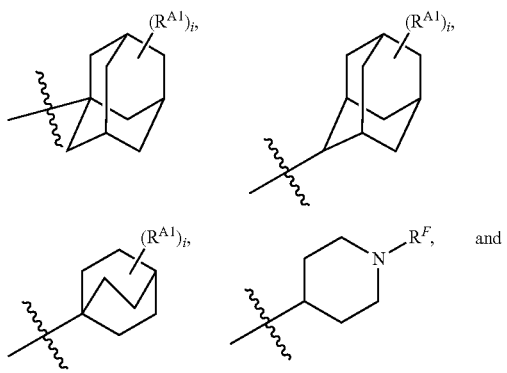

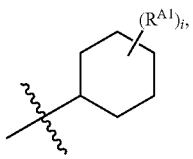

wherein:

each i is independently 0, 1, 2, or 3;

$R^{A1}$ at each occurrence is independently halogen or OH; and $R^F$ is selected from phenyl, $C_3$-$C_6$ cycloalkyl, and 4 to 6-membered heterocyclyl, each optionally substituted.

In one preferred embodiment, w is 0, 1, or 2; $R^4$ is halogen; $R^1$ and $R^2$ are each hydrogen or fluoro; $R^B$ and $R^C$ are each hydrogen; and $R^4$ is selected from the group consisting of:

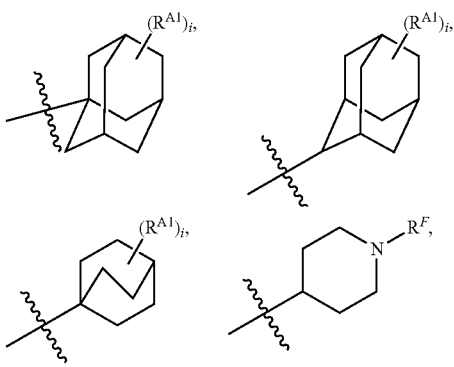

wherein i at each occurrence is 0, 1, or 2; $R^{A1}$ at each occurrence is OH; and $R^F$ is phenyl optionally substituted by one or two substituents selected from $NO_2$ and $CF^3$.

In another preferred embodiment, a compound of Formula (I) is selected from the group consisting of:

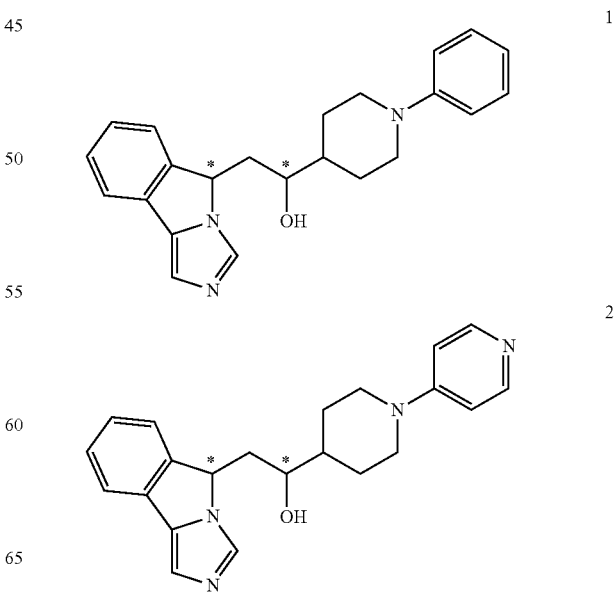

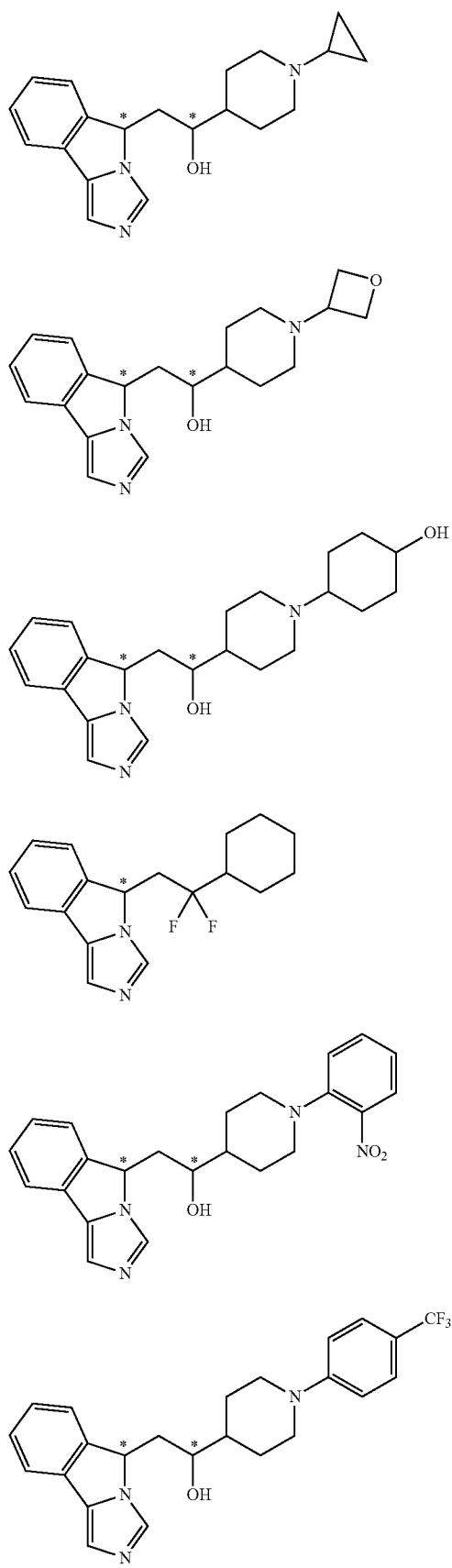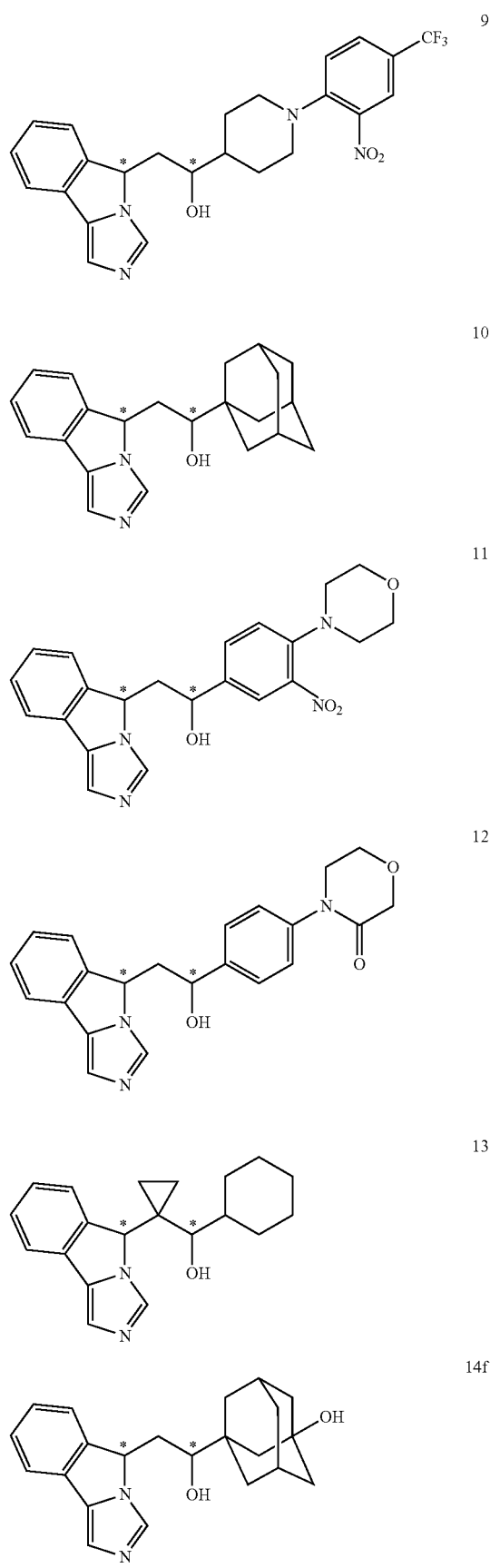

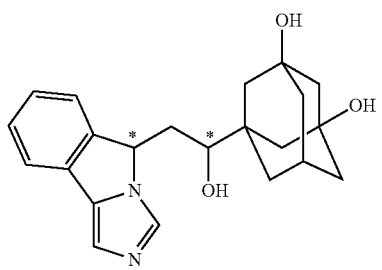
14g
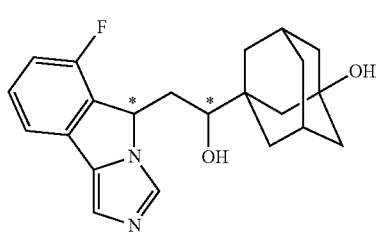
15d
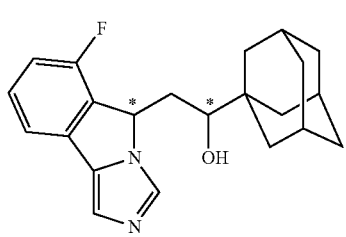
15e
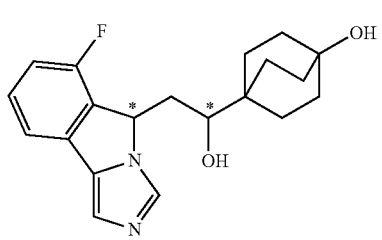
16
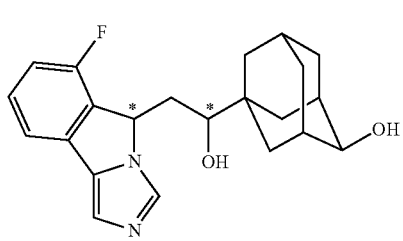
17
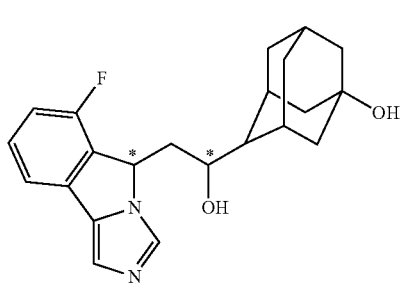
18
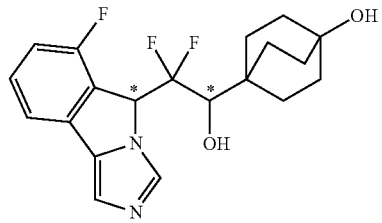
19
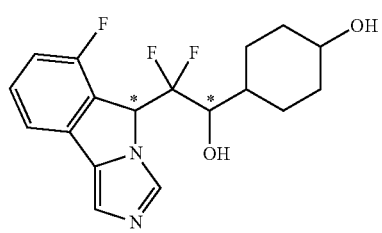
20
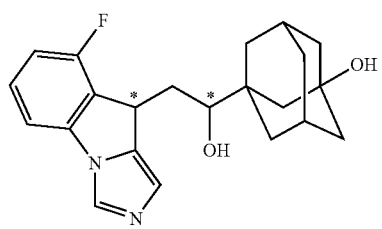
21
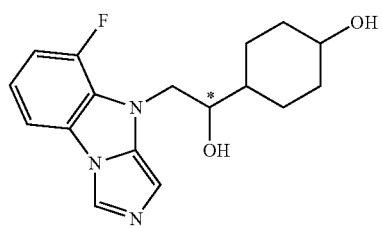
22
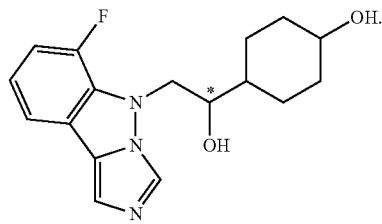
23
In another preferred embodiment, a compound of Formula (I) is
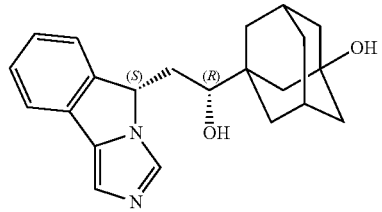
14fRS 14fSS
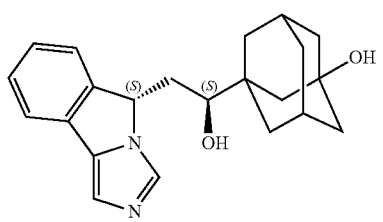
14fSR
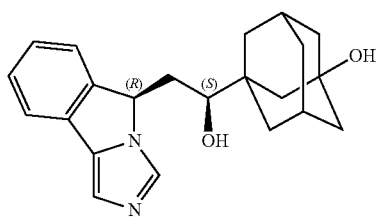
14fRR
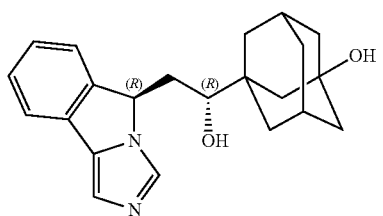
15dRS
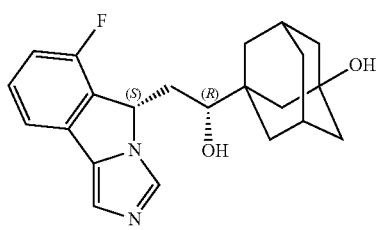
15dSS
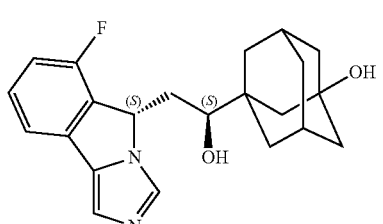
15dSR
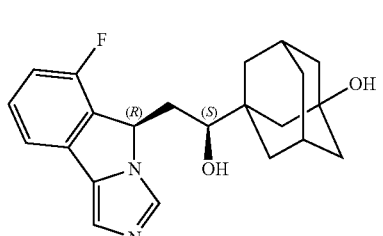
15dRR
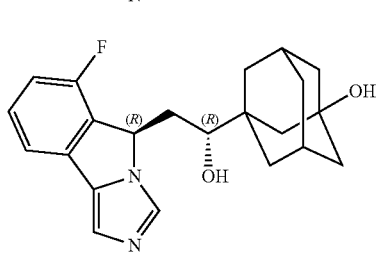
16RS
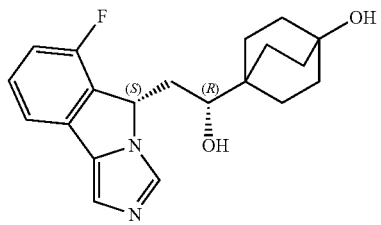
16SS
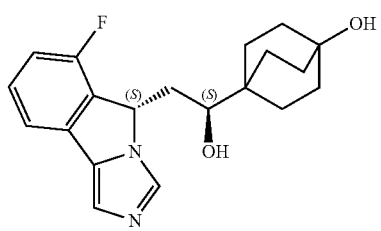
16SR
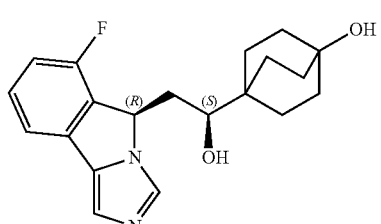
16RR
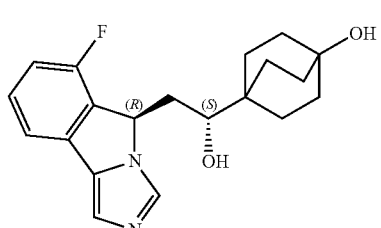
17RS
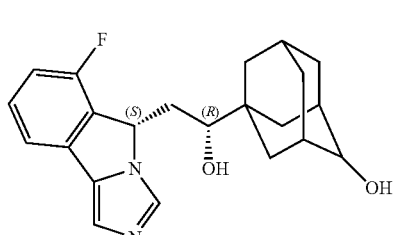
17SS
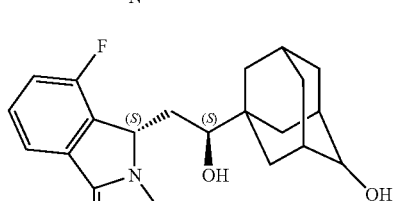
17SR
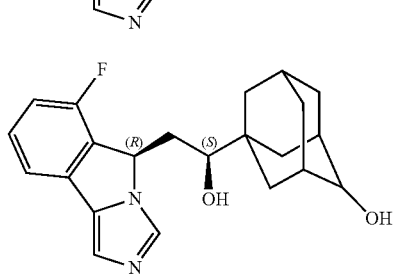

-continued

17RR
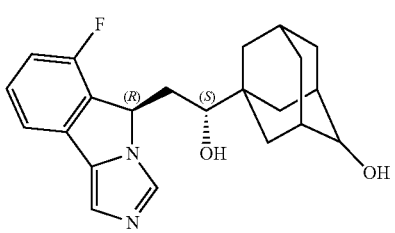

18RS
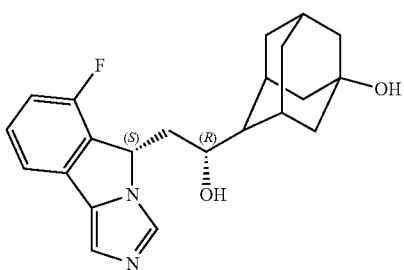

18SS
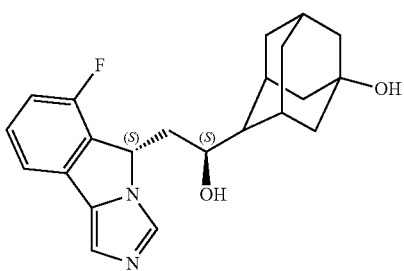

18SR
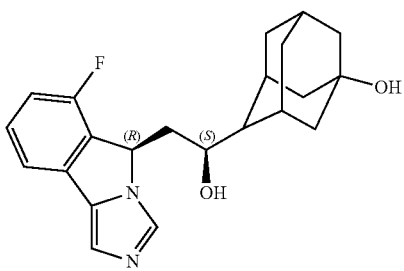

18RR
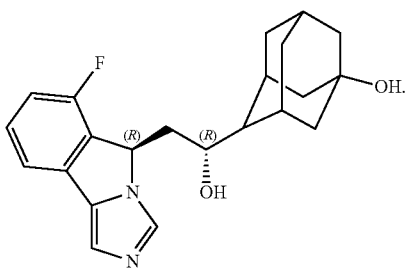

In another preferred embodiment, the pharmaceutically acceptable salt of the compound of the first aspect of the invention is acidic/anionic or basic/cationic salt.

A second aspect of the invention provides a method for preparing a pharmaceutical composition, comprising mixing the compound of the first aspect of the invention, or a crystal form, a pharmaceutically acceptable salt, a hydrate or a solvate thereof and a pharmaceutically acceptable carrier to form a pharmaceutical composition.

A third aspect of the invention provides a pharmaceutical composition, comprising a compound of the invention as described above, or a crystal form, a pharmaceutically acceptable salt, a hydrate or a solvate thereof, and a pharmaceutically acceptable carrier or excipient.

In one embodiment, the composition is injection, capsules, tablets, pills, powder or granules.

In the fourth aspect, the present invention provides a use of the compound of the first aspect of the invention or a crystal form, a pharmaceutically acceptable salt, a hydrate or a solvate thereof as inhibitors of IDO (indoleamine 2,3-dioxygenase) and/or TDO (tryptophan 2,3-dioxygenase) in the manufacture of a medicament for treating medical conditions that benefit from inhibition of IDO and/or TDO.

In one embodiment, IDO is IDO1 and/or IDO2.

In one embodiment, IDO is IDO1.

In one embodiment, the IDO and/or TDO mediated medical conditions includes but is not limited to cancer, infectious disease, inflammation, cataracts, endometriosis, pain, atherosclerosis, neurological or neuropsychiatric conditions.

In one embodiment, neurological or neuropsychiatric conditions are depression, amyotrophic lateral sclerosis, huntingdon's disease, alzheimer's disease, multiple sclerosis, parkinson's disease, etc.

In one embodiment, the infectious disease is a viral infection caused by Heptitis C virus (HCV), human papilloma virus (HPV), human immunodeficiency virus (HIV), cytomegalovirus (CMV).

In one embodiment, the cancer is breast cancer, lymph cancer, leukemia, lung cancer, ovarian cancer, cervix cancer, testis cancer, liver cancer, melanoma, colon cancers, rectal cancer, renal-cell carcinoma, cancer of the small intestine and cancer of the esophagus, head and neck cancer, bladder cancer, prostate cancer, pancreatic cancer or pharynx cancer.

In the fifth aspect, the present invention provides a use of the compound of the first aspect of the invention or a crystal form, a pharmaceutically acceptable salt, a hydrate or a solvate thereof as an inhibitor of IDO (indoleamine 2,3-dioxygenase) and/or TDO (tryptophan 2,3-dioxygenase) in the manufacture of a medicament to stimulate T cell proliferation or reverse an immunologic state of anergy or immunosuppression.

In one embodiment, the anergy or immunosuppression is caused by expression of indoleamine 2,3-dioxygenase.

In one embodiment, the anergy or immunosuppression is caused by expression of tryptophan 2,3-dioxygenase.

In the sixth aspect, the present invention provides a method for treating immunosuppression mediated by an IDO and/or TDO in a subject, comprising administering to the subject in need thereof a therapeutically effective amount of a compound of the first aspect of the invention or a composition of the third aspect of the invention.

In one embodiment, the immunosuppression is associated with an infectious disease, or cancer.

In another embodiment, the immunosuppression is associated with an infectious disease and the infectious disease is a viral infection caused by Heptitis C virus (HCV), human papilloma virus (HPV), human immunodeficiency virus (HIV), cytomegalovirus (CMV).

In another embodiment, the immunosuppression is immunosuppression associated with human immunodeficiency virus (HIV)

In one embodiment, the immunosuppression is associated with a cancer.

In another embodiment, the immunosuppression is tumor specific immunosuppression associated with a cancer.

In another embodiment, the cancer is breast cancer, lymph cancer, leukemia, lung cancer, ovarian cancer, cervix cancer, testis cancer, liver cancer, melanoma, colon cancers, rectal cancer, renal-cell carcinoma, cancer of the small intestine and cancer of the esophagus, head and neck cancer, bladder cancer, prostate cancer, pancreatic cancer or pharynx cancer.

In the seventh aspect, the present invention provides a method for preparing the compound of Formula (A7) of the first aspect of the invention, comprising step of:

(i) reacting a compound of A5 with an acid in an inert solvent to form a compound of A6,

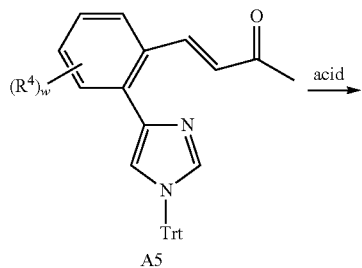

(ii) reducing the compound of formula A6 with a reducing agent, optionally followed by removing a protecting group in G, if present, to form a compound of A7,

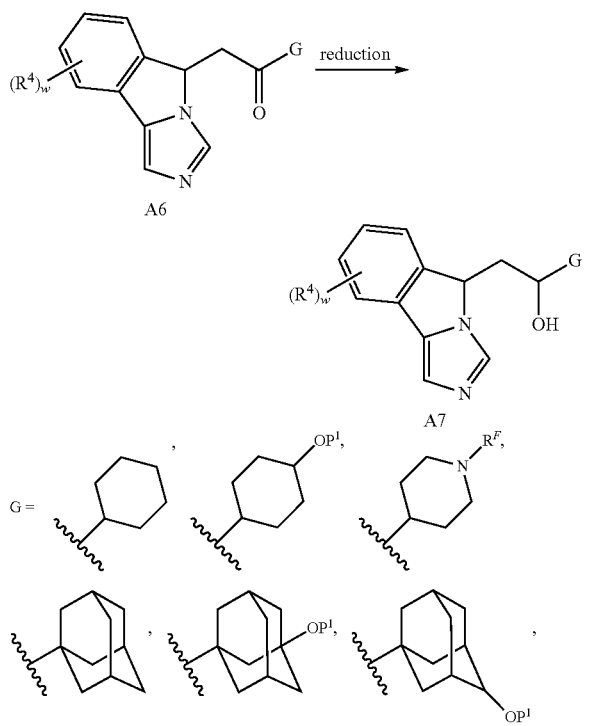

P¹ is a protecting group or H
R^F is phenyl, 5 to 10-membered heteroaryl, $C_{3-6}$ cycloalkyl, and 4 to 6-membered heterocyclyl, each optionally substituted It should be understood that in the present invention, the technical features specifically described above and below (such as the Examples) can be combined with each other, thereby constituting a new or preferred technical solution, which needs not be specified.

DETAILED DESCRIPTION OF THE INVENTION

Definitions

As use herein, unless clearly indicated otherwise, use of the terms "a", "an" and the like refers to one or more.

As used herein, the word "or" has the meaning of both "or" and "and" and is equivalent to "and/or"—unless otherwise specifically limited to just "or."

As used herein, unless otherwise stated, a chiral carbon atom (or chiral center) of the compound(s) in the invention is optionally R-type, S-type, or a combination thereof.

As used herein, unless otherwise stated, the term "alkyl," by itself or as part of another substituent (which may include the short form of "alk," e.g., alkoxy), refers to a straight (i.e. unbranched), branched chain, or cyclic hydrocarbon radical, or combination thereof, which may be fully saturated, mono- or polyunsaturated and can include di- and multivalent radicals. When an alkyl is preceded by a carbon-number modifier, e.g., $C_{1-10}$, its means the alkyl group contains 1 to 10 carbon atoms. For instance, examples of $C_{1-8}$ alkyl may include a linear or branched alkyl having 1-8 carbon atoms, such as methyl, ethyl, propyl, isopropyl, butyl, isobutyl, sec-butyl, and t-butyl.

As used herein, the term "alkenyl," by itself or as part of another substituent, refers to a straight chain, or branched hydrocarbon chains having at least one carbon-carbon double bond. An alkenyl group with one double bond can be denoted as —$C_nH_{2n-1}$ or —$C_nH_{2n-3}$ with two double bonds. When an alkenyl is preceded by a carbon-number modifier, e.g., $C_{2-8}$, it means the alkenyl group contains 2 to 8 carbon atoms. For instance, examples of $C_{2-8}$ alkenyl may include vinyl, allyl, 1,2-butenyl, 2,3-butenyl, and butadienyl.

As used herein, the term "alkynyl," by itself or as part of another substituent, refers to an aliphatic hydrocarbon group with at least one carbon-carbon triple bond. An alkynyl group may be linear or branched or combinations thereof. In some embodiments, it can contain 2 to 12 (e.g., 2 to 8, 2 to 6, or 2 to 4) carbon atoms. When an alkynyl is preceded by a carbon-number modifier, e.g., $C_{2-8}$, it means the alkynyl group contains 2 to 8 carbon atoms. Examples of an alkynyl group (e.g., $C_{2-8}$ alkynyl) may include acetenyl, propynyl, isopropynyl, 1-butynyl, isobutynl, and sec-butynyl.

As used herein, the term "cycloalkyl," by itself or as part of another substituent, refers to a saturated or partially saturated carbocyclic mono-, bi-, or tri-cyclic (fused or bridged or spiral) ring system. It can contain 3 to 12 (e.g., 3 to 10, or 5 to 10) carbon atoms. When a cycloalkyl group is preceded by a carbon-number modifier, e.g., $C_{3-10}$, it means the cycloalkyl group contains 3 to 10 carbon atoms. In some embodiments, the term "$C_{3-10}$ cycloalkyl" may refer to a saturated or partially saturated mono- or bicyclic alkyl ring system containing 3 to 10 carbon atoms, such as cyclopropyl, cyclobutyl, cyclopentyl, cyclohexyl, cycloheptyl, adamantly, and bicyclo[2,2,2]octyl.

As used herein, the term "alkoxy" or "alkyloxy" refers to an alkyl group linked by an oxygen atom (i.e., —O-alkyl), wherein alkyl is as defined above. Specific examples of "alkoxy" include, but are not limited to, methoxy, ethoxy, n-propoxy, isopropoxy, n-butoxy, iso-butoxy, sec-butoxy, t-butoxy cyclohexyloxy, and cyclopentyloxy. An alkoxy group can be optionally substituted with one or more appropriate substituents such as halogen, amino, cyano, or hydroxyl. An alkoxy group can be straight or branched. When an alkoxy group is preceded by a carbon-number modifier, e.g., $C_{1-8}$, it means the alkoxy group contains 1 to 8 carbon atoms.

As used herein, the term "halo" or "halogen," by itself or as part of another substituent (e.g., haloalkyl), may refer to and include F, Cl, Br, and/or I.

As used herein, the term "alkoxycarbonyl" refers to a straight or branched chain alkoxycarbonyl moiety. It can contain 1 to 8 carbon atoms. When an alkoxycarbonyl group is preceded by a carbon-number modifier, e.g., $C_{1-8}$, it means the alkoxycarbonyl group contains 1 to 8 carbon atoms. For instance, $C_{1-8}$alkoxycarbonyl may refer to a group having the structure of $C_{1-8}$ alkyloxyC(=O)—, such as methoxycarbonyl, ethoxycarbonyl, and t-butoxycarbonyl.

As used herein, a "carbonyl" group refers to —C(O)— or —C(=O)—.

As used herein, the term "aryl," by itself or as part of another substituent, refers to and includes monocyclic, bicyclic, or polycyclic aromatic hydrocarbon radicals. An aryl group can be substituted or unsubstituted. When an aryl group is preceded by a carbon-number modifier, e.g., $C_{6-12}$, it means the aryl group contains 6 to 12 carbon atoms. Examples of an aryl group include but are not limited to phenyl, and naphthyl.

As used herein, the term "heteroaryl," by itself or as part of another substituent, refers to a monocyclic or polycyclic aromatic hydrocarbon radicals, having the number of annular carbon atoms designated (e.g., $C_{4-10}$ means four to ten annular carbon atoms) and containing at least one or more of the same or different heteroatoms each independently being N, O, or S. Each carbon atom may be optionally substituted. A heteroaryl group may be 5- to 15-membered aromatic group containing 1 to 4 heteroatoms each independently being N, O, or S. A heteroaryl group may include a nitrogen containing heteroaryl, an oxygen containing heteroaryl, a sulfur containing heteroaryl.

As used herein, the term "nitrogen containing heteroaryl" refers to an aromatic group having one or more nitrogen atoms in the ring(s). Preferably, it is $C_{4-10}$ nitrogen containing heteroaryl which is an aromatic group having 4 to 10 carbon atoms and one or more nitrogen atoms in the ring. Specific examples include but are not limited to substituted or unsubstituted pyridinyl, pyrimidinyl, and pyrrolyl.

As used herein, the term "oxygen containing heteroaryl" refers to an aromatic group having one or more oxygen atoms in the ring(s). Preferably, it is $C_{4-10}$ nitrogen-containing heteroaryl which is an aromatic group having 4 to 10 carbon atoms and one or more oxygen atoms in the ring(s), such as optionally substituted furyl and benzofuryl.

As used herein, the term "sulfur containing heteroaryl" refers to an aromatic group having one or more sulfur atoms in the ring(s). Preferably, it is $C_{4-10}$ sulfur containing heteroaryl which is an aromatic group having 4 to 10 carbon atoms and one or more sulfur atoms in the ring, such as optionally substituted thienyl.

As used herein, the term "heterocyclyl," by itself or as part of another substituent (such as in aryl-heterocyclyl, heteroaryl-heterocyclyl, cycloalkyl-heterocyclyl, heterocyclyl-heterocyclyl, or heterocyclyl-aryl), refers to mono- or polycyclic radicals which may be saturated, partially saturated, or fully unsaturated, having the number of annular carbon atoms designated (e.g., $C_{3-11}$ means three to eleven annular carbon atoms) and containing at least one or more of the same or different heteroatoms each independently being N, S, or O. A heterocyclyl group may be 3- to 15-membered group containing 1 to 4 heteroatoms each independently being N, O, or S. A heteroaryl group may include a nitrogen containing heterocyclyl, oxygen containing heterocyclyl, and sulfur containing heterocyclyl, nitrogen and oxygen containing heterocyclyl, nitrogen and sulfur containing heterocyclyl, sulfur and oxygen containing heterocyclyl, etc.

As used herein, the term "optionally" (e.g., as in "optionally substituted with") means that the moiety at issue is either substituted or not substituted, and that the substitution occurs only when it is chemically feasible. For instance, H cannot be substituted with a substituent and a covalent bond or —C(=O)— group cannot be substituted with a substituent.

As used herein, an "oxo" or "oxide" group refers to =O.

As used herein, the term "pharmaceutically acceptable salt"—unless otherwise specified—refers to salts which are suitable for use in contact with the tissues of a subject (e.g., human) without excessive adverse effect. In some embodiments, pharmaceutically acceptable salts include salts of a compound of the invention having an acidic group (e.g., potassium salts, sodium salts, magnesium salts, calcium salts) or a basic group (e.g., sulfate, hydrochloride, phosphate, nitrate, carbonate salts).

As used herein, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different in every position. A ring substituent, such as a heterocycloalkyl, can be bound to another ring, such as a cycloalkyl, to form a Spiro-bicyclic ring system, e.g., both rings share one common atom. As one of ordinary skill in the art will recognize, combinations of substituents envisioned by this invention are those combinations that result in the formation of stable or chemically feasible compounds. Examples of the substituents include but are not limited to $C_{1-8}$ alkyl, $C_{2-8}$ alkenyl, $C_{2-8}$ alkynyl, $C_{3-10}$ cycloalkyl, $C_{1-8}$alkyloxy, halogen, hydroxyl, carboxyl(—COOH), $C_{1-8}$aldehyde, $C_{2-10}$acyl, $C_{2-10}$ ester, amino, amido, phenyl. For instance, a phenyl may be optionally substituted with 1-3 substituents each independently is halogen, $C_{1-10}$ alkyl, cyano, OH, nitro, $C_{3-10}$ cyclic hydrocarbyl, $C_{1-8}$ alkoxy, or amino.

Unless specifically otherwise defined, all the terms used herein have their common meanings as known to a skilled person in the art.

In one preferred embodiment, a compound of Formula (I) is selected from the compounds shown in FIG. 2 above.

In a preferred embodiment, each of R, $R^1$, $R^2$, $R^3$, $R^4$, $R^5$, $R^6$, $R^A$, $R^B$, $R^C$, $R^{A1}$ and $R^{A2}$ in Formula (I) independently is selected from the corresponding groups included by the specific compounds prepared in the Examples.

It should be understood that a deuterium-enriched derivative or different crystal forms of a compound of Formula (I) also fall with the scope of the present General Synthetic Schemes for the Compounds of this Invention Generally, the reaction is carried out in an inert solvent and at a temperature of −40 to reflux temperature (such as 100 or 120° C.) with a reaction time of from 1 min to 72 hours and preferably 0.1-24 hrs or 0.2-12 hrs. The exemplary solvents and temperature are those used in the Examples.
Scheme A Illustrates a General Synthesis of Compound A7.
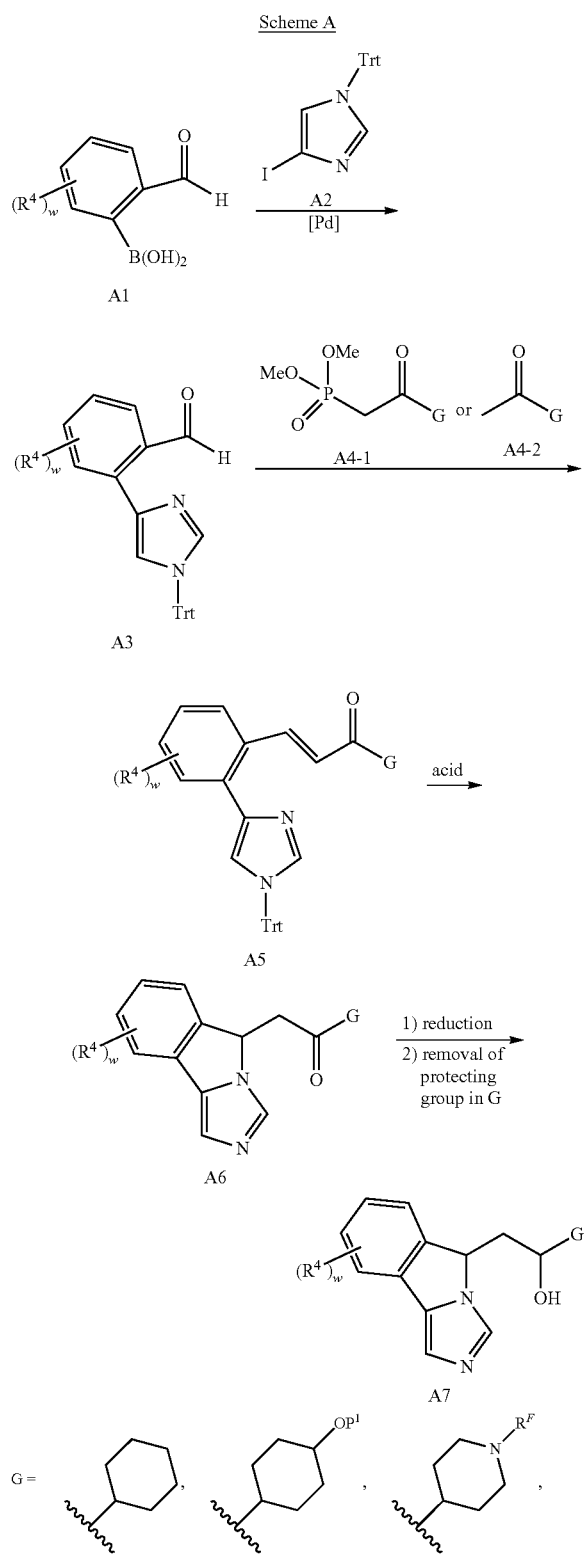
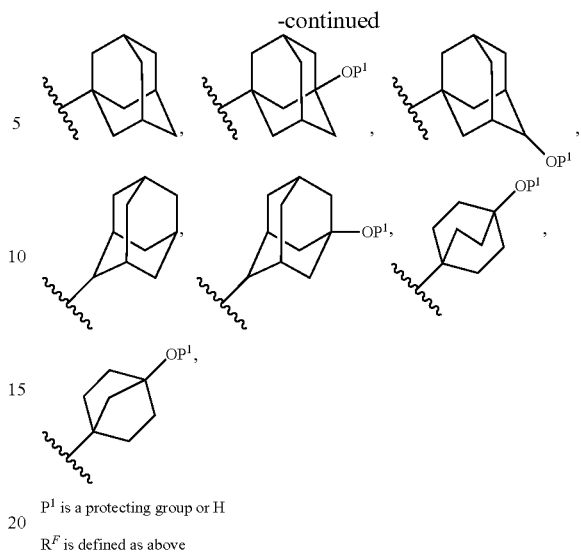
$P^1$ is a protecting group or H
$R^F$ is defined as above
Scheme B Illustrates a General Synthesis of Compound B3.
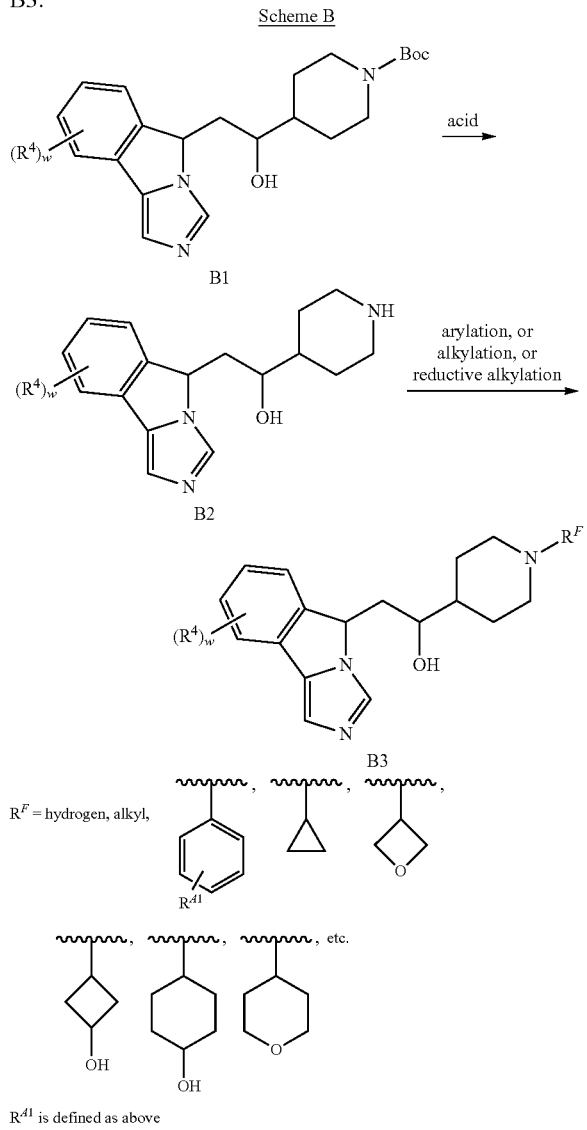
$R^{A1}$ is defined as above Scheme C Illustrates a General Synthesis of Compound C8.
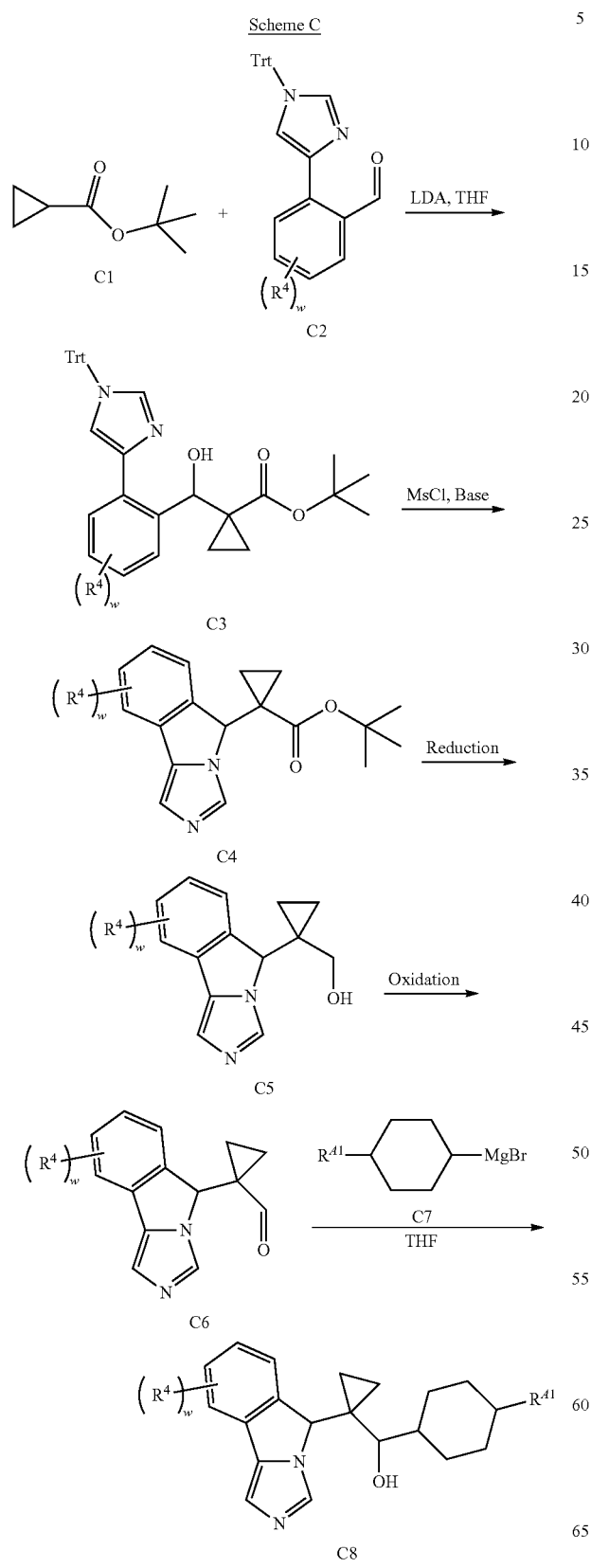
Scheme D Illustrates an Alternate Synthesis of Compound D11.
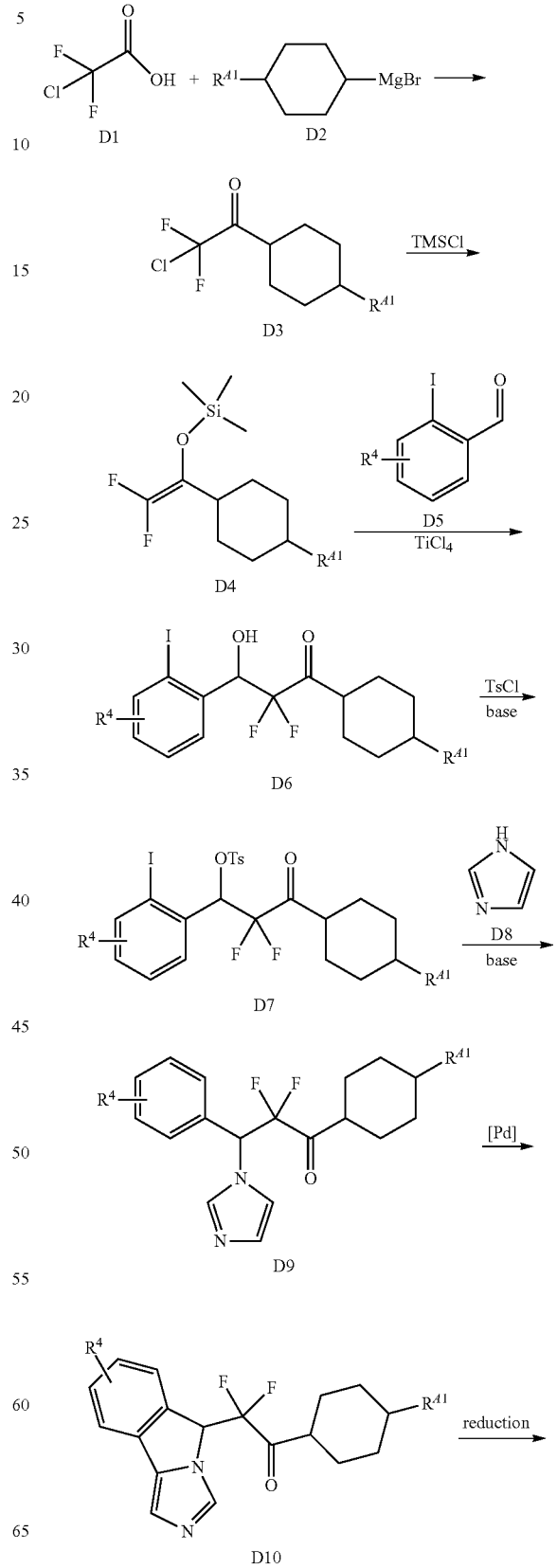

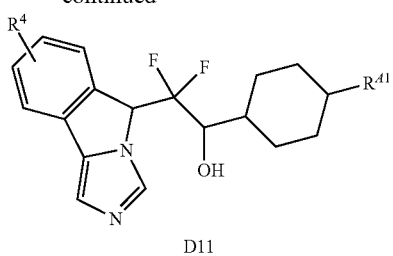

D11

Scheme E Illustrates an Alternate Synthesis of Compound E7.

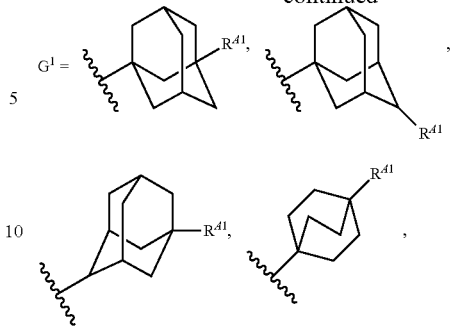

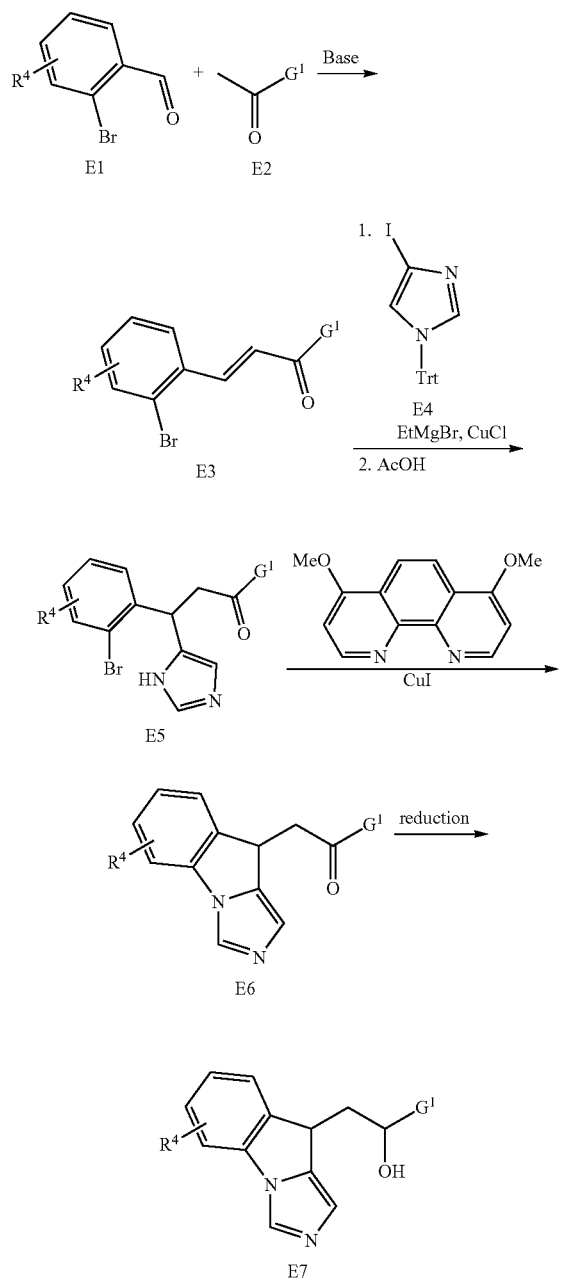

In the above schemes, $R^4$, $R^{41}$, and w are defined as above.

Pharmaceutical Compositions and Administration Thereof

The compounds provided by the present invention are useful as inhibitors of IDO (indoleamine 2,3-dioxygenase) and/or TDO (tryptophan 2,3-dioxygenase). Therefore, these compounds can be used for treatment of cancer, infectious disease, inflammation, cataracts, endometriosis, pain, atherosclerosis, neurological or neuropsychiatric conditions.

The pharmaceutical composition according to the present invention comprises (i) a safe and effective amount of the compounds of the invention or the pharmaceutical acceptable salts thereof and (ii) a pharmaceutically acceptable excipient or carrier. As used herein, the term "safe and effective amount" means an amount of the compounds which is sufficient to improve the patient's condition and will not induce any serious side effect. Generally, the pharmaceutical composition contains 0.01-500 mg compounds of the invention/dose, preferably 0.10-100 mg compounds of the invention/dose. In some embodiments, "one dose" refers to a capsule or tablet.

A "pharmaceutically acceptable carrier" means one or more compatible solid or liquid fillers or gel materials, which are suitable for human, and usually must have sufficient purity and sufficiently low toxicity. The term "compatibility" as used herein means that the components of the compositions can be blended with the compounds of the invention or with each other, and would not significantly reduce the efficacy of the compounds. Examples of pharmaceutically acceptable carriers include but are not limited to cellulose and the derivatives thereof (such as sodium carboxymethyl cellulose, sodium ethyl cellulose, cellulose acetate, etc.), gelatin, talc, solid lubricants (such as stearic acid and magnesium stearate), calcium sulfate, vegetable oils (such as soybean oil, sesame oil, peanut oil, olive oil, etc.), polyols (such as propylene glycol, glycerol, mannitol, sorbitol, etc.), emulsifiers (such as Tween®), wetting agent (such as sodium dodecyl sulfate), coloring agents, flavoring agents, stabilizers, antioxidants, preservatives, and pyrogen-free water.

There is no special limitation to the route of administration for the compounds or pharmaceutical compositions of the invention. The representative administration route includes but is not limited to: oral, parenteral (intravenous, intramuscular or subcutaneous), and topical administration.

Solid dosage forms for oral administration include capsules, tablets, pills, powders and granules. In these solid dosage forms, the active compounds are mixed with at least one conventional inert excipient (or carrier), such as sodium citrate or dicalcium phosphate, or mixed with the following components: (a) fillers or compatibilizer, for example, starch, lactose, sucrose, glucose, mannitol and silicic acid; (b) binders, for example, hydroxymethyl cellulose, alginates, gelatin, polyvinylpyrrolidone, sucrose and gum arabic; (c) humectant, such as, glycerol; (d) disintegrating agents such as agar, calcium carbonate, potato starch or tapioca starch, alginic acid, certain complex silicates, and sodium carbonate; (e) dissolution-retarding agents, such as paraffin; (f) absorption accelerators, for example, quaternary ammonium compounds; (g) wetting agents, such as cetyl alcohol and single glyceryl stearate; (h) adsorbents, for example, kaolin; and (i) lubricants such as talc, stearin calcium, magnesium stearate, solid polyethylene glycol, sodium lauryl sulfate, or the mixtures thereof. In capsules, tablets and pills, the dosage forms may also contain buffer.

The solid dosage forms such as tablets, sugar pills, capsules, pills and granules can be prepared by using coating and shell material, such as enteric coatings and other materials known in the art. They can contain opaque agent, and the release of the active compounds or compounds in such compositions can be delayed for releasing in certain portion of the digestive tract. Instance of the embedding components can be polymers and waxes. If necessary, the active compounds and one or more above excipients can be prepared into microcapsules.

Liquid dosage forms for oral administration include pharmaceutically acceptable emulsions, solutions, suspensions, syrups or tinctures. In addition to the active compounds, the liquid dosage forms may contain conventional inert diluent known in the art, such as water or other solvent, solubilizer and emulsifier, for example, ethanol, isopropanol, ethyl carbonate, ethyl acetate, propylene glycol, 1,3-butanediol, dimethyl formamide, as well as oil, in particular, cottonseed oil, peanut oil, corn germ oil, olive oil, castor oil and sesame oil, or the mixtures thereof and so on.

Besides the inert diluents, the composition may also contain additives such as wetting agents, emulsifiers, and suspending agent, sweetener, flavoring agents and perfume.

In addition to the active compounds, the suspension may contain suspending agent, for example, ethoxylated isooctadecanol, polyoxyethylene sorbitol and sorbitan esters, microcrystalline cellulose, methanol aluminum and agar, or the mixtures thereof and so on.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, polyols and the suitable mixtures thereof.

The dosage forms of compounds of the invention for topical administration include ointments, powders, patches, aerosol, and inhalants. The active ingredients are mixed with physiologically acceptable carriers and any preservatives, buffers, or propellant if necessary, under sterile conditions.

The compounds of the invention can be administered alone, or in combination with other pharmaceutically acceptable compounds.

When the pharmaceutical compositions are used, a safe and effective amount of compounds of the present invention is administered or delivered to mammals in need thereof (such as human), wherein the dosage of administration is a pharmaceutically effective amount. For a person weighted about 60 kg, the daily dose is usually 1 to 2000 mg, preferably 20 to 500 mg. Of course, the particular dose should also depend on other factors, such as the route of administration, patient healthy status, etc., which are well within the skill of a skilled physician.

The compounds and pharmaceutical composition of the invention can be used for treating cancer, infectious disease, inflammation, cataracts, endometriosis, pain, atherosclerosis, neurological or neuropsychiatric conditions. As used herein, the term "cancer" is meant to include all types of cancerous growths or oncogenic processes, metastatic tissues or malignantly transformed cells, tissues, or organs, irrespective of histopathologic type or stage of invasiveness. Examples of cancerous disorders include, but are not limited to, solid tumors, soft tissue tumors, and metastatic lesions. Examples of solid tumors include malignancies, e.g., sarcomas, adenocarcinomas, and carcinomas, of the various organ systems, such as those affecting prostate, lung, breast, lymphoid, gastrointestinal (e.g., colon), and genitourinary tract (e.g., renal, urothelial cells), pharynx. Adenocarcinomas include malignancies such as most colon cancers, rectal cancer, renal-cell carcinoma, liver cancer, non-small cell carcinoma of the lung, cancer of the small intestine and cancer of the esophagus. Metastatic lesions of the aforementioned cancers can also be treated or prevented using the methods and compositions of the invention. The subject method can be useful in treating malignancies of the various organ systems, such as those affecting lung, breast, lymphoid, gastrointestinal (e.g., colon), bladder, genitourinary tract (e.g., prostate), pharynx, as well as adenocarcinomas which include malignancies such as most colon cancers, renal-cell carcinoma, prostate cancer and/or testicular tumors, non-small cell carcinoma of the lung, cancer of the small intestine and cancer of the esophagus. The examples of cancer include but are not limited to breast cancer, lymph cancer, lung cancer, ovarian cancer, liver cancer melanoma, colon cancers, rectal cancer, renal-cell carcinoma, cancer of the small intestine and cancer of the esophagus, bladder cancer, prostate cancer, or pharynx cancer, etc. As used herein, the term "infectious disease" is meant to include all types of viral infection caused by Heptitis C virus (HCV), human papilloma virus (HPV), human immunodeficiency virus (HIV), and/or cytomegalovirus (CMV).

The Main Advantages of the Present Invention Include at Least the Following:

(1) The invention provides novel heterocyclic compounds useful as inhibitors of IDO (indoleamine 2,3-dioxygenase) and/or TDO (tryptophan 2,3-dioxygenase).

(2) The invention reveals that these novel heterocyclic compounds of Formula (I) possess outstanding effect for inhibiting activity of IDO and TDO.

The present invention will be further illustrated below with reference to the specific examples. It should be understood that these examples are only to illustrate the invention but not to limit the scope of the invention. Unless indicated otherwise, parts and percentage are calculated by weight.

EXAMPLE 1

Preparation of 2-(5H-imidazo[5,1-a]isoindol-5-yl)-1-(1-phenylpiperidin-4-yl)ethanol (Compound 1)

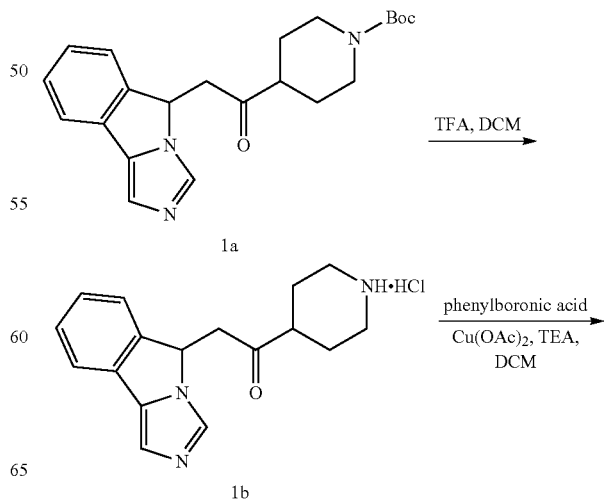

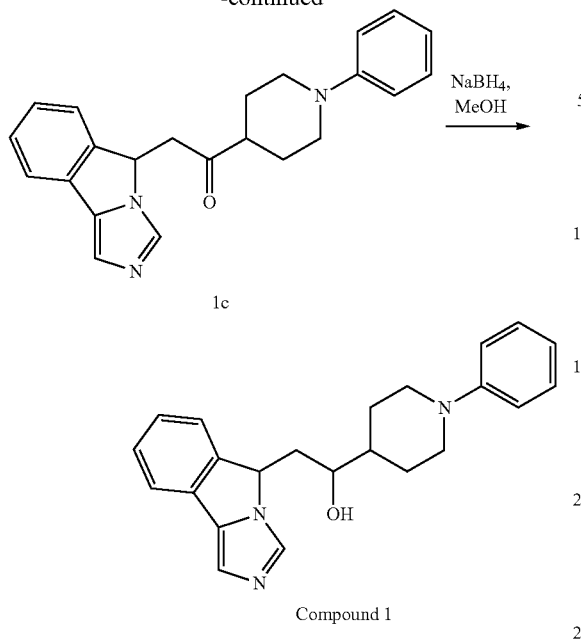

Compound 1

To the solution of 1a (100 mg, 0.26 mmol) in DCM (4.0 mL) wad added TFA (2.0 mL). The solution was stirred at rt for 1 hour. The solvent was removed in vacuo and the residue was dissolved in DCM (30 mL). The organic solvent was washed with $K_2CO_3$ (a.q, 1M, 5.0 mL) and brine (5.0 mL), dried and concentrated to afford 60 mg of crude product 1b as a yellow oil, which was used for next step directly. MS 282.2 $(M+H)^+$.

To the solution of 1b (60 mg, 0.21 mmol) in DCM (4.0 mL) was added TEA (0.2 mL), $Cu(OAc)_2$ (76 mg, 0.42 mmol) and phenylboronic acid (51 mg, 0.42 mmol). The mixture was stirred at room temperature (rt) for 24 hours and then filtered. DCM (10 mL) and MeOH (10 mL) was added to wash the solid. The filtrate was concentrated to dryness to afford 1c as a light green oil, which was used for next step directly. MS 358.3 $(M+H)^+$.

To a solution of crude 1c in MeOH (4.0 mL) was added $NaBH_4$ (32 mg, 0.84 mmol) batchwise. The mixture was stirred at rt for 2 hours. HCl (2 M, 0.5 mL) was added to the solution and the resulting mixture was concentrated to dryness. The residue was purified by silica-gel column (DCM:MeOH=40:1 with 0.5% ammonium hydroxide (28% w/w)). The obtained crude product was further purified by preparative TLC (DCM:MeOH=12:1 with 0.5% ammonium hydroxide (28% w/w)) to afford 21 mg of Compound 1 as a yellow solid. $^1$H NMR (a mixture of diastereomers, $CD_3OD$, 400 Hz): δ 7.88 and 7.84 (two s, 1H), 7.50 (d, J=7.6 Hz, 1H), 7.45 and 7.37 (two d, J=8.0 Hz, 1H), 7.29 (t, J=7.6 Hz, 1H), 7.31-7.27 (m, 1H), 7.12-7.08 (m, 2H), 7.05 and 7.02 (two s, 1H), 6.86 (d, J=8.0 Hz, 2H), 6.71 (t, J=7.2 Hz, 1H), 5.41 and 5.35 (d and t, J=10.0 Hz and J=5.6 Hz, 1H), 3.69-3.55 (m, 3H), 2.55-2.48 (m, 2H), 2.23-2.00 (m, 2H), 1.90-1.84 (m, 1H), 1.62-1.59 (m, 1H), 1.42-1.37 (m, 3H); MS 360.2 $(M+H)^+$.

EXAMPLE 2

Preparation of 2-(5H-imidazo[5,1-a]isoindol-5-yl)-1-(1-(pyridin-4-yl)piperidin-4-yl)ethanol (Compound 2)

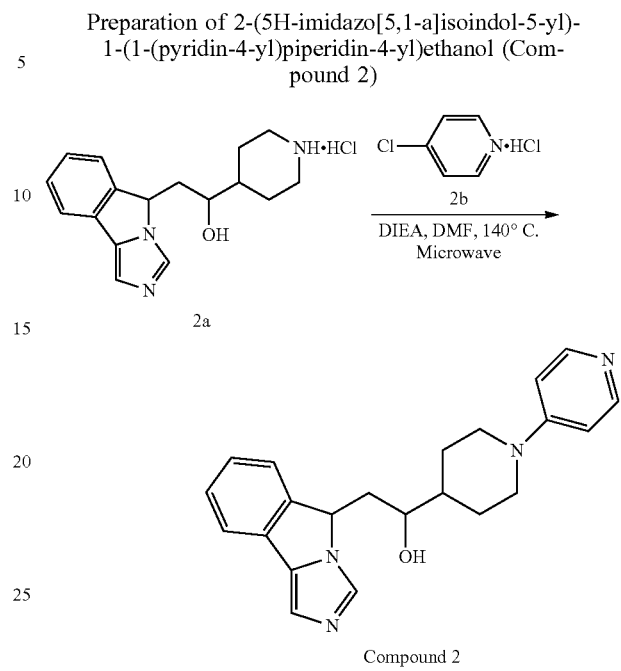

Compound 2

To the solution of 2a (200 mg, 0.63 mmol) in DMF (2.0 mL) wad added DIEA (542 mg, 4.2 mmol) and 4-chloropyridinium chloride (2b, 190 mg, 1.26 mmol). The mixture was heated to 140° C. in a microwave reactor and stirred at 140° C. for 30 min. The reaction mixture was concentrated to dryness. The residue was purified by silica-gel column (DCM:MeOH=20:1 with 0.5% ammonia solution (28% w/w)). The resulting product was further purified by prep-TLC (DCM:MeOH=10:1 with 0.5% ammonia solution (28% w/w)) to afford 24 mg of compound 2. $^1$H-NMR (a mixture of diastereomers, $CD_3OD$, 400 MHz): δ 8.05 (d, J=6.4 Hz, 2H), 7.97 and 7.92 (two s, 1H), 7.59 (d, J=7.6 Hz, 1H), 7.53 and 7.46 (two d, J=8.0 Hz and J=7.6 Hz, 1H), 7.39 (t, J=7.6 Hz, 1H), 7.32-7.28 (m, 1H), 7.15 and 7.12 (two s, 1H), 6.78 (d, J=6.4 Hz, 2H), 5.49 and 5.42 (dd and t, J=10.0 Hz, 2.8 Hz and J=6.4 Hz, 1H), 4.06-3.97 (m, 2H), 3.77-3.69 (m, 1H), 2.82 (td, J=12.8 Hz, 2.4 Hz, 2H), 2.33-1.91 (m, 2H), 1.77-1.36 (m, 5H); MS 361.2 $(M+H)^+$.

EXAMPLE 3

Preparation of 1-(1-cyclopropylpiperidin-4-yl)-2-(5H-imidazo[5,1-a]isoindol-5-yl)ethanol (Compound 3)

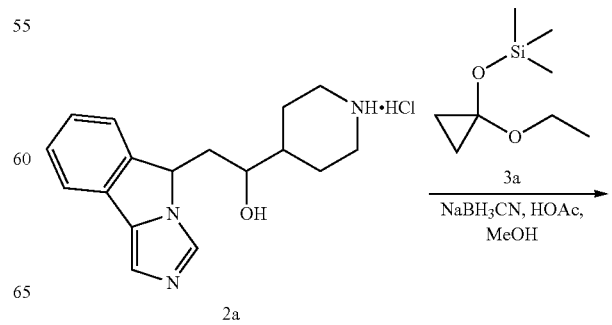

2a

-continued

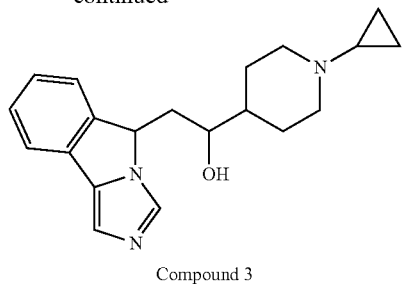

Compound 3

To the solution of 2a (200 mg, 0.63 mmol) in MeOH (5.0 mL) wad added TEA (0.2 mL). The solution was stirred at rt for 15 minutes. HOAc (1.0 mL) and (1-ethoxycyclopropoxy)trimethylsilane (3a, 220 mg, 1.26 mmol) was added and the solution was stirred for another 15 minutes. NaBH$_3$CN (80 mg, 1.26 mmol) was then added batchwise, followed by the addition of anhydrous magnesium sulfate (200 mg). The reaction mixture was refluxed for 30 hours. After the reaction was completed according to LCMS, the mixture was filtered and MeOH (10 mL) was added to wash the solid. The filtrate was concentrated and the residue was purified by silica-gel column (DCM:MeOH=40:1 with 0.5% ammonia solution (28% w/w)). The resulting product was further purified by prep-TLC (DCM:MeOH=20:1 with 0.5% ammonia solution (28% w/w)) to afford 25 mg of compound 3 as a white solid. $^1$H-NMR (a mixture of diastereomers, CD$_3$OD, 400 MHz): δ 7.95 and 7.90 (two s, 1H), 7.55 (d, J=7.6 Hz, 1H), 7.49 and 7.41 (two d, J=7.6 Hz, 1H), 7.35 (t, J=7.6 Hz, 1H), 7.28-7.24 (m, 1H), 7.13 and 7.10 (two s, 1H), 5.44 and 5.36 (dd and t, J=10.4 Hz, 2.4 Hz and t, J=6.4 Hz, 1H), 3.72-3.65 (m, 1H), 3.08-3.00 (m, 2H), 2.26-1.96 (m, 4H), 1.87-1.81 (m, 1H), 1.68-1.53 (m, 2H), 1.32-1.22 (m, 3H), 0.45-0.32 (m, 4H); MS 324.4 (M+H)$^+$.

EXAMPLE 4

Preparation of 2-(5H-imidazo[5,1-a]isoindol-5-yl)-1-(1-(oxetan-3-yl)piperidin-4-yl)ethanol (Compound 4)

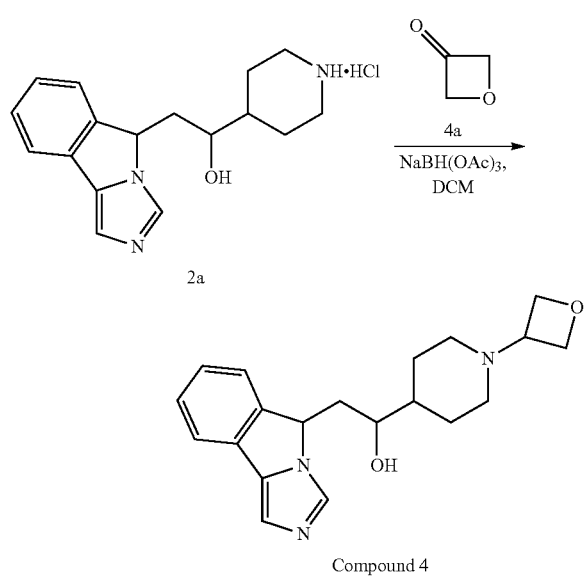

Compound 4

To the mixture of 2a (100 mg, 0.31 mmol) in DCM (2.0 mL) was added TEA (42 mg, 0.42 mmol). The mixture was stirred at rt for 10 minutes. Then oxetan-3-one (4a, 30 mg, 0.42 mmol) and HOAc (0.2 mL) was added. The mixture was stirred at rt for 30 minutes. After that, sodium triacetoxyborohydride (89 mg, 0.42 mmol) was added batchwise. The mixture was stirred at rt for 16 hours. The solvent was removed in vacuo. The residue was purified by silica-gel column (DCM:MeOH=25:1 with 0.5% ammonia solution (28% w/w)). The resulting product was further purified by prep-TLC (DCM:MeOH=15:1 with 0.5% ammonia solution (28% w/w)) to afford 13 mg of compound 4. $^1$H-NMR (a mixture of diastereomers, CD$_3$OD, 400 MHz): δ 7.97 and 7.93 (two s, 1H), 7.60 (d, J=7.6 Hz, 1H), 7.54 and 7.45 (two d, J=7.6 Hz, 1H), 7.39 (t, J=7.6 Hz, 1H), 7.30 (td, J=7.6 Hz, 0.8 Hz, 1H), 7.15 and 7.12 (two s, 1H), 5.50 and 5.42 (dd and t, J=10.0 Hz, 2.8 Hz and J=6.4 Hz, 1H), 4.68-4.64 (m, 2H), 4.60-4.55 (m, 2H), 3.77-3.72 (m, 1H), 3.47-3.41 (m, J=6.4 Hz, 1H), 2.86-2.78 (m, 2H), 2.16-2.02 (m, 2H), 1.89-1.75 (m, 3H), 1.63-1.60 (m, 1H), 1.42-1.25 (m, 3H); MS 340.2 (M+H)$^+$.

EXAMPLE 5

Preparation of 4-(4-(1-hydroxy-2-(5H-imidazo[5,1-a]isoindol-5-yl)ethyl)piperidin-1-yl)cyclohexanol (Compound 5)

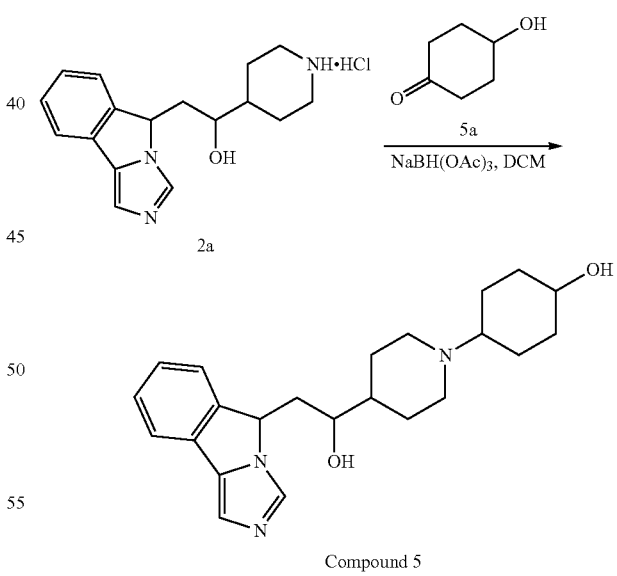

Compound 5

A mixture of 2a (180 mg, 0.56 mmol) and 4-hydroxycyclohexanone (5a, 64 mg, 0.56 mmol) in DCM (2 mL) was treated with TEA (0.12 mL, 0.87 mmol) for 20 min at room temperature. NaBH(OAc)$_3$ (354 mg, 1.68 mmol) was then added and the reaction mixture was stirred for 4 hours at room temperature. The reaction was quenched with saturated sodium bicarbonate and DCM. The combined organic layer was dried over anhydrous Na₂SO₄, filtered and concentrated to give the crude product, which was purified by column chromatography on silica gel (DCM:MeOH=5:1 with 0.5% ammonia solution (28% w/w)). The isolated product was further purified by prep-TLC (DCM: MeOH=5:1 with 0.5% ammonia solution (28% w/w)) to afford compound 5 as a light yellow solid (40 mg). $^1$H NMR (a mixture of diastereomers, CD₃OD, 400 Hz): δ 7.97 and 7.93 (two s, 1H), 7.61 (d, J=7.6 Hz, 1H), 7.55 and 7.47 (two d, J=7.6 Hz, 1H), 7.40 (t, J=7.6 Hz, 1H), 7.33-7.29 (m, 1H), 7.16 and 7.13 (two s, 1H), 5.51 and 5.44 (d and t, J=8.0 Hz and J=5.6 Hz, 1H), 3.81-3.78 (m, 1H), 3.43-3.38 (m, 1H), 3.02-2.72 (m, 3H), 2.19-2.13 (m, 1H), 2.09-2.02 (m, 4H), 1.94-1.78 (m, 5H), 1.64-1.46 (m, 5H); MS 382.3 (M+H)⁺.

EXAMPLE 6

Preparation of 5-(2-cyclohexyl-2,2-difluoroethyl)-5H-imidazo[5,1-a]isoindole (Compound 6)

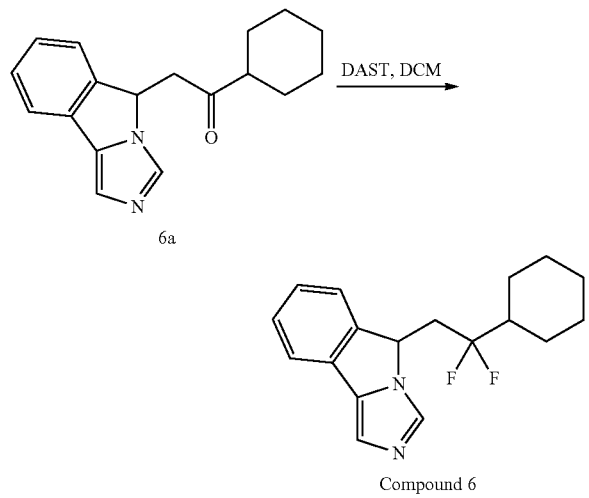

To a solution of 6a (100 mg, 0.36 mmol) in DCM (2 ml) was added diethylaminosulfurtrifluoride (DAST, 287 mg, 1.785 mmol) dropwise at 0° C. Then the reaction mixture was stirred at r.t. for 40 h. The mixture was added slowly to ice water and extracted with DCM twice. The organic phases was dried with Na₂SO₄, filtered and concentrated in vacuo. The resulting crude product was purified by prep-TLC (DCM:MeOH=70:1), and then by prep-HPLC (column, Waters X-Select Prep C18 5 μm 30*100 mm; Flow Rate (ml/min): 20; Injection Volume (μL): 500; Mobile A: ACN; Mobile B: H₂O (10 mmol NH₄HCO₃); Gradient: B from 45% to 25% for 9.60 min, from 25% to 5% for 1.00 min and hold 5% for 3.05 min, from 5% to 45% for 0.20 min and hold 45% for 4.15 min) to afford the compound 6 as a light yellow solid (5 mg). $^1$H NMR (CD₃OD, 400 Hz): δ 7.86 (s, 1H), 7.60 (d, J=7.6 Hz, 1H), 7.50 (d, J=7.6 Hz, 1H), 7.41 (t, J=7.6 Hz, 1H), 7.33 (td, J=7.6 Hz, 1.2 Hz, 1H), 7.14 (s, 1H), 5.59 (dd, J=8.4 Hz, 2.4 Hz, 1H), 2.82-2.68 (m, 1H), 2.44-2.29 (m, 1H), 1.92-1.89 (m, 2H), 1.85-1.82 (m, 2H), 1.72-1.70 (m, 1H), 1.35-1.18 (m, 6H); MS 303.2 (M+H)⁺.

EXAMPLE 7

Preparation of 2-(5H-imidazo[5,1-a]isoindol-5-yl)-1-(1-(2-nitrophenyl)piperidin-4-yl)ethanol (Compound 7)

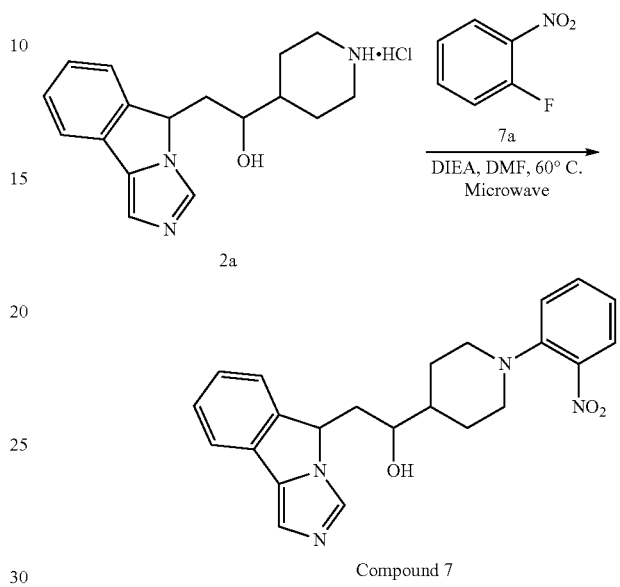

A mixture of 2a (60 mg, 0.212 mmol), 7a (60 mg, 0.425 mmol) and DIPEA (90 mg, 0.698 mmol) in DMF (2 mL) was stirred under microwave irradiation at 60° C. for 0.5 h. The mixture was cooled to room temperature, diluted with water (10 mL) and extracted with EtOAc (10 mL×3). The combined organic layers were washed with brine (10 mL), dried over anhydrous Na₂SO₄, filtered and concentrated to give a residue, which was purified by preparative TLC (CH₂Cl₂:MeOH=15:1) to afford compound 7 (15 mg, 17% yield) as a yellow solid. $^1$HNMR (a mixture of diastereomers, CD₃OD, 400 MHz) δ 8.02 and 7.98 (two s, 1H), 7.72 (dd, J=8.0 Hz, 1.6 Hz, 1H), 7.65-7.25 (m, 6H), 7.18 and 7.16 (two s, 1H), 7.08 (t, J=8.0 Hz, 1H), 5.56-5.46 (m, 1H), 3.84-3.75 (m, 1H), 3.39-3.23 (m, 2H), 2.86-2.79 (m, 2H), 2.34-2.22 (m, 2H), 1.98-1.90 (m, 1H), 1.72-1.43 (m, 4H); MS 405.3 [M+H]⁺.

EXAMPLE 8

Preparation of 2-(5H-imidazo[5,1-a]isoindol-5-yl)-1-(1-(4-(trifluoromethyl)phenyl)piperidin-4-yl)ethanol (Compound 8)

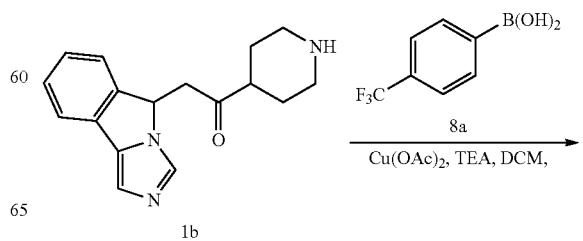

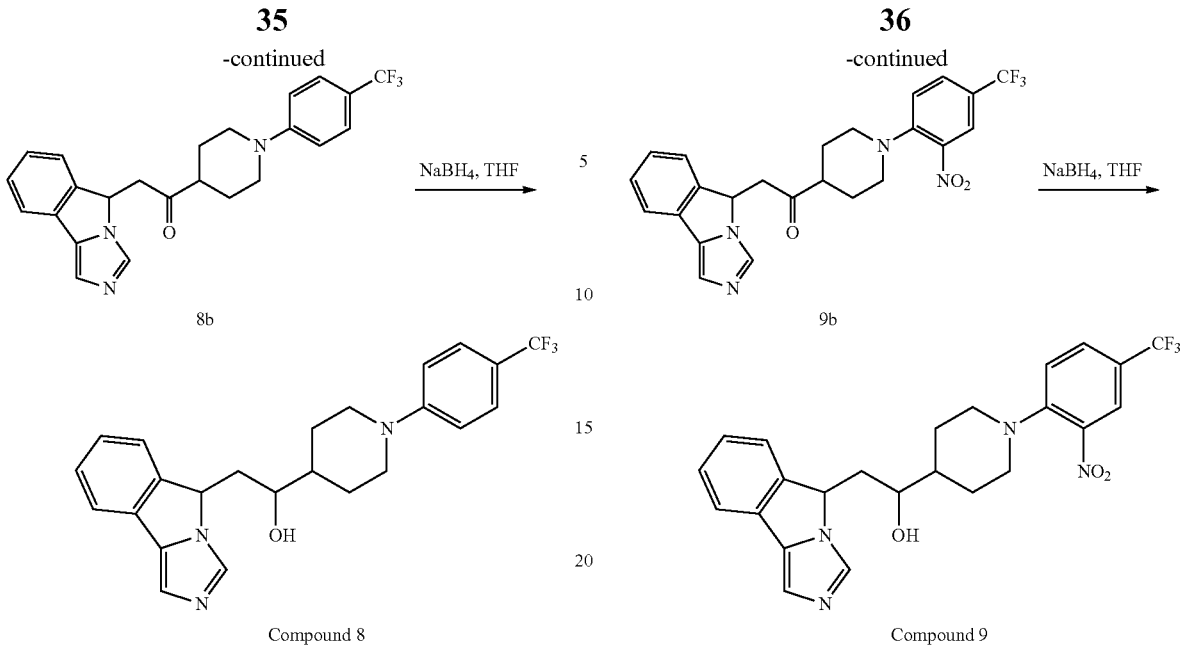

Compound 8 (left) / Compound 9 (right)

A mixture of compound 1b (56 mg, 0.199 mmol), compound 8a (57 mg, 0.300 mmol), Cu(OAc)₂ (36 mg, 0.198 mmol) and Et₃N (60 mg, 0.594 mmol) in CH₂Cl₂ (2 mL) was stirred under O₂ atmosphere at room temperature for 24 h. The reaction mixture was filtered and washed with CH₂Cl₂ (10 mL×3). The filtrate was concentrated in vacuo to give a residue, which was purified by preparative TLC (CH₂Cl₂:MeOH=20:1) to afford compound 8b (25 mg, 30% yield) as a yellow solid. MS 426.2 [M+H]⁺.

To a stirred solution of compound 8b (36 mg, 0.085 mmol) in THF (1 mL) was added NaBH₄ (10 mg, 0.263 mmol) at 0° C. Then the mixture was stirred at room temperature for 30 min. The mixture was quenched with ice cold NH₄Cl solution (10 mL) and extracted with EtOAc (10 mL×3). The combined organic layers were washed with brine (10 mL), dried over anhydrous Na₂SO₄, filtered and concentrated in vacuo to give a residue, which was purified by preparative TLC (CH₂Cl₂:MeOH=15:1) and then purified by preparative TLC (CH₂Cl₂: CH₃CN=1:1) to afford compound 8 (4.7 mg, 13% yield) as a yellow solid. ¹HNMR (a mixture of diastereomers, CD₃OD, 400 Hz) δ 8.00 and 7.95 (two s, 1H), 7.61 (d, J=7.2 Hz, 1H), 7.55 (d, J=7.6 Hz, 1H), 7.49-7.37 (m, 3H), 7.34-7.28 (m, 1H), 7.14 (s, 1H), 7.01 (d, J=8.8 Hz, 2H), 5.48-5.42 (m, 1H), 3.96-3.83 (m, 2H), 3.81-3.74 (m, 1H), 2.80-2.70 (m, 2H), 2.21-2.06 (m, 2H), 2.00-1.92 (m, 1H), 1.76-1.67 (m, 1H), 1.59-1.40 (m, 3H); MS 428.2 [M+H]⁺.

EXAMPLE 9

Preparation of 2-(5H-imidazo[5,1-a]isoindol-5-yl)-1-(1-(2-nitro-4-(trifluoromethyl)phenyl)piperidin-4-yl)ethanol (Compound 9)

To a stirred solution of compound 1a (150 mg, 0.393 mmol) in CH₂Cl₂ (1.5 mL) was added TFA (0.5 mL) slowly. The mixture was stirred at room temperature for 2 h, and concentrated to dryness under reduced pressure. The residue was diluted with DMF (2 mL), then K₂CO₃ (215 mg, 1.556 mmol) was added, followed by compound 9a (123 mg, 0.588 mmol). The mixture was stirred at room temperature for 16 h, and quenched with water (6 mL) and extracted with EtOAc (6 mL×3). The combined organic layers were washed with brine (6 mL), dried over anhydrous Na₂SO₄, filtered and concentrated in vacuo to give a residue, which was purified by preparative TLC (petroleum ether: EtOAc=1:1) to afford compound 9b (30 mg, 16% yield for two steps) as a yellow solid. MS 471.1 [M+H]⁺.

To a stirred solution of compound 9b (30 mg, 0.085 mmol) in THF (1 mL) was added NaBH₄ (5 mg, 0.132 mmol) at 0° C. Then the mixture was stirred at room temperature for 20 min. The mixture was quenched with ice cold aqueous NH₄Cl solution (10 mL) and extracted with EtOAc (10 mL×3). The combined organic layers were washed with brine (10 mL), dried over anhydrous Na₂SO₄, filtered and concentrated in vacuo to give a residue, which was purified by preparative TLC (CH₂Cl₂:MeOH=15:1) to afford compound 9 (15 mg, 50% yield) as a yellow solid. ¹HNMR (a mixture of diastereomers, CD₃OD, 400 Hz) δ 8.07-7.95 (m, 2H), 7.72 (dd, J=8.8 Hz, 2.0 Hz, 1H), 7.61 (d, J=7.6 Hz, 1H), 7.56 (d, J=7.6 Hz, 1H), 7.43-7.29 (m, 3H), 7.16 and 7.14 (two s, 1H), 5.55-5.42 (m, 1H), 3.82-3.73 (m, 1H), 3.49-3.31 (m, 2H), 2.96-2.88 (m, 2H), 2.20-2.07 (m, 2H), 1.97-1.88 (m, 1H), 1.72-1.64 (m, 1H), 1.60-1.44 (m, 3H); MS 473.2 [M+H]⁺.

EXAMPLE 10

Preparation of 1-((3r,5r,7r)-adamantan-1-yl)-2-(5H-imidazo[5,1-a]isoindol-5-yl)ethanol (Compound 10)

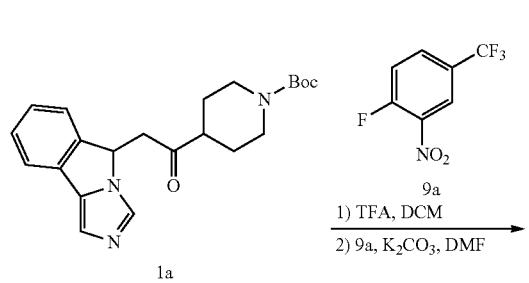

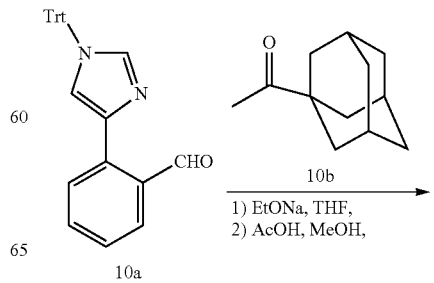

37

-continued

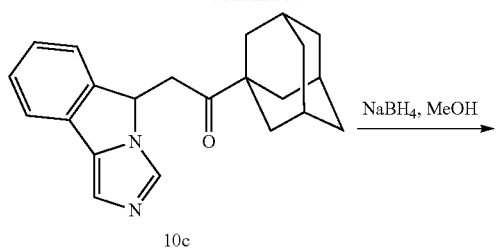

Compound 10

To a stirred mixture of compound 10a (97 mg, 0.234 mmol) and compound 10b (42 mg, 0.234 mmol) in anhydrous THF (10 mL) was added dropwise a solution of EtONa (21% in EtOH, 98 mg, 0.304 mmol) at room temperature. The reaction mixture was stirred at room temperature for 2 h, and concentrated to dryness under reduced pressure. The residue was diluted with NH$_4$Cl solution (10 mL) and extracted with EtOAc (10 mL×3). The combined organic layers were washed with brine (10 mL), dried over anhydrous Na$_2$SO$_4$, filtered and concentrated in vacuo to give a residue, which was dissolved in MeOH (8 mL). To this solution was added HOAc (2 mL), and the reaction mixture was stirred at 90° C. for 3 h. The mixture was concentrated in vacuo to give a residue, which was diluted with NaHCO$_3$ saturated solution (10 mL) and extracted with EtOAc (10 mL×3). The combined organic layers were washed with brine (10 mL), dried over anhydrous Na$_2$SO$_4$, filtered and concentrated in vacuo to give a residue, which was purified by preparative TLC (CH$_2$Cl$_2$:MeOH=50:1) to afford compound 10c (62 mg, 79% yield) as a grey solid. MS 333.1 [M+H]$^+$.

To a stirred solution of compound 10c (62 mg, 0.187 mmol) in MeOH (10 mL) was added NaBH$_4$ (21 mg, 0.560 mmol) at room temperature. Then the mixture was stirred at room temperature for 1 h. The mixture was quenched with ice cold aqueous NH$_4$Cl solution and extracted with EtOAc (10 mL×3). The combined organic layers were washed with brine (10 mL), dried over anhydrous Na$_2$SO$_4$, filtered and concentrated in vacuo to give a residue, which was purified by preparative TLC (CH$_2$Cl$_2$:MeOH=15:1) to afford compound 10 (54 mg, 87% yield) as a yellow solid. $^1$H NMR (a mixture of diastereomers, DMSO-d$_6$, 400 Hz): δ 7.95 (s, 1H), 7.61-7.56 (m, 2H), 7.40-7.36 (m, 1H), 7.30-7.25 (m, 1H), 7.11 (s, 1H), 5.37-5.34 (m, 1H), 4.86 (d, J=6.4 Hz, 1H), 3.38-3.31 (m, 1H), 2.11-2.03 (m, 1H), 1.98-1.89 (m, 3H), 1.80-1.73 (m, 1H), 1.69-1.40 (m, 12H); MS 335.2 [M+H]$^+$.

38

EXAMPLE 11

Preparations of 2-(5H-imidazo[5,1-a]isoindol-5-yl)-1-(4-morpholino-3-nitrophenyl)ethanol (Compound 11)

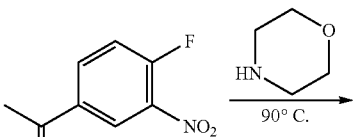

11a

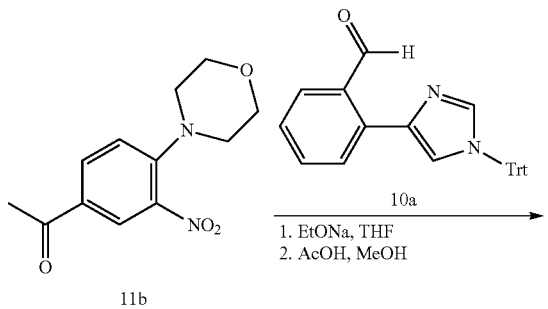

11b

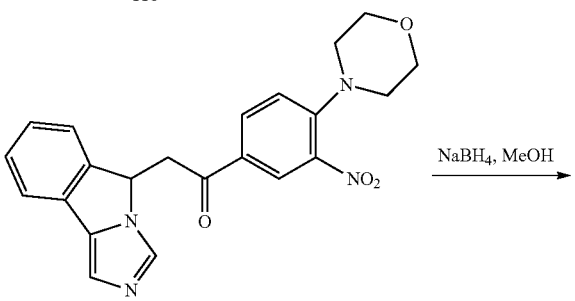

11c

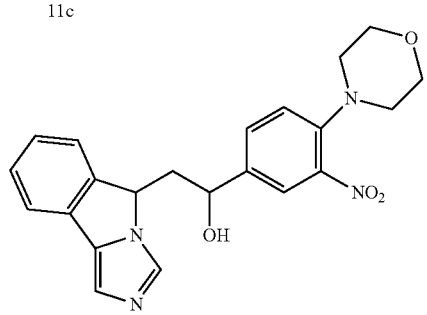

Compound 11

A mixture of 1-(4-fluoro-3-nitrophenyl)ethanone (0.20 g, 1.09 mmol) and morpholine (1.5 mL) was stirred at 90° C. for 3 h. The reaction mixture was cooled to room temperature, poured to 2 N HCl solution (10 mL) and extracted with EtOAc (10 mL×3). The combined organic layers were washed with brine (10 mL), dried over anhydrous Na$_2$SO$_4$, filtered and concentrated in vacuo to give a residue, which was triturated with a solution of petroleum ether and EtOAc (1:1). The resulting solid was collected by filtration and dried in vacuo to afford compound 11b (0.24 g, 88% yield) as a brown solid, which was used for the next step without further purification. MS 251.2[M+H]$^+$.

To a stirred mixture of compound 11b (0.18 g, 0.73 mmol) and compound K1-3 (0.30 g, 0.73 mmol) in anhydrous THF (15 mL) was added dropwise a solution of EtONa (21% in EtOH, 0.31 g, 0.94 mmol) at room temperature. The reaction mixture was stirred at room temperature for 2 h, and concentrated to dryness under reduced pressure. The residue was diluted with NH$_4$Cl solution (5 mL) and extracted with EtOAc (10 mL×3). The combined organic layers were washed with brine (10 mL×2), dried over anhydrous Na$_2$SO$_4$, filtered and concentrated in vacuo to give a residue, which was dissolved in MeOH (15 mL). To this solution was added HOAc (3 mL), and the reaction mixture was stirred at 90° C. for 3 h. The mixture was concentrated in vacuo to give a residue, which was diluted with saturated NaHCO$_3$ solution (10 mL) and extracted with EtOAc (10 mL×3). The combined organic layers were washed with brine (10 mL), dried over anhydrous Na$_2$SO$_4$, filtered and concentrated in vacuo to give a residue, which was purified by preparative TLC (CH$_2$Cl$_2$:MeOH=20:1) to afford compound 11c (0.15 g, 52% yield) as a yellow solid. MS 405.2 [M+H]$^+$.

To a stirred solution of compound 11c (0.15 g, 0.37 mmol) in MeOH (10 mL) was added NaBH$_4$ (0.04 g, 1.11 mmol) at 0° C. Then the mixture was stirred at room temperature for 1 h. The mixture was quenched with ice cold aqueous NH$_4$Cl solution (15 mL) and extracted with EtOAc (10 mL×3). The combined organic layers were washed with brine (10 mL×2), dried over anhydrous Na$_2$SO$_4$, filtered and concentrated in vacuo to give a residue, which was purified by preparative TLC (CH$_2$Cl$_2$:MeOH=15:1) to afford two isomers of compound 11: Isomer-1 (upper spot, 32.44 mg, 22% yield) as a yellow solid and Isomer-2 (lower spot, 22.30 mg, 15% yield) as a yellow solid. Isomer-1: $^1$H NMR (CD$_3$OD, 400 MHz): δ 7.79 (s, 1H), 7.61-7.57 (m, 2H), 7.55 (d, J=2.0 Hz, 1H), 7.43-7.39 (m, 2H), 7.37-7.32 (m, 1H), 7.19 (d, J=8.4 Hz, 1H), 7.01 (s, 1H), 5.48 (t, J=5.2 Hz, 1H), 4.82 (dd, J=7.6 Hz, J=6.4 Hz, 1H), 3.78 (t, J=4.8 Hz, 4H), 3.00 (t, J=4.8 Hz, 4H), 2.58-2.41 (m, 2H); MS 407.1 [M+H]$^+$. Isomer-2: $^1$H NMR (CD$_3$OD, 400 MHz): δ 8.06 (s, 1H), 7.71 (d, J=2.0 Hz, 1H), 7.58 (d, J=7.6 Hz, 1H), 7.49 (dd, J=8.0 Hz, J=1.6 Hz, 1H), 7.40-7.33 (m, 2H), 7.27-7.22 (m, 2H), 7.20 (s, 1H), 5.56 (dd, J=8.4 Hz, J=3.6 Hz, 1H), 4.93-4.89 (m, 1H), 3.79 (t, J=4.8 Hz, 4H), 3.04-2.98 (m, 4H), 2.68-2.59 (m, 1H), 2.14-2.06 (m, 1H); MS 407.2 [M+H]$^+$.

EXAMPLE 12

Preparation of 4-(4-(1-hydroxy-2-(5H-imidazo[5,1-a]isoindol-5-yl)ethyl)phenyl)morpholin-3-one (Compound 12)

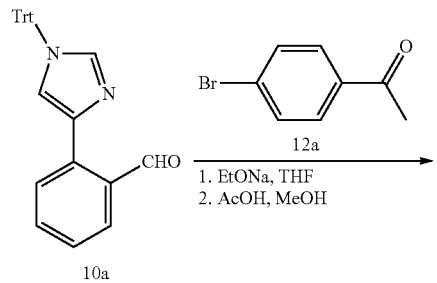

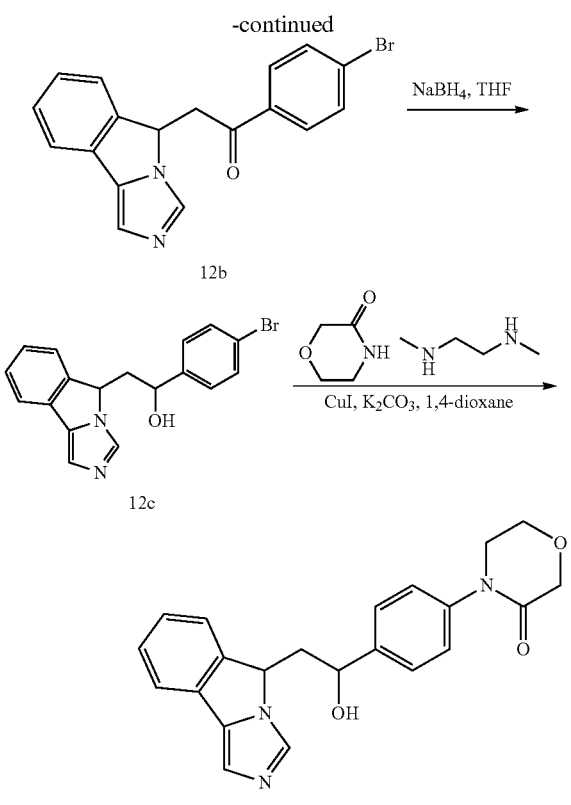

Compound 12

To a stirred mixture of compound 10a (500 mg, 1.21 mmol) and compound 1-(4-bromophenyl)ethanone (240 mg, 1.21 mmol) in anhydrous THF (20 mL) was added dropwise a solution of EtONa (21% in EtOH, 508 mg, 1.57 mmol) at room temperature. The reaction mixture was stirred at room temperature for 2 h, and concentrated to dryness under reduced pressure. The residue was diluted with NH$_4$Cl solution (20 mL) and extracted with EtOAc (20 mL×3). The combined organic layers were washed with brine (20 mL), dried over anhydrous Na$_2$SO$_4$, filtered and concentrated in vacuo to give a residue, which was dissolved in MeOH (16 mL). To this solution was added HOAc (4 mL), and the reaction mixture was stirred at 90° C. for 3 h. The mixture was concentrated in vacuo to give a residue, which was diluted with NaHCO$_3$ saturated solution (20 mL) and extracted with EtOAc (20 mL×3). The combined organic layers were washed with brine (20 mL), dried over anhydrous Na$_2$SO$_4$, filtered and concentrated in vacuo to give a residue, which was purified by preparative TLC (CH$_2$Cl$_2$:MeOH=50:1) to afford compound 12b (220 mg, 52% yield) as a yellow solid. MS 353.1[M+H]$^+$, 355.1[M+H]$^+$.

To a stirred solution of compound 12b (140 mg, 0.398 mmol) in anhydrous THF (5 mL) was added NaBH$_4$ (23 mg, 0.596 mmol) at 0° C. The mixture was stirred at 0° C. for 2 h. The mixture was quenched with ice cold aqueous NH$_4$Cl solution (5 mL) and extracted with EtOAc (5 mL×3). The combined organic layers were washed with brine (5 mL), dried over anhydrous Na$_2$SO$_4$, filtered and concentrated in vacuo to give a residue, which was purified by preparative TLC (CH$_2$Cl$_2$:MeOH=20:1) to afford compound 12c (60 mg, 43% yield) as a light brown oil. MS 355.0[M+H]$^+$, 357.0[M+H]$^+$.

A mixture of compound 12c (60 mg, 0.169 mmol), morpholin-3-one (17 mg, 0.169 mmol), N$^1$, N$^2$-dimethylethane-1,2-diamine (6 mg, 0.068 mmol), CuI (13 mg, 0.068 mmol) and K$_2$CO$_3$ (47 mg, 0.338 mmol) in 1, 4-dioxane (1.2 mL) was stirred under argon at 100° C. for 16 h. The reaction mixture was filtered and the filtrate was concentrated in vacuo to give a residue, which was purified by preparative TLC (DCM:MeOH=15:1 with 0.08% ammonia solution (28% w/w)) and then preparative TLC (acetone:CH$_3$CN=40:1) to afford compound 12 (4.96 mg, 8% yield) as a light yellow solid. $^1$H NMR (a mixture of diastereomers, CD$_3$OD, 400 Hz): δ 8.05 and 7.85 (two s, 1H), 7.62-7.58 (m, 1H), 7.50-7.23 (m, 7H), 7.19 and 7.09 (two s, 1H), 5.57-5.52 and 5.48-5.43 (two m, 1H), 5.05-4.97 (m, 1H), 4.27 (s, 2H), 4.09-4.01 (m, 2H), 3.79-3.73 (m, 2H), 2.62-2.53, 2.45-2.37 and 2.03-1.94 (three m, 2H); MS 376.2[M+H]$^+$.

EXAMPLE 13

Preparation of (1-(5H-imidazo[5,1-a]isoindol-5-yl)cyclopropyl)(cyclohexyl) methanol (Compound 13)

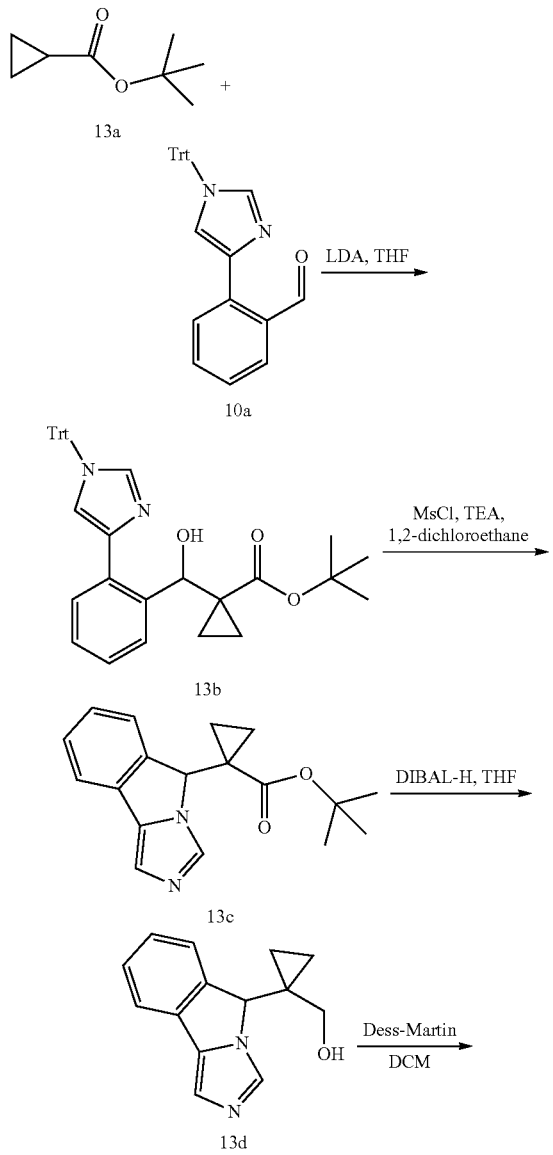

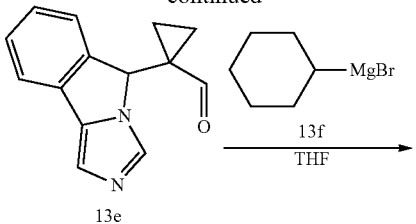

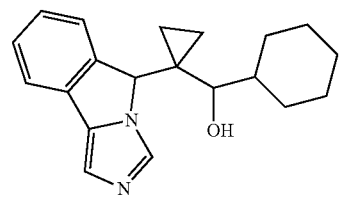

Compound 13

To a solution of 13a (52 mg, 0.363 mmol) in anhydrous THF (5 mL) was added LDA (2 M in THF, 0.2 mL, 0.40 mmol) dropwise at −78° C. under nitrogen. The reaction mixture was stirred at −78° C. for 1 h, a solution of 10a (100 mg, 0.242 mmol) in anhydrous THF (1 mL) was added dropwise. The resulting reaction mixture was warmed slowly to room temperature, and stirred for another 3 h. The reaction mixture was quenched with water and extracted with EtOAc (5 mL×3). The combined organic layers were washed with brine (10 mL), dried over anhydrous Na$_2$SO$_4$, filtered and concentrated in vacuo to give a residue, which was purified by preparative TLC (petroleum ether:EtOAc=4:1) to afford compound 13b (70 mg, 52% yield) as a white solid. $^1$H NMR (CD$_3$OD, 400 MHz): δ 7.62-7.55 (m, 3H), 7.45-7.36 (m, 9H), 7.32-7.20 (m, 8H), 7.15 (s, 1H), 5.65 (s, 1H), 1.15 (s, 9H), 1.01-0.87 (m, 3H), 0.54-0.47 (m, 1H); MS 557.3 [M+H]$^+$.

A mixture of compound 13b (300 mg, 0.539 mmol), methanesulfonyl chloride (123 mg, 1.079 mmol), and TEA (218 mg, 2.158 mmol) in 1,2-dichloroethane (5 mL) was stirred for 16 h at 60° C. The reaction mixture was quenched with water (10 mL) and extracted with EtOAc (5 mL×3). The combined organic layers were washed with brine (10 mL), dried over anhydrous Na$_2$SO$_4$, filtered and concentrated in vacuo to give a residue, which was purified by preparative TLC (CH$_2$Cl$_2$:MeOH=15:1) to afford compound 13c (75 mg, 47% yield) as a light yellow solid. $^1$H NMR (CD$_3$OD, 400 MHz): δ 8.01 (br s, 1H), 7.61 (d, J=7.6 Hz, 1H), 7.51 (d, J=7.6 Hz, 1H), 7.45-7.39 (m, 1H), 7.35-7.29 (m, 1H), 7.22 (br s, 1H), 4.95 (br s, 1H), 1.50-1.25 (m, 4H), 0.98 (s, 9H); MS 297.1 [M+H]$^+$.

A solution of 13c (30 mg, 0.101 mmol) in anhydrous THF (3 mL) was cooled to −78° C. DIBAL-H (1 M in toluene, 0.3 mL, 0.303 mmol) was added dropwise to the mixture. The reaction mixture was stirred at −78° C. for 2 h. The reaction mixture was quenched with MeOH (0.1 mL) and potassium sodium tartrate saturated solution (3 mL) at −78° C., and then was extracted with EtOAc (3 mL×3). The combined organic layers were washed with brine (3 mL), dried over anhydrous Na$_2$SO$_4$, filtered and concentrated in vacuo to give crude compound 13d (20 mg, 87% yield) as a light yellow solid, which was used for the next without further purification. MS 227.2 [M+H]$^+$.

A mixture of compound 13d (20 mg, 0.088 mmol), Dess-Martin periodinane (37 mg, 0.088 mmol) in CH$_2$Cl$_2$ (1 mL) was stirred at room temperature for 1 h. This reaction mixture was purified directly by preparative TLC (CH$_2$Cl$_2$:MeOH=15:1) to afford compound 13e (20 mg, 99% yield) as a white solid. $^1$H NMR (CDCl$_3$, 400 MHz): δ 8.81 (s, 1H), 7.76 (s, 1H), 7.55 (d, J=7.2 Hz, 1H), 7.44-7.37 (m, 1H), 7.31-7.22 (m, 2H), 7.20 (s, 1H), 5.74 (s, 1H), 1.46-1.33 (m, 3H), 0.85-0.76 (m, 1H); MS 225.2 [M+H]$^+$.

To a stirred solution of 13e (20 mg, 0.0.088 mmol) in anhydrous THF (3 mL) was added cyclohexylmagnesium bromide (1 M in THF, 0.35 mL, 0.358 mmol) slowly at 0° C. The mixture was stirred at room temperature for 1 h. The reaction mixture was quenched with NH$_4$Cl saturated solution (3 mL) and extracted with EtOAc (3 mL×3). The combined organic layers were washed with brine (5 mL), dried over anhydrous Na$_2$SO$_4$, filtered and concentrated in vacuo to give a residue, which was purified by preparative TLC (CH$_2$Cl$_2$:MeOH=15:1) to afford compound 13 (5.53 mg, 20% yield) as a light brown solid. $^1$H NMR (a mixture of diastereomers, CD$_3$OD, 400 MHz): δ 8.12 and 7.99 (two s, 1H), 7.62-7.57 (m, 1.2H), 7.47-7.28 (m, 2.8H), 7.17 and 7.13 (two s, 1H), 5.29 and 4.93 (two s, 1H), 3.10 and 2.78 (two d, 1=7.6 Hz, 4.0 Hz, 1H), 2.00-1.96 (m, 0.8H), 1.80-1.44 (m, 4.2H), 1.30-0.63 (m, 10H); MS 309.3 [M+H]$^+$.

EXAMPLE 14

Preparations of (1s,3r,5R,7S)-3-(1-hydroxy-2-(5H-imidazo[5,1-a]isoindol-5-yl)ethyl)adamantan-1-ol (Compound 14f) and (1R,3S,5r,7r)-5-(1-hydroxy-2-(5H-imidazo[5,1-a]isoindol-5-yl)ethyl)adamantane-1,3-diol (Compound 14e)

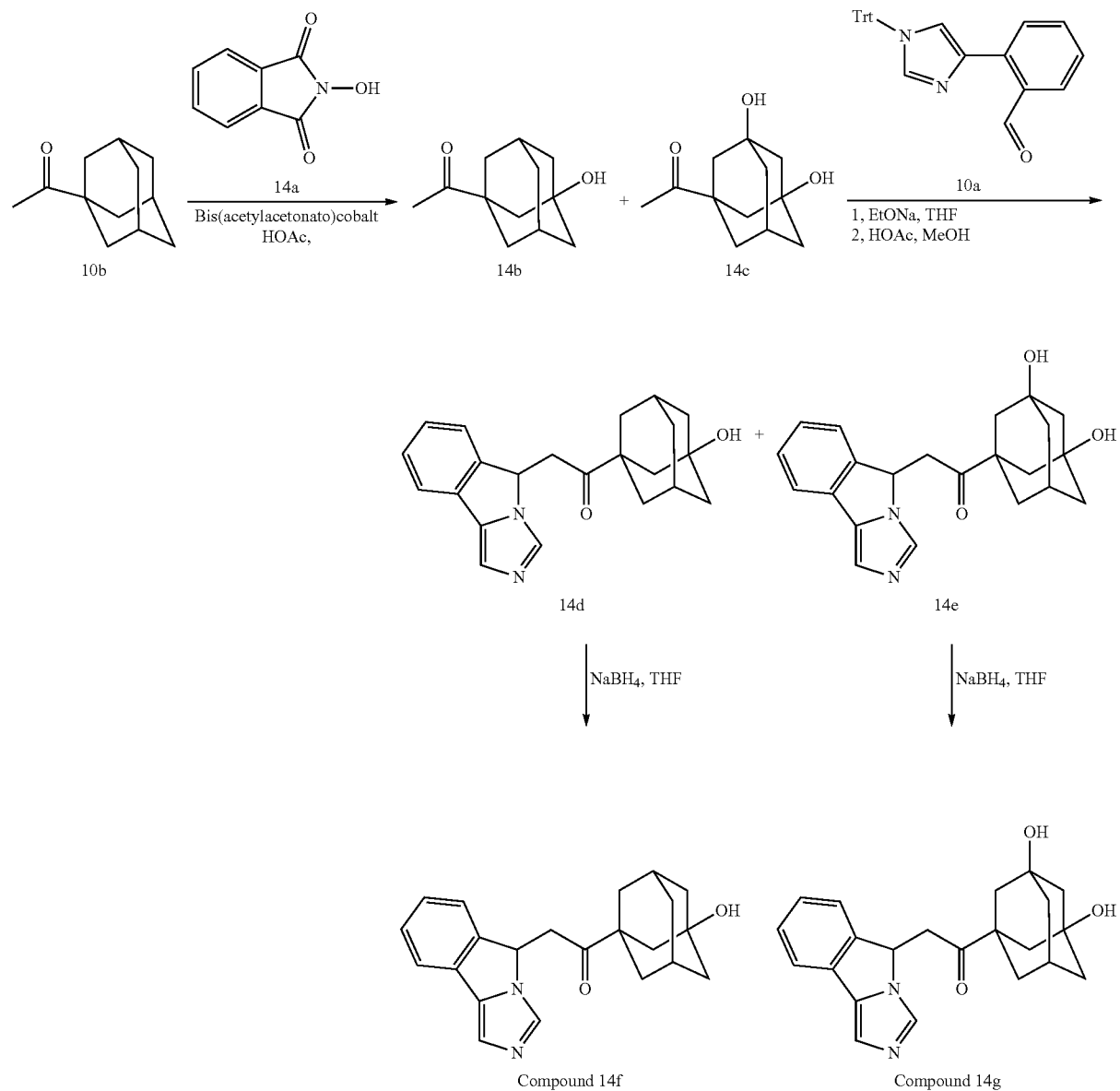

A mixture of 10b (210 mg, 1.180 mmol), 2-hydroxyisoindoline-1,3-dione (38 mg, 0.233 mmol), Bis(acetylacetonato) cobalt (30 mg, 0.117 mmol) in HOAc (5 mL) was stirred under oxygen atmosphere at 75° C. for 6 h. The reaction mixture was concentrated to dryness under reduced pressure. The residue was diluted with EtOAc (10 mL) and the insoluble solid was filtered off. The filtrate was concentrated in vacuo to afford a crude mixture of 14b and 14c (160 mg) as slight brown oil, which was used for the next step without further purification.

To a stirred mixture of compound 10a (150 mg, 0.362 mmol) and compounds 14b and 14c (70 mg, 0.362 mmol) in anhydrous THF (10 mL) was added dropwise a solution of EtONa (21% in EtOH, 152 mg, 0.471 mmol) at room temperature. The reaction mixture was stirred at room temperature for 1.5 h. After the mixture was concentrated to dryness under reduced pressure, the residue was diluted with $NH_4Cl$ solution (10 mL) and extracted with EtOAc (10 mL×3). The combined organic layers were washed with brine (10 mL), dried over anhydrous $Na_2SO_4$, filtered and concentrated in vacuo to give a residue, which was dissolved in MeOH (8 mL). To this solution was added HOAc (2 mL), and the reaction mixture was stirred at 60° C. for 2 h. The mixture was concentrated in vacuo to give a residue, which was diluted with $NaHCO_3$ saturated solution (10 mL) and extracted with EtOAc (10 mL×3). The combined organic layers were washed with brine (10 mL), dried over anhydrous $Na_2SO_4$, filtered and concentrated in vacuo to give a residue, which was purified by preparative TLC (EtOAc) to afford compound 14d (70 mg, 55% yield), MS 349.2[M+H]$^+$, and 14e (40 mg, 31% yield) as a light yellow solid, MS Found 365.2[M+H]$^+$.

To a stirred solution of compound 14d (66 mg, 0.189 mmol) in anhydrous THF (5 mL) was added $NaBH_4$ (22 mg, 0.567 mmol) at 0° C. Then the mixture was stirred and warmed to room temperature for 2 h. The mixture was quenched with ice cold aqueous $NH_4Cl$ solution (5 mL) and extracted with EtOAc (5 mL×3). The combined organic layers were washed with brine (5 mL), dried over anhydrous $Na_2SO_4$, filtered and concentrated in vacuo to give a residue, which was purified by preparative TLC ($CH_2Cl_2$:MeOH=20:1) to afford compound 14f (23.6 mg, 36% yield) as a light yellow solid. $^1$H NMR (a mixture of diastereomers, DMSO-$d_6$, 400 MHz): δ 7.95 and 7.92 (two s, 1H), 7.60 (d, J=7.6 Hz, 1H), 7.57 (d, J=7.6 Hz, 1H), 7.38 (dd, J=7.6 Hz, 7.2 Hz, 1H), 7.27 (dd, J=7.6 Hz, 7.6 Hz, 1 H), 7.14 and 7.11 (two s, 1H), 5.41-5.33 (m, 1H), 4.97 and 4.92 (two d, J=6.4 Hz and J=6.4 Hz, 1H), 4.31 (s, 1H), 3.44-3.38(m, 1H), 2.17-2.02 (m, 3H), 1.79-1.71 (m, 1H), 1.55-1.31 (m, 12H); MS 351.2[M+H]$^+$.

Four enantiomereric compounds 14f-1, 14f-2, 14f-3 and 14f-4 were obtained by the separation of 14f on waters preparative SFC-80 under the following conditions: CHIRALCEL OD column, 30×250 mm, 5 μm; mobile phase: solvent A is $CO_2$, co-solvent B is 15% MeOH with 0.1% DEA; detection wavelength: 272 nm; column temperature: 35° C. Analytical chiral SFC conditions: CHIRALCEL OD column, 4.6×100 mm, 3 μm; mobile phase: solvent A is $CO_2$, co-Solvent B is 18% MeOH with 0.1% DEA; detection wavelength: 270 nm; column temperature: 35° C. Compound 14f-1: MS 351.2 [M+H]$^+$, RT=3.23 min. Compound 14f-2: MS 351.2 [M+H]$^+$, RT=3.76 min. Compound 14f-3: $^1$H NMR (CDCl$_3$, 400 MHz): δ 7.82 (s, 1H), 7.55 (d, J=7.6 Hz, 1H), 7.42 (d, J=7.6 Hz, 1H), 7.38 (dd, J=7.6 Hz, 7.6 Hz, 1H), 7.25 (dd, J=7.2 Hz, 7.2 Hz, 1 H), 7.18 (s, 1H), 5.36 (t, J=5.6 Hz, 1H), 3.46-3.41 (m, 1H), 2.24 (br s, 2H), 2.16-2.10 (m, 2H), 1.74-1.40 (m, 12H); MS 351.2 [M+H]$^+$, RT=4.14 min. Compound 14f-4: $^1$H NMR (CDCl$_3$, 400 MHz): δ 7.83 (s, 1H), 7.55 (d, J=8.0 Hz, 1H), 7.42 (d, J=7.6 Hz, 1H), 7.38 (dd, J=7.6 Hz, 7.6 Hz, 1H), 7.25 (dd, J=8.0 Hz, 8.0 Hz, 1 H), 7.18 (s, 1H), 5.36 (t, J=5.6 Hz, 1H), 3.46-3.40 (m, 1H), 2.24 (br s, 2H), 2.17-2.10 (m, 2H), 1.74-1.40 (m, 12H); MS 351.2 [M+H]$^+$, RT=4.72 min.

To a stirred solution of compound 14e (40 mg, 0.110 mmol) in anhydrous THF (5 mL) was added $NaBH_4$ (13 mg, 0.330 mmol) at 0° C. The mixture was warmed to room temperature and stirred for 2 h. The mixture was quenched with ice cold aqueous $NH_4Cl$ solution (5 mL) and extracted with EtOAc (5 mL×3). The combined organic layers were washed with brine (5 mL), dried over anhydrous $Na_2SO_4$, filtered and concentrated in vacuo to give a residue, which was purified by preparative TLC ($CH_2Cl_2$:MeOH=15:1) to afford compound 14g (21.9 mg, 54% yield) as a light yellow solid. $^1$H NMR (a mixture of diastereomers, DMSO-$d_6$, 400 MHz): δ 7.95 and 7.93 (two s, 1H), 7.60 (d, J=7.6 Hz, 1H), 7.57 (d, J=7.6 Hz, 1H), 7.38 (dd, J=7.6 Hz, 7.2 Hz, 1H), 7.27 (ddd, J=7.6 Hz, 7.6 Hz, 0.8 Hz, 1 H), 7.14 and 7.12 (two s, 1H), 5.42-5.33 (m, 1H), 5.02 and 4.98 (two d, J=6.4 Hz and I=6.4 Hz, 1H), 4.41 (s, 2H), 3.50-3.43 (m, 1H), 2.14 (s, 1H), 2.10-2.00 (m, 1H), 1.78-1.72 (m, 1H), 1.48-1.17 (m, 12H); MS 367.3 [M+H]$^+$.

EXAMPLE 15

Preparations of (1s,3r,5R,7S)-3-(2-(6-fluoro-5H-imidazo[5,1-a]isoindol-5-yl)-1-hydroxyethyl)adamantan-1-ol (Compound 15d) and 1-((3r,5r,7r)-adamantan-1-yl)-2-(6-fluoro-5H-imidazo[5,1-a]isoindol-5-yl)ethanol (Compound 15e)

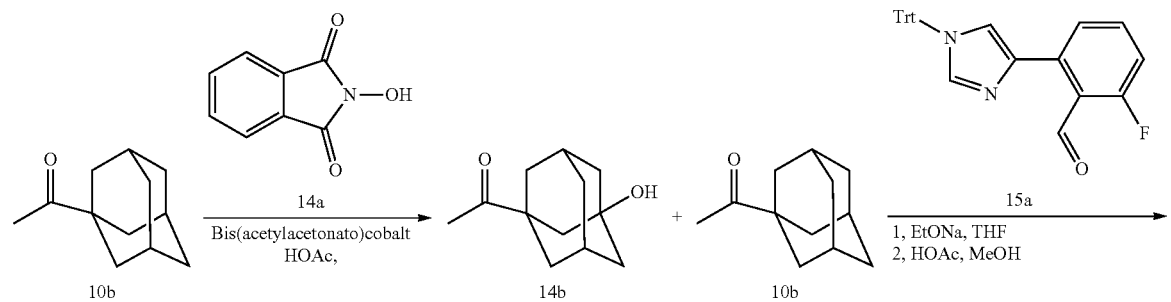

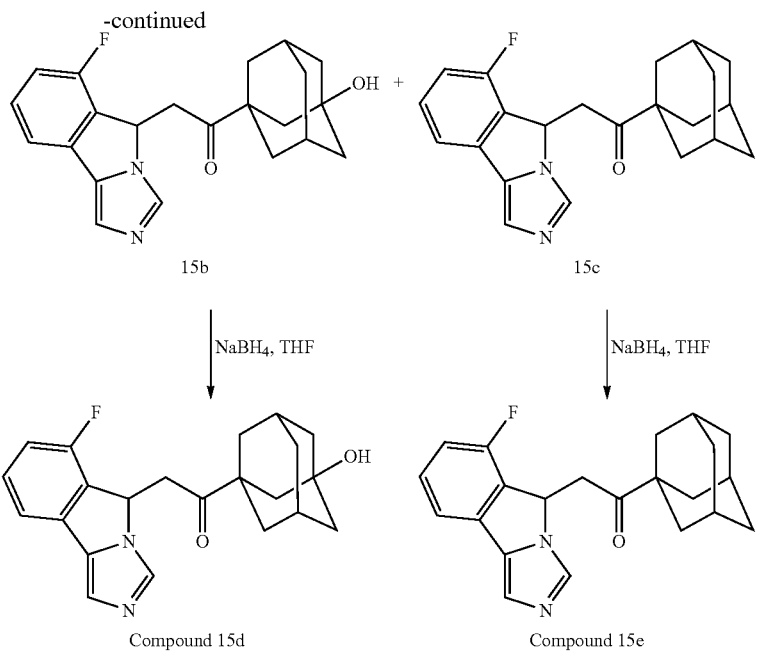

Compound 15d  Compound 15e

A mixture of 10b (200 mg, 1.124 mmol), 2-hydroxyisoindoline-1,3-dione (73 mg, 0.449 mmol), Bis(acetylacetonato) cobalt (58 mg, 0.225 mmol) in HOAc (5 mL) was stirred under $O_2$ atmosphere at 75° C. for 6 h. The reaction mixture was concentrated under reduced pressure. The residue was diluted with EtOAc (20 mL), and the mixture was filtered. The filtrate was concentrated in vacuo to afford a crude mixture of 10b and 14b (140 mg) as slight yellow oil, which was used to the next step without further purification.

To a stirred mixture of compound 15a (97 mg, 0.224 mmol) and compounds 14b and 10b (43 mg, 0.224 mmol) in anhydrous THF (10 mL) was added dropwise a solution of EtONa (21% in EtOH, 94 mg, 0.291 mmol) at room temperature. The reaction mixture was stirred at room temperature for 0.5 h. The mixture was concentrated to dryness under reduced pressure, the residue was diluted with $NH_4Cl$ solution and extracted with EtOAc (10 mL×3). The combined organic layers were washed with brine (10 mL), dried over anhydrous $Na_2SO_4$, filtered and concentrated in vacuo to give a residue, which was dissolved in MeOH (15 mL). To this solution was added HOAc (3 mL), and the reaction mixture was stirred at 60° C. for 1.5 h. The mixture was concentrated in vacuo to give a residue, which was dissolved in $NaHCO_3$ saturated solution and extracted with EtOAc (10 mL×3). The combined organic layers were washed with brine (10 mL), dried over anhydrous $Na_2SO_4$, filtered and concentrated in vacuo to give a residue, which was purified by preparative TLC (EtOAc) to afford compound 15b (27 mg, 33% yield), MS Found: 367.2 $[M+H]^+$; and 15c (18 mg, 22% yield) as a white solid, MS Found: 351.2 $[M+H]^+$.

To a stirred solution of compound 15b (27 mg, 0.074 mmol) in anhydrous THF (5 mL) was added $NaBH_4$ (8.4 mg, 0.221 mmol) at 0° C. The mixture was warmed to room temperature and stirred for 2.5 h. The mixture was quenched with ice cold aqueous $NH_4Cl$ solution (10 mL) and extracted with EtOAc (5 mL×3). The combined organic layers were washed with brine (10 mL), dried over anhydrous $Na_2SO_4$, filtered and concentrated in vacuo to give a residue, which was purified by preparative TLC (EtOAc) to afford compound 15d (6 mg, 22% yield) as a white solid. $^1$H NMR (a mixture of diastereomers, $CD_3OD$, 400 MHz): δ 8.01 (s, 1H), 7.47-7.38 (m, 2H), 7.16 (s, 1H), 7.07-6.98 (m, 1H), 5.56 (t, J=4.8 Hz, 1H), 3.20 (d, J=10.0 Hz, 1H), 2.51-2.43 (m, 1H), 2.17 (s, 2H), 2.04-1.94 (m, 1H), 1.72-1.52 (m, 6H), 1.50-1.40 (m, 6H), MS 369.2 $[M+H]^+$.

To a stirred solution of compound 15c (18 mg, 0.051 mmol) in THF (5 mL) was added $NaBH_4$ (5.9 mg, 0.154 mmol) at 0° C. The mixture was warmed to room temperature and stirred for 2 h. The mixture was quenched with ice cold aqueous $NH_4Cl$ solution (10 mL) and extracted with EtOAc (5 mL×3). The combined organic layers were washed with brine (10 mL), dried over anhydrous $Na_2SO_4$, filtered and concentrated in vacuo to give a residue, which was purified by preparative TLC (EtOAc) to afford compound 15e (6.8 mg, 38% yield) as a white solid. $^1$H NMR (a mixture of diastereomers, DMSO-$d_6$, 400 MHz): δ 7.95 (s, 1H), 7.44-7.38 (m, 2H), 7.15 (s, 1H), 7.10-7.04 (m, 1H), 5.55 (t, J=4.8 Hz, 1H), 4.54 (d, J=6.4 Hz, 1H), 3.04-2.98 (m,, 1H), 2.38-2.31 (m, 1H), 1.91 (s, 3H), 1.87-1.77 (m, 1H), 1.68-1.40 (m, 12H); MS 353.2 $[M+H]^+$.

Enantiomereric compounds 15d-1, 15d-2, 15d-3 and 15d-4 were obtained by the separation of 15d on waters preparative SFC-80 under the following conditions: CHIRALPAK AD column, Daicel, 30×250 mm, 5 μm; mobile phase: solvent A is $CO_2$, co-solvent B is 30% EtOH with 0.1% DEA; detection wavelength: 273 nm; column temperature: 35° C. Analytical chiral SFC conditions: CHIRALPAK AD column, Daicel, 4.6×100 mm, 3 μm; mobile phase: solvent A is $CO_2$, co-Solvent B is 30% EtOH with 0.1% DEA; detection wavelength: 273 nm; column temperature: 35° C. Compound 15d-1: $^1$H NMR (CDCl$_3$, 400 MHz): δ 7.85 (s, 1H), 7.40-7.30 (m, 2H), 7.21 (s, 1H), 6.95 (dd, J=8.4 Hz, 8.4 Hz, 1H), 5.64 (d, J=8.4 Hz, 1H), 3.49 (d, J=11.6 Hz, 1H), 2.50-2.40 (m, 1H), 2.25 (br s, 2H), 1.80-1.39 (m, 13H); MS 369.2 $[M+H]^+$; RT=3.95 min. Compound 15d-2: $^1$H NMR (CDCl$_3$, 400 MHz): δ 7.86 (s, 1H), 7.38-7.30 (m, 2H), 7.19 (s, 1H), 6.96-6.91 (m, 1H), 5.47 (t, J=4.4 Hz, 1H), 3.34 (d, J=10.0 Hz, 1H), 2.41-2.35 (m, 1H), 2.24 (brs, 2H), 2.13-2.05 (m, 1H), 1.71-1.40 (m, 12H); MS 369.2 [M+H]+; RT=4.42 min. Compound 15d-3: ¹H NMR (CDCl₃, 400 MHz): δ 7.86 (s, 1H), 7.38-7.30 (m, 2H), 7.18 (s, 1H), 6.96-6.91 (m, 1H), 5.47 (t, J=4.8 Hz, 1H), 3.34 (d, J=9.6 Hz, 1H), 2.42-2.35 (m, 1H), 2.24 (brs, 2H), 2.13-2.05 (m, 1H), 1.71-1.40 (m, 12H); MS 369.2 [M+H]+; RT=5.07 min. Compound 15d-4: ¹H NMR (CDCl₃, 400 MHz): δ 7.87 (s, 1H), 7.40-7.30 (m, 2H), 7.21 (s, 1H), 6.95 (dd, J=8.8 Hz, 8.4 Hz, 1H), 5.64 (d, J=8.4 Hz, 1H), 3.49 (d, J=11.2 Hz, 1H), 2.50-2.40 (m, 1H), 2.24 (br s, 2H), 1.80-1.39 (m, 13H); MS 369.2 [M+H]+; RT=6.18 min.

EXAMPLE 16

Preparation of 4-(2-(6-fluoro-5H-imidazo[5,1-a]isoindol-5-yl)-1-hydroxyethyl)bicyclo[2.2.2]octan-1-ol (Compound 16)

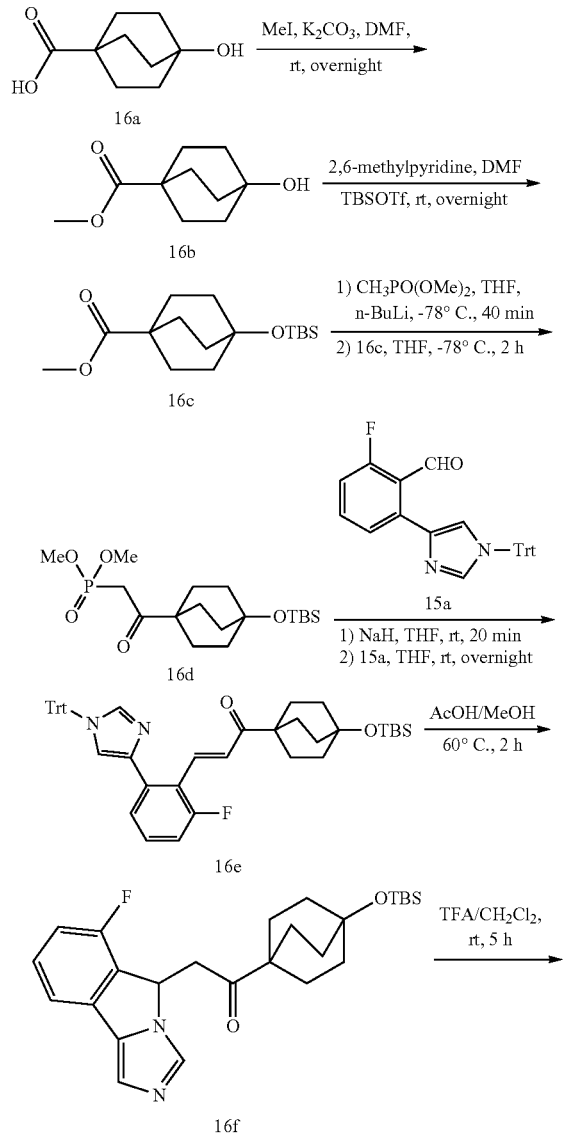

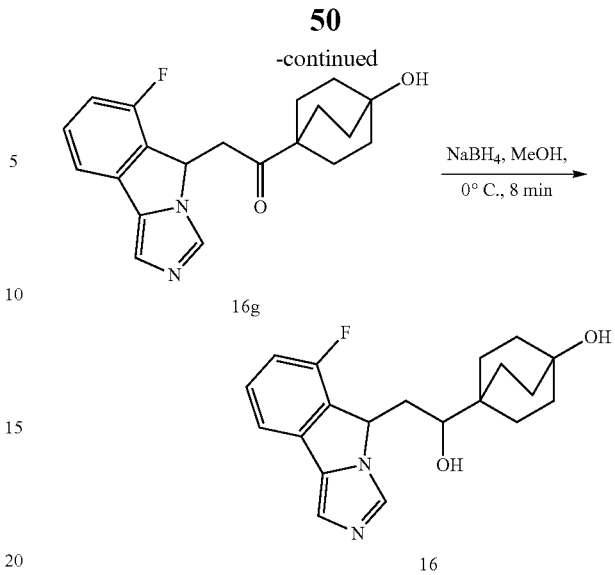

To a mixture of compound 16a (1.2 g, 7.05 mmol) and K₂CO₃ (1.5 g, 10.85 mmol) in DMF (20 mL) was added MeI (1.5 g, 10.57 mmol) dropwise over 5 min. The mixture was stirred at room temperature overnight, quenched with water (20 mL) and extracted with EtOAc (30 mL×3). The combined organic layers were washed with brine (30 mL), dried over anhydrous Na₂SO₄, filtered and concentrated in vacuo to afford crude compound 16b (1.2 g, 92% yield) as a yellow solid, which was used to the next step without further purification. ¹H NMR (DMSO-d₆, 400 MHz): δ 4.34 (s, 1H), 3.55 (s, 3H), 1.81-1.75 (m, 6H), 1.53-1.48 (m, 6H).

To a mixture of compound 16b (1.2 g, 6.51 mmol) and 2,6-dimethylpyridine (2.1 g, 19.60 mmol) in DMF (15 mL) was added TBSOTf (5.2 g, 19.67 mmol). The mixture was stirred at room temperature overnight, quenched with water (20 mL) and extracted with EtOAc (30 mL×3). The combined organic layers were washed with brine (30 mL), dried over anhydrous Na₂SO₄, filtered and concentrated in vacuo to give the residue, which was purified by column chromatography (petroleum ether:EtOAc=50:1) to afford compound 16c (1.5 g, 77% yield) as a yellow oil. ¹H NMR (CDCl₃, 400 MHz): δ 3.62 (s, 3H), 1.90-1.85 (m, 6H), 1.68-1.62 (m, 6H), 0.82 (s, 9H), 0.04 (s, 6H).

To a solution of dimethyl methylphosphonate (209 mg, 1.68 mmol) in THF (6 mL) was added n-BuLi (2.5 M in hexane, 0.84 mL, 2.10 mmol) dropwise at -78° C., then the mixture was stirred at -78° C. for 40 min. To the resulting mixture was added a solution of compound 16c (250 mg, 0.84 mmol) in THF (1 mL) at -78° C. The mixture was stirred at -78° C. for 2 h, then quenched with aqueous NH₄Cl solution (10 mL) and extracted with EtOAc (20 mL×3). The combined organic layers were washed with brine (20 mL), dried over anhydrous Na₂SO₄, filtered and concentrated in vacuo to afford crude compound 16d (300 mg, 92% yield) as a yellow oil, which was used to the next step without further purification. ¹H NMR (CDCl₃, 400 MHz): δ 3.79 (s, 3H), 3.77 (s, 3H), 3.14 (s, 1H), 3.08 (s, 1H), 1.87-1.81 (m, 6H), 1.71-1.65 (m, 6H), 0.83 (s, 9H), 0.04 (s, 6H).

To a solution of compound 16d (300 mg, 0.77 mmol) in THF (6 mL) was added NaH (60% in mineral oil, 62 mg, 1.55 mmol) and the mixture was stirred at room temperature for 20 min. To the above mixture was added compound K-3-2 (332 mg, 0.77 mmol) slowly over 5 min, and the temperature of the mixture was kept below 5° C. The mixture was stirred at room temperature overnight, quenched with iced aqueous NH₄Cl solution (20 mL) and extracted with EtOAc (25 mL×3). The combined organic layers were washed with brine (20 mL), dried over anhydrous Na₂SO₄, filtered and concentrated in vacuo to give the residue, which was purified by column chromatography (petrol ether:EtOAc=8:1) to afford compound 16e (400 mg, 74% yield) as a yellow solid. ¹H NMR (CDCl₃, 400 MHz): δ 7.72 (d, J=12.0 Hz, 1H), 7.57 (d, J=8.0 Hz, 1H), 7.50 (s, 1H), 7.39-7.26 (m, 10H), 7.20-7.16 (m, 6H), 7.10-6.97 (m, 2H), 6.88 (s, 1H). 1.84-1.78 (m, 6H), 1.71-1.65 (m, 6H), 0.83 (s, 9H), 0.06 (s, 6H).

A solution of compound 16e (400 mg, 0.57 mmol) in MeOH (10 mL) and AcOH (2.5 mL) was stirred at 60° C. for 2 h. The reaction mixture was cooled to room temperature, concentrated in vacuo to dryness. The residue was diluted with aqueous Na₂CO₃ solution (30 mL) and extracted with EtOAc (30 mL×3). The combined organic layers were washed with brine (30 mL), dried over anhydrous Na₂SO₄, filtered and concentrated in vacuo to give the residue, which was purified by column chromatography (petroleum ether:EtOAc=8:1) to afford crude compound 16f (220 mg, 84% yield) as a yellow solid. MS 455.2 [M+H]⁺.

A mixture of compound 16f (172 mg, 0.375 mmol) in CH₂Cl₂ (4 mL) and TFA (1 mL) was stirred at room temperature overnight. The reaction mixture was cooled to room temperature, concentrated in vacuo to remove the solvent. The residue was diluted with aqueous Na₂CO₃ solution (20 mL) and extracted with EtOAc (20 mL×3). The combined organic layers were washed with brine (20 mL), dried over anhydrous Na₂SO₄, filtered and concentrated in vacuo to give the residue, which was purified by preparative TLC (CH₂Cl₂/MeOH=15/1) to afford compound 16g (75 mg, 59% yield) as a yellow solid. ¹H NMR (CDCl₃, 400 MHz): δ 7.55 (s, 1H), 7.40-7.28 (m, 2H), 7.18 (s, 1H), 6.94 (dd, J=9.2 Hz, 8.4 Hz, 1H), 5.74 (d, J=9.6 Hz, 1H), 3.49 (s, 1H), 3.43 (dd, J=18.8 Hz, 2.0 Hz, 1H), 2.80 (dd, J=18.4 Hz, 10.4 Hz, 1H), 1.91-1.82 (m, 6H), 1.72-1.66 (m, 6H); MS 341.2 [M+H]⁺.

To a solution of compound 16g (46 mg, 0.135 mmol) in MeOH (3 mL) was added NaBH₄ (16 mg, 0.423 mmol) at 0° C. The mixture was stirred at 0° C. for 8 min., quenched with aqueous NH₄Cl solution (10 mL) and extracted with EtOAc (10 mL×3). The combined organic layers were washed with brine (10 mL), dried over anhydrous Na₂SO₄, filtered and concentrated in vacuo to give the residue, which was purified by preparative TLC (CH₂Cl₂:MeOH=10:1) to afford compound 16 (34 mg, 73% yield) as a white solid. ¹H NMR (DMSO-d₆, 400 MHz): δ 7.97, and 7.95 (two s, 1H), 7.47-7.37 (m, 2H), 7.21 and 7.17 (two s, 1H), 7.13-7.04 (m, 1H), 5.63-5.57 and 5.55-5.50 (two m, 1H), 4.95 and 4.51 (two d, J=6.4 Hz, 1H), 4.17 (s, 1H), 3.18-3.08 (m, 1H), 2.35-2.20 (m, 1H), 1.83-1.73 (m, 1H), 1.50-1.31 (m, 12H); MS 343.2 [M+H]⁺.

Four enantiomereric compounds 16-1, 16-2, 16-3 and 16-4 were obtained by the separation of compound 16 on waters prep SFC-80 under the following conditions: CHIRALCEL OJ column, Daicel, 30×250 mm, 5 μm; mobile phase: solvent A is CO₂, co-solvent B is 15% EtOH with 0.1% DEA; detection wavelength: 272 nm; column temperature: 35° C. Analytical chiral SFC conditions: CHIRALCEL OJ column, Daicel, 4.6×100 mm, 3 μm; mobile phase: solvent A is CO₂, co-Solvent B is 20% EtOH with 0.1% DEA; detection wavelength: 273 nm; column temperature: 35° C. Compound 16-1: ¹H NMR (CDCl₃, 400 MHz): δ 7.82 (s, 1H), 7.38-7.29 (m, 2H), 7.20 (s, 1H), 6.95-6.90 (m, 1H), 5.61 (d, J=8.8 Hz, 1H), 3.53 (d, J=10.8 Hz, 1H), 2.43-2.33 (m, 1H), 2.10-1.97 (m, 1H), 1.74-1.45 (m, 12H); MS 343.2 [M+H]⁺; RT=2.16 min. Compound 16-2: ¹H NMR (CDCl₃, 400 MHz): δ 7.83 (s, 1H), 7.37-7.29 (m, 2H), 7.18 (s, 1H), 6.96-6.90 (m, 1H), 5.44 (t, J=4.8 Hz, 1H), 3.41 (d, J=10.4 Hz, 1H), 2.35-2.27 (m, 1H), 2.06-1.97 (m, 1H), 1.74-1.43 (m, 12H); MS 343.2 [M+H]⁺; RT=2.89 min. Compound 16-3: ¹H NMR (CDCl₃, 400 MHz): δ 7.86 (s, 1H), 7.39-7.29 (m, 2H), 7.18 (s, 1H), 6.95-6.90 (m, 1H), 5.44 (t, J=4.8 Hz, 1H), 3.42 (d, J=9.6 Hz, 1H), 2.35-2.27 (m, 1H), 2.06-1.97 (m, 1H), 1.76-1.43 (m, 12H); MS 343.2 [M+H]⁺; RT=3.31 min. Compound 16-4: ¹H NMR (CDCl₃, 400 MHz): δ 7.82 (s, 1H), 7.39-7.30 (m, 2H), 7.20 (s, 1H), 6.94 (dd, J=9.2 Hz, 8.4 Hz, 1H), 5.61 (d, J=8.4 Hz, 1H), 3.53 (d, J=10.8 Hz, 1H), 2.43-2.33 (m, 1H), 2.10-1.97 (m, 1H), 1.73-1.46 (m, 12H); MS 343.2 [M+H]⁺; RT=4.46 min.

EXAMPLE 17

Preparation of (1R,2s,3S,5s,7s)-5-(2-(6-fluoro-5H-imidazo[5,1-a]isoindol-5-yl)-1-hydroxyethyl)adamantan-2-ol (Compound 17)

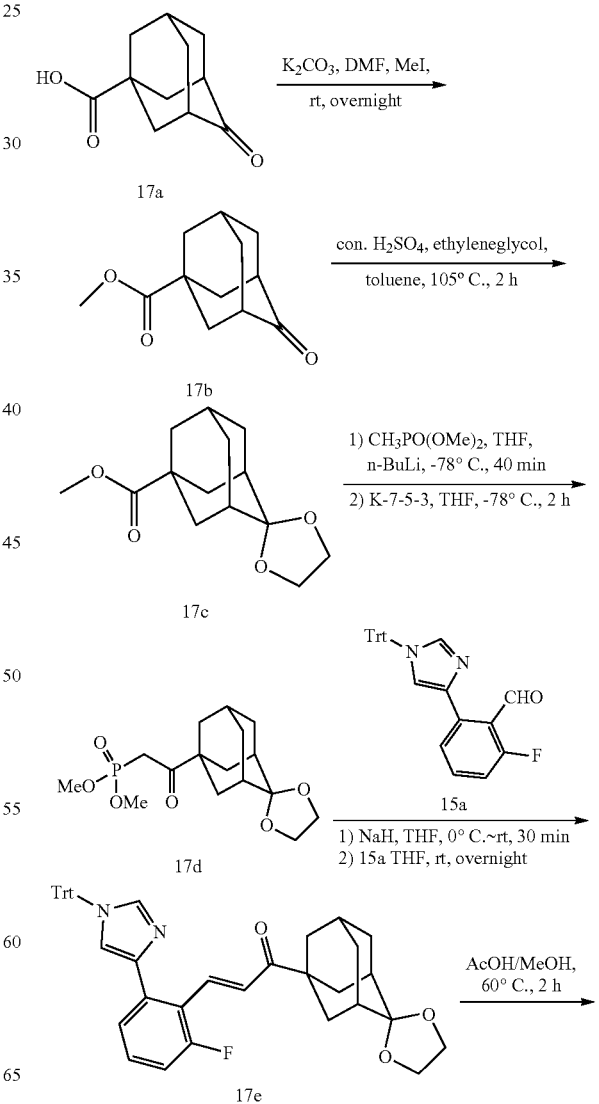

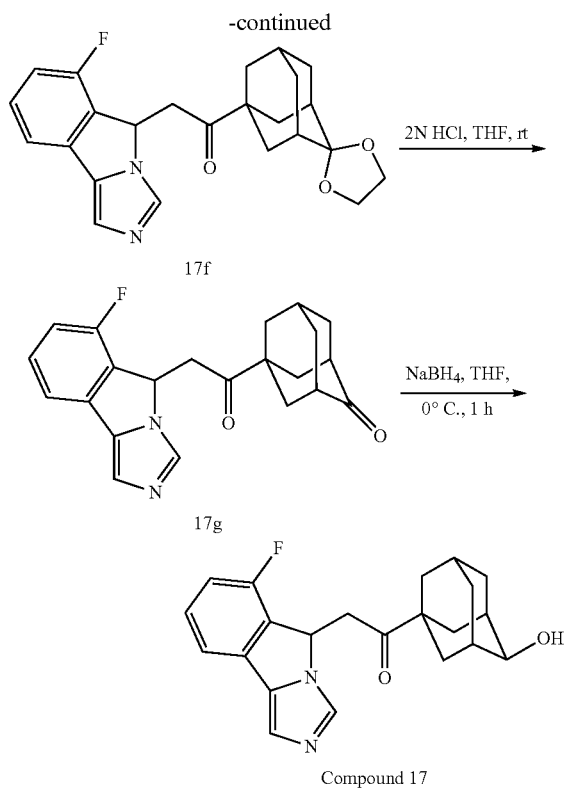

con. = concentrated.

To a mixture of compound 17a (1.0 g, 5.15 mmol) and K₂CO₃ (1.1 g, 7.96 mmol) in DMF (10 mL) was added MeI (1.1 g, 7.75 mmol) at room temperature. The mixture was stirred at room temperature overnight, diluted with water (30 mL) and extracted with EtOAc (30 mL×3). The combined organic layers were washed with brine (30 mL), dried over anhydrous Na₂SO₄, filtered and concentrated in vauco to afford compound 17b (1.05 g, 98% yield) as a yellow solid, which was used for the next step without further purification. $^1$H NMR (CDCl₃, 400 MHz): δ 3.69 (s, 3H), 2.64-2.55 (m, 2H), 2.25-2.16 (m, 5H), 2.15-1.93 (m, 6H).

To a mixture of compound 17b (400 mg, 1.92 mmol) and ethyleneglycol (653 mg, 10.52 mmol) in toluene (6 mL) was added sulfuric acid (38 mg, 0.38 mmol) at room temperature. The mixture was stirred at 105° C. for 2 h, cooled to room temperature, quenched with aqueous Na₂CO₃ solution (20 mL) and extracted with EtOAc (20 mL×3). The combined organic layers were washed with brine (20 mL), dried over anhydrous Na₂SO₄, filtered and concentrated in vacuo to afford compound 17c (390 mg, 81% yield) as a yellow oil, which was used for the next step without further purification. $^1$H NMR (CDCl₃, 400 MHz): δ 3.95 (s, 4H), 3.64 (s, 3H), 2.21-2.14 (m, 2H), 2.00-1.95 (m, 3H), 1.90-1.78 (m, 6H), 1.66-1.59 (m, 2H).

To a solution of dimethyl methylphosphonate (385 mg, 3.10 mmol) in THF (6 mL) was added n-BuLi (2.5 M in hexane, 1.6 mL, 4.00 mmol) dropwise at −78° C., then the mixture was stirred at −78° C. for 40 min. To the above mixture was added a solution of compound 17c (390 mg, 1.55 mmol) in THF (1 mL) at −78° C. Then the mixture was stirred at −78° C. for 2 h, then was quenched with aqueous NH₄Cl solution (20 mL) and extracted with EtOAc (20 mL×3). The combined organic layers were washed with brine (20 mL), dried over anhydrous Na₂SO₄, filtered and concentrated in vacuo to afford crude compound 17d (430 mg, 81% yield) as a yellow oil, which was used to the next step without further purification. $^1$H NMR (CDCl₃, 400 MHz): δ 3.98-3.92 (m, 4H), 3.80 (s, 3H), 3.78 (s, 3H), 3.80 (s, 3H), 3.18 (s, 1H), 3.12 (s, 1H), 2.17-2.09 (m, 2H), 2.03-1.59 (m, 11H).

To a solution of compound 17d (400 mg, 1.16 mmol) in THF (10 mL) was added NaH (60% in mineral oil, 93 mg, 2.33 mmol) at 0° C. The mixture was stirred at room temperature for 20 min. To the above mixture was added compound 15a (501 mg, 1.16 mmol) slowly over 5 min, and kept the temperature of the mixture below 5° C. The mixture was stirred at room temperature overnight, quenched with iced aqueous NH₄Cl solution (20 mL) and extracted with EtOAc (30 mL×3). The combined organic layers were washed with brine (30 mL), dried over anhydrous Na₂SO₄, filtered and concentrated in vacuo to give the residue, which was purified by column chromatography (CH₂Cl₂:EtOAc=6:1) to afford compound 17e (600 mg, 79% yield) as a gray solid. $^1$H NMR (CDCl₃, 400 MHz): δ 7.74 and 7.70 (two s, 1H), 7.61 (d, J=8.0 Hz, 1H), 7.51 (d, J=1.2 Hz, 1H), 7.39-7.30 (m, 10H), 7.24-7.15 (m, 7H), 7.05-6.98 (m, 1H), 6.91-6.86 (m, 1H), 3.97 (s, 4H), 2.15-2.10 (m, 2H), 2.02-1.97 (m, 3H), 1.93-1.88 (m, 2H), 1.79-1.75 (m, 2H), 1.73-1.60 (m, 4H).

A solution of compound 17e (350 mg, 0.54 mmol) in MeOH:AcOH (10 mL:2.5 mL) was stirred at 60° C. for 2 h, then the mixture was concentrated in vacuo to dryness. The residue was diluted with aqueous Na₂CO₃ solution (30 mL) and extracted with EtOAc (30 mL×3). The combined organic layers were washed with brine (30 mL), dried over anhydrous Na₂SO₄, filtered and concentrated in vacuo to afford crude compound 17f (190 mg, 87% yield) as a yellow solid, which was used for the next step without further purification. MS 409.3 [M+H]⁺.

To a solution of compound 17f (100 mg, 0.24 mmol) in THF (3 mL) was added 2 N HCl (3 mL). The mixture was stirred at room temperature overnight, and concentrated in vacuo to dryness. The residue was diluted with aqueous Na₂CO₃ solution (20 mL) and extracted with EtOAc (15 mL×3). The combined organic layers were washed with brine (20 mL), dried over anhydrous Na₂SO₄, filtered and concentrated in vacuo to give the residue, which was purified by preparative TLC (CH₂Cl₂:MeOH=20:1) to afford compound 17g (75 mg, 88% yield) as a yellow solid. $^1$H NMR (CDCl₃, 400 MHz): δ 7.57 (s, 1H), 7.42-7.31 (m, 2H), 7.19 (s, 1H), 6.94 (ddd, J=8.8 Hz, 8.8 Hz, 0.8 Hz, 1H), 5.77 (d, J=9.6 Hz, 1H), 3.52-3.44 (m, 1H), 2.85 (dd, J=18.4 Hz, 10.6 Hz, 1H), 2.66-2.62 (m, 2H), 2.26-2.22 (m, 1H), 2.20-2.14 (m, 4H), 2.06-1.98 (m, 6H). MS 365.3 [M+H]⁺.

To a solution of compound 17g (75 mg, 0.21 mmol) in THF (2 mL) was added NaBH₄ (47 mg, 1.24 mmol) in portions at 0° C. Then the mixture was stirred at 0° C. for 1 h, quenched with aqueous NH₄Cl solution (10 mL) and extracted with EtOAc (10 mL×3). The combined organic layers were washed with brine (20 mL), dried over anhydrous Na₂SO₄, filtered and concentrated in vacuo to give the residue, which was purified by preparative TLC (CH₂Cl₂:

MeOH=10:1) to afford compound 17 (30 mg, 38% yield) as a white solid. $^1$H NMR (DMSO-d$_6$, 400 MHz): δ 7.94 (s, 1H), 7.51-7.36 (m, 2H), 7.20 and 7.15 (two s, 1H), 7.11-7.02 (m, 1H), 5.64-5.62 and 5.56-5.50 (two m, 1H), 4.99, 4.92 and 4.56 (three d, J=6.0 Hz, 1H), 4.53-4.42 (m, 1H), 3.59-3.53 (m, 1H), 3.06-2.96 (m, 1H), 2.36-2.30 (m, 1H), 2.04-1.95 (m, 1H), 1.86-1.70 (m, 5H), 1.65-1.30 (m, 6H), 1.27-1.20 (m, 1H), 1.18-1.08 (m, 1H); MS 369.2 [M+H]$^+$.

EXAMPLE 18

Preparation of (1s,3R,5S,7s)-4-(2-(6-fluoro-5H-imidazo[5,1-a]isoindol-5-yl)-1-hydroxyethyl)adamantan-1-ol (Compound 18k-1, 18k-2)

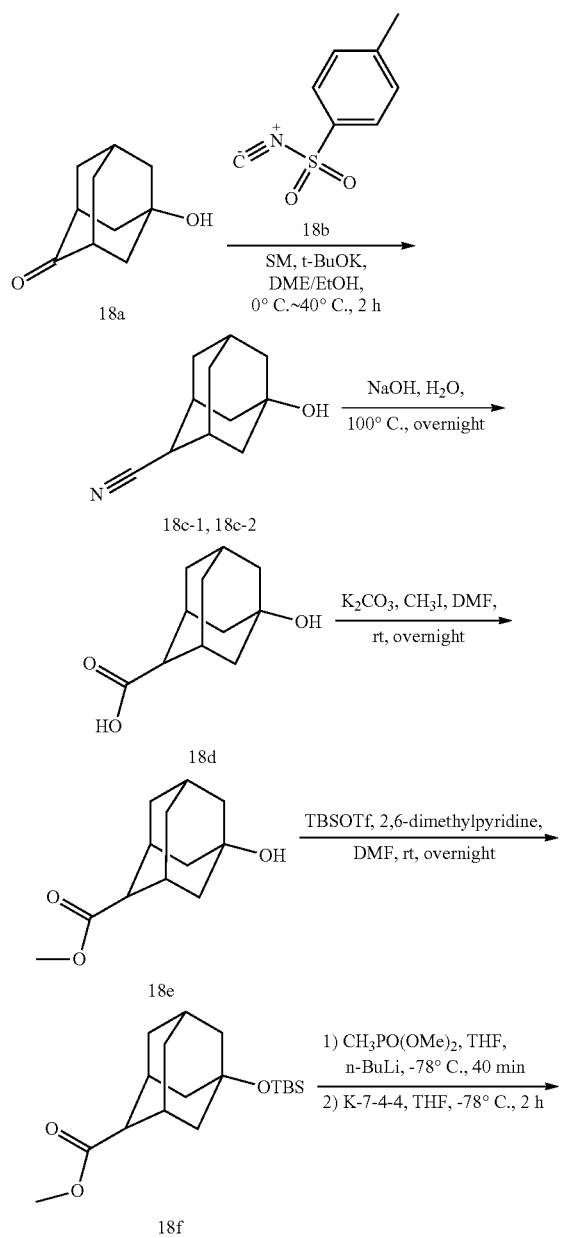

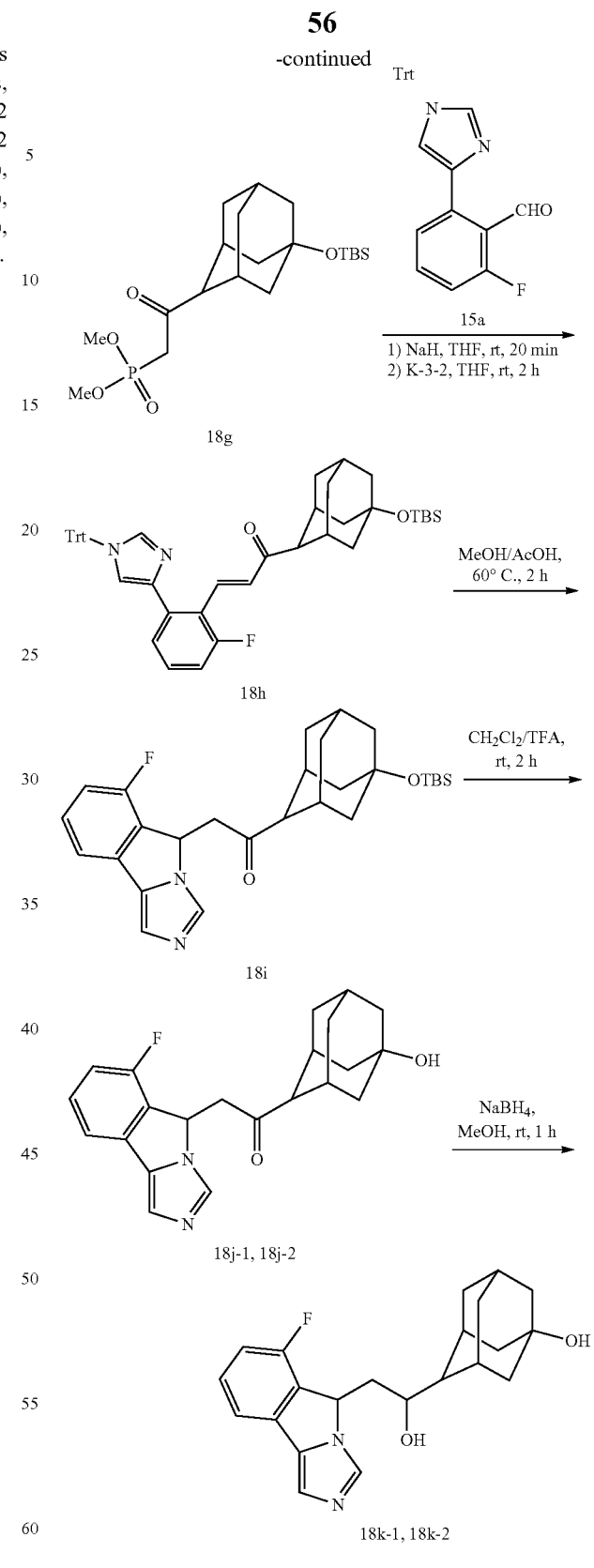

To a mixture of compound 18a (2.5 g, 15.04 mmol) and tosylmethyl isocyanide (3.8 g, 19.46 mmol) in DME/EtOH (125 mL/4 mL) was added t-BuOK (4.2 g, 37.43 mmol) portionwise, maintaining the temperature below 10° C. The mixture was stirred at room temperature for 30 min and then at 40° C. for 2 h. The reaction mixture was filtered, and the filtrate was concentrated in vacuo to give the residue, which was purified by flash column chromatography (petroleum ether/EtOAc=3/1) to afford compound 18c-1 (1.1 g, 41% yield) as a gray solid and compound 18c-2 (970 mg, 36% yield) as a gray solid. Compound 18c-1: $^1$H NMR (DMSO-$d_6$, 400 MHz): δ 4.63 (s, 1H), 3.02-2.98 (m, 1H), 2.29-2.23 (m, 2H), 2.05-1.99 (m, 1H), 1.87-1.81 (m, 2H), 1.59-1.50 (m, 8H). Compound 18c-2: $^1$H NMR (400 MHz, DMSO-$d_6$): δ 4.57 (s, 1H), 3.04-2.99 (m, 1H), 2.27-2.20 (m, 2H), 2.11-2.07 (m, 1H), 1.83-1.75 (m, 2H), 1.65-1.55 (m, 6H), 1.55-1.49 (m, 2H).

To a solution of compound 18c-1 (1.1 g, 6.21 mmol) in water (22 mL) was added NaOH (992 mg, 24.80 mmol). Then the mixture was stirred at 100° C. overnight. The mixture was cooled to room temperature and acidified with 3 N aqueous HCl until pH=3. The mixture was extracted with EtOAc (20 mL×4). The combined organic layers were concentrated in vacuo to afford crude compound 18d (1.0 g, 82% yield) as a yellow solid, which was used for the next step without further purification.

To a mixture of compound 18d (1.0 g, 5.10 mmol) and $K_2CO_3$ (1.1 g, 7.96 mmol) in DMF (15 mL) was added iodomethane (1.1 g, 7.75 mmol) dropwise over 5 min. Then the mixture was stirred at room temperature overnight. The mixture was quenched with water and extracted with EtOAc (30 mL×3). The combined organic layers were washed with brine, dried over $Na_2SO_4$, filtered and concentrated to afford crude compound 18e (700 mg, 65% yield) as a yellow solid, which was used for the next step without further purification. $^1$H NMR (DMSO-$d_6$, 400 MHz): δ 4.44, 4.38 (2 s, 1H), 3.61 (s, 3H), 2.59-2.32 (m, 3H), 2.07-1.93 (m, 1H), 1.63-1.45 (m, 8H), 1.43-1.34 (m, 2H).

To a mixture of compound 18e (700 mg, 3.33 mmol) and 2,6-dimethylpyridine (1.1 g, 10.27 mmol) in DMF (15 mL) was added trifluoromethanesulfonic acid tert-butyldimethylsilyl ester (2.6 g, 9.84 mmol) dropwise. Then the mixture was stirred at room temperature overnight. The mixture was quenched with water and extracted with EtOAc (20 mL×3). The combined organic layers were washed with brine, dried over anhydrous $Na_2SO_4$, filtered and concentrated to give the residue, which was purified by flash column chromatography (petroleum ether/EtOAc=60/1) to afford compound 18f (1.0 g, 93% yield) as a yellow oil. $^1$H NMR (DMSO-$d_6$, 400 MHz): δ 3.62 (s, 3H), 2.63-2.50 (m, 1H), 2.46-2.36 (m, 2H), 2.10-1.98 (m, 1H), 1.77-1.51 (m, 9H), 1.44-1.39 (m, 1H), 0.83, 0.81 (two s, 9H), 0.08, 0.05 (two s, 6H).

To a solution of dimethyl methylphosphonate (305 mg, 2.46 mmol) in THF (5 mL) was added n-BuLi (2.5 M in hexane, 1.23 mL, 3.08 mmol) dropwise at −78° C., then the mixture was stirred at −78° C. for 40 min. To the resulting mixture was added a solution of compound 18f (400 mg, 1.23 mmol) in THF (1 mL) at −78° C. Then the mixture was stirred at −78° C. for 2 h. The reaction mixture was quenched with aqueous $NH_4Cl$ solution and extracted with EtOAc (20 mL×3). The combined organic layers were washed with brine (20 mL), dried over anhydrous $Na_2SO_4$, filtered and concentrated in vacuo to afford crude compound 18g (400 mg, 78% yield) as yellow oil, which was used to the next step without further purification. $^1$H NMR (DMSO-$d_6$, 400 MHz): δ 3.66, 3.62 (two s, 6H), 3.40-3.29 (m, 2H), 2.69-2.63, 2.57-2.55 (two m, 1H), 2.50-2.42 (m, 2H), 2.10-1.97 (m, 1H), 1.76-1.50 (m, 9H), 1.47-1.41 (m, 1H), 0.83, 0.82 (two s, 9H), 0.08, 0.05 (two s, 6H).

To a solution of compound 18g (300 mg, 0.72 mmol) in THF (6 mL) was added NaH (60% in mineral oil, 60 mg, 1.50 mmol) at 0° C. Then the mixture was stirred at room temperature for 20 min. To the resulting mixture was added compound 15a (311 mg, 0.72 mmol) slowly over 5 min, not allowing the temperature of the mixture to rise above 5° C. Then the mixture was stirred at room temperature for 2 h. The mixture was quenched with iced aqueous $NH_4Cl$ solution (10 mL) and extracted with EtOAc (25 mL×3). The combined organic layers were washed with brine (20 mL), dried over anhydrous $Na_2SO_4$, filtered and concentrated in vacuo to afford crude compound 18h as a yellow solid, which was used to the next step without further purification.

A solution of crude compound 18h in MeOH/AcOH (12 mL/3 mL) was stirred at 60° C. for 2 h. The solvent was removed under reduced pressure. The residue was diluted with aqueous $Na_2CO_3$ solution (10 mL) and extracted with EtOAc (25 mL×3). The combined organic layers were washed with brine (20 mL), dried over anhydrous $Na_2SO_4$, filtered and concentrated in vacuo to give the residue, which was purified by flash column chromatography (petroleum ether/EtOAc=6/1) to afford compound 18i (190 mg, 55% yield for two steps) as a yellow solid. MS 481.3 [M+H]$^+$.

A mixture of compound 18i (190 mg, 0.40 mmol) in $CH_2Cl_2$/TFA (4 mL/1 mL) was stirred at room temperature for 2 h. The solvent was removed under reduced pressure. The residue was diluted with aqueous $Na_2CO_3$ solution (20 mL) and extracted with EtOAc (20 mL×3). The combined organic layers were washed with brine (20 mL), dried over anhydrous $Na_2SO_4$, filtered and concentrated in vacuo to give compound 18j (140 mg, yield 95.5%). 80 mg of 18j was purified by Preparative HPLC to afford two regioisomers compound 18j-1 (10 mg) as a yellow solid and compound 18j-2 (12 mg) as a yellow solid. Compound 18j-1: $^1$H NMR ($CDCl_3$, 400 MHz): δ 7.74 (s, 1H), 7.42-7.31 (m, 2H), 7.23 (s, 1H), 6.96 (dd, J=8.8 Hz, 8.4 Hz, 1H), 5.81 (d, J=9.6 Hz, 1H), 3.52 (dd, J=18.4 Hz, 1.6 Hz, 1H), 2.83(dd, J=18.4 Hz, 10.4 Hz, 1H), 2.63-2.51 (m, 3H), 2.19-2.14 (m, 1H), 1.85-1.41 (m, 10H); MS 367.2 [M+H]$^+$. Compound 18j-2: $^1$H NMR ($CDCl_3$, 400 MHz): δ 7.70 (s, 1H), 7.41-7.31 (m, 2H), 7.21 (s, 1H), 6.95 (dd, J=8.8 Hz, 8.4 Hz, 1H), 5.80 (d, J=9.6 Hz, 1H), 3.49 (dd, J=18.4 Hz, 2.0 Hz, 1H), 2.81 (dd, J=18.4 Hz, 10.4 Hz, 1H), 2.67-2.58 (m, 2H), 2.44 (s, 1H), 2.23-2.17 (m, 1H), 1.87-1.44 (m, 10H); MS 367.3 [M+H]$^+$.

To a solution of compound 18j-1 (10 mg, 0.027 mmol) in MeOH (0.5 mL) was added $NaBH_4$ (6 mg, 0.159 mmol) at 0° C. Then the mixture was stirred at room temperature for 1 h. The mixture was quenched with aqueous $NH_4Cl$ solution (5 mL) and extracted with EtOAc (3 mL×3). The combined organic layers were washed with brine (5 mL), dried over anhydrous $Na_2SO_4$, filtered and concentrated in vacuo to give the residue, which was purified by Preparative TLC ($CH_2Cl_2$/MeOH=10/1) to afford compound 18k-1 (6 mg, 60% yield) as a white solid. $^1$H NMR (a mixture of diastereomers, DMSO-$d_6$, 400 MHz): δ 7.99, 7.94 (two s, 1H), 7.50-7.38 (m, 2H), 7.20, 7.16 (two s, 1H), 7.14-7.04 (m, 2H), 5.74-5.66, 5.64-5.57 (two m, 1H), 5.06, 4.65 (two d, J=7.2 Hz, 1H), 4.30, 4.29 (two s, 1H), 4.03-3.93, 3.81-3.70 (two m, 1H), 2.43-2.10 (m, 2H), 1.99-1.91 (m, 1H), 1.89-1.15 (m, 13H); MS 369.2 [M+H]$^+$.

To a solution of compound 18j-2 (12 mg, 0.033 mmol) in MeOH (0.5 mL) was added $NaBH_4$ (7 mg, 0.185 mmol) at 0° C. Then the mixture was stirred at room temperature for 1 h. The mixture was quenched with aqueous $NH_4Cl$ solution (5 mL) and extracted with EtOAc (3 mL×3). The combined organic layers were washed with brine (5 mL), dried over anhydrous $Na_2SO_4$, filtered and concentrated in vacuo to give the residue, which was purified by Preparative TLC ($CH_2Cl_2$/MeOH=10/1) to afford compound 18k-2 (8 mg, 66% yield) as a white solid. $^1$H NMR (a mixture of diastereomers, DMSO-$d_6$, 400 MHz): δ 7.94 (s, 1H), 7.48-7.37 (m, 2H), 7.22,7.16 (two s, 1H), 7.13-7.05 (m, 1H), 5.73-5.67, 5.63-5.57 (two m, 1H), 5.13, 4.67 (two d, J=7.2 Hz, 1H), 4.30, 4.33 (two s, 1H), 3.99-3.90, 3.79-3.69 (two m, 1H), 2.45-2.30 (m, 2H), 2.03-1.96 (m, 1H), 1.91-1.16 (m, 13H); MS 369.2 $[M+H]^+$.

EXAMPLE 19

Biology Assays

1. IDO1 Enzyme Assay:

In vitro IDO1 enzymatic activity was determined in a mixture of 50 mM MES buffer at pH 6.5; 200 nM human IDO enzyme, 150 μM L-Tryptophan, 2250 units/mL Catalase, 20 mM ascorbic Acid and 10 μM Methylene Blue. The compounds were initially prepared in DMSO at 10 mM, then diluted in MES buffer to desired concentration. 25 μL compounds were added to 96 well plate, followed by addition of 25 μL 33.68 ng/μL IDO1 in each well. The mixture was centrifuged for 1 minute, then pre-incubated at room temperature for 30 minutes. The reaction was started by the addition of 50 μL mixture of 300 μM L-Tryptophan, 4500 units/mL catalase and 20 μM methylene blue in 50 mM pH6.5 MES buffer, and 40 mM ascorbic Acid in 0.405M pH 8.0 Tris HCl buffer. The resulting reaction mixture was incubated at 25° C. for 40 minutes. The reaction was terminated by adding 50 ul of 30% (w/v) trichloroacetic acid. The sample was further incubated for 30 min at 60° C. and centrifuged at 2000 rpm for 5 min to remove precipitated protein. The supernatant was used to mix with an equal volume of Ehrlich's reagent (2% w/v p-dimethylaminobenzaldehyde in glacial acetic acid), then mixture was incubated at room temperature for 10 minutes. OD value was read at 490 nm in a spectrophotometer. Inhibition rate of the compound are calculated according to the formula below:

% inhibition=100−100×(sample signal−low control)/(high control−low control)

wherein High control=no compound; Low control=no enzyme and no compound.
$IC_{50}$ values were calculated by fitting the doseresponse curves with Xlfit excel add-in version 4.3.1. The results are listed in Table 1 below.

TABLE 1

| Compound | IDO1 ($IC_{50}$, nM) | IDO1 (inhibition % at 500 nM) |
|---|---|---|
| 1 | | >50 |
| 6 | | >50 |
| 7 | | >50 |
| 8 | | >50 |
| 9 | <500 | |
| 10 | <500 | |
| 14f | <100 | |
| 15d | <100 | |
| 15d-1 | >500 | |
| 15d-2 | >500 | |
| 15d-3 | <100 | |
| 15d-4 | >500 | |
| 15e | <100 | |
| 16 | <100 | |
| 17 | <100 | |
| 18k-1 | <500 | |
| 18k-2 | <100 | |

2. TDO Enzyme Assay:

In vitro TDO enzymatic activity was determined in a mixture of 50 mM potassium phosphate buffer, pH 6.5; 200 nM human TDO enzyme, 300 μM L-Tryptophan, 0.2 mg/mL Catalase, 20 mM ascorbic Acid and 20 μM Methylene Blue. 100× compounds were prepared in DMSO from 1 mM, then diluted three fold, 8 doses in total. 2 μL compounds were added to 96 well plate, followed by addition of 100 μL 400 nM TDO and 0.4 mg/ml catalase in each well. The mixture was centrifuged for 1 minute, then pre-incubated at room temperature for 10 minutes. The reaction was started by the addition of 100 μL mixture of 600 μM L-Tryptophan, 40 μM methylene blue and 40 mM ascorbic acid in 50 mM potassium phosphate buffer, pH 6.5. The resulting reaction mixture was shaken 30 secs and Kineticly read the plate in SpectraMax 384 at OD321 nm for 20 mins at RT. Copy slope data from Synergy program, and convert slope values to inhibition values. Percent inhibition=(max−conversion)/(max−min)*100. "max" stands for high control; "min" stands for low control. Fit the data in GraphPad Prism5.0 to obtain IC50 values. Equation used is:

$Y$=Bottom+(Top−Bottom)/(1+10^((Log $IC50$−$X$)*HillSlope).

TABLE 2

| Compound | TDO ($IC_{50}$, nM) | TDO (inhibition % at 1000 nM) |
|---|---|---|
| 3 | | >50 |
| 6 | | >50 |
| 8 | | >50 |
| 9 | <200 | |
| 10 | | >50 |
| 13 | | >50 |
| 14f | <200 | |
| 15d | <200 | |
| 15e | <500 | |
| 16 | <200 | |
| 17 | <200 | |

Other Embodiments of the Invention

The invention has been described above with the reference to specific examples and embodiments, not to be construed as limiting the scope of this invention in any way. It is understood that various modifications and additions can be made to the specific examples and embodiments disclosed without departing from the spirit of the invention, and such modifications and additions are contemplated as being part of the present invention.

What is claimed is:

1. A compound of Formula (I), or a pharmaceutically acceptable salt or solvate thereof:

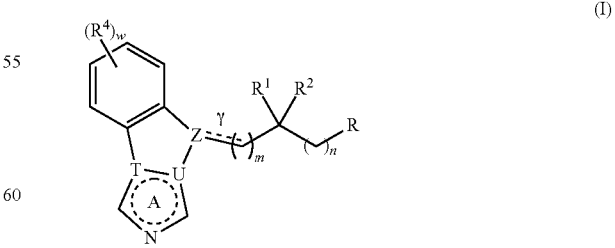

in Formula (I):
Ring A is a 5-membered aromatic ring, wherein T is C and U is N;
Z is $CR^3$ and bond γ is a single bond;

each of $R^1$ and $R^2$ independently is hydrogen, halogen, $C_{1-4}$ alkyl, $C_{2-4}$ alkenyl, $C_{2-4}$ alkynyl, cycloalkyl, $C_{1-4}$ haloalkyl, heterocyclyl, CN, $OR^5$, or $N(R^5)_2$;

or, $R^1$ and $R^2$ together with the carbon atom to which they are attached, form a 3- to 8-membered ring that contains 0-2 heteroatoms each independently being N, O, or S;

w is 0, 1, 2, 3, or 4;

each of m and n is 0;

$R^3$ is hydrogen, fluorine, or $C_{1-4}$ alkyl;

$R^4$ at each occurrence is independently hydrogen, halogen, $C_{1-4}$ alkyl, $C_{2-4}$ alkenyl, $C_{2-4}$ alkynyl, cycloalkyl, $C_{1-4}$ haloalkyl, heterocyclyl, aryl, heteroaryl, CN, $NO_2$, $OR^5$, $N(R^5)_2$, $SR^5$, $C(O)OR^5$, $C(O)N(R^5)_2$, $C(O)R^5$, $S(O)_2R^5$, $S(O)_2N(R^5)_2$, $OC(O)R^5$, $OC(O)OR^5$, $OC(O)N(R^5)_2$, $N(R^5)C(O)R^5$, or $N(R^5)C(O)N(R^5)_2$;

$R^5$ at each occurrence is independently hydrogen, $C_{1-4}$ alkyl, cycloalkyl, heterocyclyl, aryl, or heteroaryl;

R is $C(OR^B)(R^A)(R^C)$, wherein $R^A$ is a bridged bicyclic $C_7$-$C_{16}$ cycloalkyl, aryl-heterocyclyl, heteroaryl-heterocyclyl, cycloalkyl-heterocyclyl, heterocyclyl-heterocyclyl, or heterocyclyl-aryl;

wherein, the bridge bicyclic $C_7$-$C_{16}$ cycloalkyl, aryl-heterocyclyl, heteroaryl-heterocyclyl, cycloalkyl-heterocyclyl, heterocyclyl-heterocyclyl, or heterocyclyl-aryl are each optionally substituted by one or two $=R^{42}$ groups and each optionally substituted by one to three $R^{41}$ groups;

wherein each $R^{41}$ is independently hydrogen, halogen, $C_{1-4}$ alkyl, $C_{2-4}$ alkenyl, $C_{2-4}$ alkynyl, $C_{1-4}$ haloalkyl, aryl, heteroaryl, cycloalkyl, heterocyclyl, CN, $NO_2$, N-oxide, $OR^5$, $N(R^5)_2$, $SR^5$, $C(O)OR^5$, $C(O)N(R^5)_2$, $C(O)N(OH)R^5$, $C(O)R^5$, $S(O)_2R^5$, $S(O)_2N(R^5)_2$, $OC(O)R^5$, $N(R^5)C(O)R^5$, or $N(R^5)C(O)N(R^5)_2$;

$=R^{42}$ is $=O$;

$R^B$ is hydrogen, $CH_2$—$OP(O)_2(OR^5)_2$, or $P(O)(OR^4)_2$;

$R^C$ is hydrogen or $C_{1-4}$ alkyl; and each of alkyl, alkenyl, alkynyl, cycloalkyl, heterocyclyl, aryl, and heteroaryl described above is optionally substituted with one to three substituents independently selected from the group consisting of halogen, $C_{1-4}$ alkyl, $C_{2-4}$ alkenyl, $C_{2-4}$ alkynyl, cycloalkyl, heterocyclyl, aryl, heteroaryl, CN, $NO_2$, $OR^5$, $SR^5$, $N(R^5)_2$, $C(O)R^5$, $C(O)OR^5$, $C(O)N(R^5)_2$, and $S(O)_2R^5$.

2. The compound of claim 1, wherein Z is CH.

3. The compound of claim 1, wherein Formula (II)

(II)

wherein:

each $R^4$ is independently hydrogen, halogen, $C_{1-4}$ alkyl, $C_{1-4}$ haloalkyl, CN, $NO_2$, $OR^5$, $N(R^5)_2$, or $SR^5$;

w is 0, 1, or 2;

"〜〜〜" indicates the point of attachment in Formula (II) to the rest of the molecule in Formula (I); and "*" denotes a chiral center.

4. The compound of claim 1, wherein $R^1$ and $R^2$, together with the carbon atom to which they are attached form a $C_{3-6}$ cycloalkyl.

5. The compound of claim 1, wherein both $R^1$ and $R^2$ are H or F.

6. The compound of claim 1, wherein R is $C(OH)(R^A)(R^C)$.

7. The compound of claim 1, wherein $R^A$ is $C_{6-10}$ aryl-(5-8-membered heterocyclyl), $C_{3-6}$ cycloalkyl-(5-8-membered heterocyclyl), (5-8-membered heterocyclyl)-(5-8-membered heterocyclyl), or (5-8-membered heterocyclyl)-$C_{6-10}$ aryl, wherein the two moieties in aryl-heterocyclyl, cycloalkyl-heterocyclyl, heterocyclyl-heterocyclyl, and heterocyclyl-aryl are linked through an N—C bond.

8. The compound of claim 1, wherein $R^A$ is bridged $C_7$-$C_{16}$ cycloalkyl, and the cycloalkyl is a carbocyclic bicyclic ring.

9. The compound of claim 8, wherein $R^A$ is unsubstituted or substituted bicyclo[2.2.2]octyl.

10. The compound of claim 9, wherein the term "substituted" means having 1 to 3 substituents selected from the group consisting of halogen, $C_{1-4}$ alkyl, —OH, $C_{1-4}$ alkyloxy, $C_{1-4}$ haloalkyl, $C_{3-6}$ cycloalkyl, CN, $N(C_{1-4}$ alkyl)$_2$, $C(O)OC_{1-4}$ alkyl, $C(O)N(C_{1-4}$ alkyl)$_2$, and $C(O)C_{1-4}$ alkyl.

11. The compound of claim 1, wherein each $R^{41}$ is independently hydrogen, halogen, $C_{1-4}$ alkyl, $C_{1-4}$ haloalkyl, $C_{3-6}$ cycloalkyl, CN, $NO_2$, $OR^5$, $N(R^5)_2$, $C(O)OR^5$, $C(O)N(R^5)_2$, $C(O)N(OH)R^5$, or $C(O)R^5$; and/or each $=R^{42}$ is $=O$.

12. The compound of claim 1, wherein $C(OR^B)(R^A)(R^C)$ is and $R^{41}$ is independently hydrogen, halogen, $C_{1-4}$ alkyl, $C_{1-4}$ haloalkyl, $C_{3-6}$ cycloalkyl, CN, $NO_2$, $OR^5$, $N(R^5)_2$, $C(O)OR^5$, $C(O)N(R^5)_2$, $C(O)N(OH)R^5$, or $C(O)R^5$.

13. The compound of claim 12, wherein $C(OR^B)(R^A)(R^C)$ is:

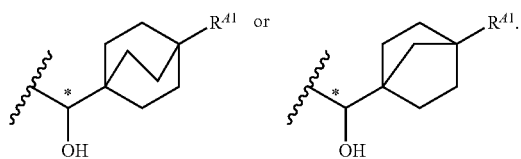

14. The compound of claim 1, or a pharmaceutically acceptable salt or solvate thereof, characterized by formula (IV):

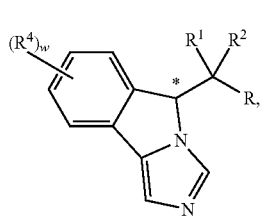

wherein R is $C(OR^B)(R^A)(R^C)$ having a structure selected from the group consisting of:

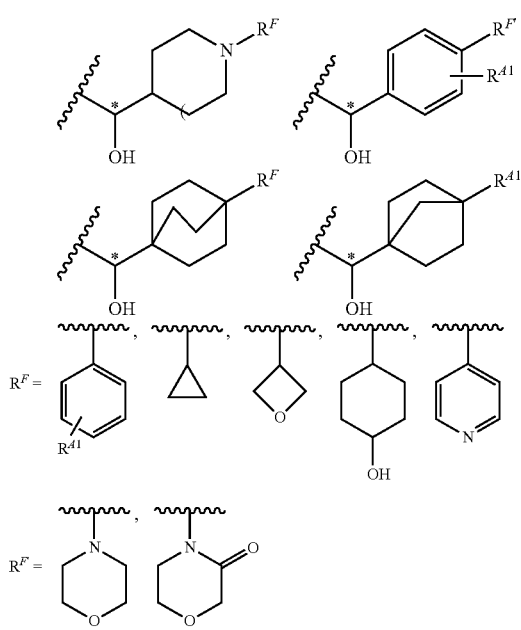

and $R^1$ and $R^2$ are each independently hydrogen or halogen;
w is 0, 1, 2, or 3;
$R^4$ at each occurrence is independently hydrogen, halogen, $C_{1-4}$ alkyl, $C_{1-4}$ haloalkyl, CN, $NO_2$, $OR^5$, $N(R^5)_2$, or $SR^5$;
$R^5$ at each occurrence is independently hydrogen or $C_{1-4}$ alkyl; and
$R^{A1}$ is independently hydrogen, halogen, $C_{1-4}$ alkyl, $C_{1-4}$ haloalkyl, $C_{3-6}$ cycloalkyl, CN, $NO_2$, $OR^5$, $N(R^5)_2$, $C(O)OR^5$, $C(O)N(R^5)_2$, $C(O)N(OH)R^5$, or $C(O)R^5$.

15. The compound of claim 14, wherein $C(OR^B)(R^A)(R^C)$ is:

16. The compound of claim 15, or a pharmaceutically acceptable salt or solvate thereof, characterized by formula (V):

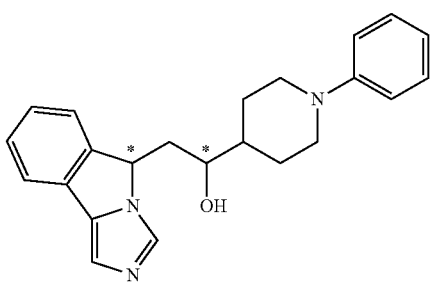

wherein:
$R^1$ and $R^2$ are each independently hydrogen or halogen;
w is 0, 1, 2, or 3;
$R^4$ at each occurrence is independently hydrogen, halogen, $C_{1-4}$ alkyl, $C_{1-4}$ haloalkyl, CN, $NO_2$, $OR^5$, $N(R^5)_2$, or $SR^5$; and
$R^{A1}$ is independently hydrogen, halogen, $C_{1-4}$ alkyl, $C_{1-4}$ haloalkyl, $C_{3-6}$ cycloalkyl, CN, $NO_2$, $OR^5$, $N(R^5)_2$, $C(O)OR^5$, $C(O)N(R^5)_2$, $C(O)N(OH)R^5$, or $C(O)R^5$.

17. The compound of claim 16, wherein
w is 0, 1, or 2;
$R^4$ is hydrogen or halogen;
$R^1$ and $R^2$ are each hydrogen;
and
$R^{A1}$ is halogen or OH.

18. The compound of claim 1, wherein the compound of Formula (I) is a compound selected from the group consisting of:

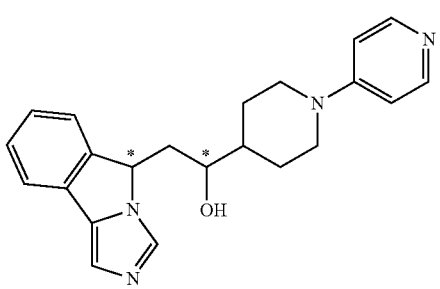

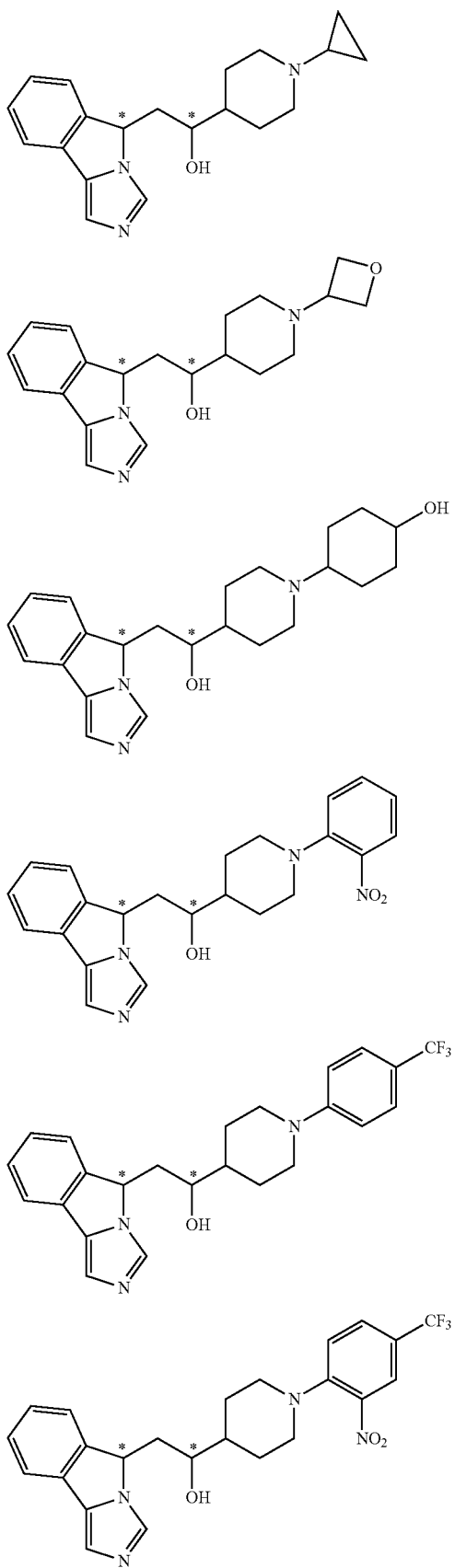
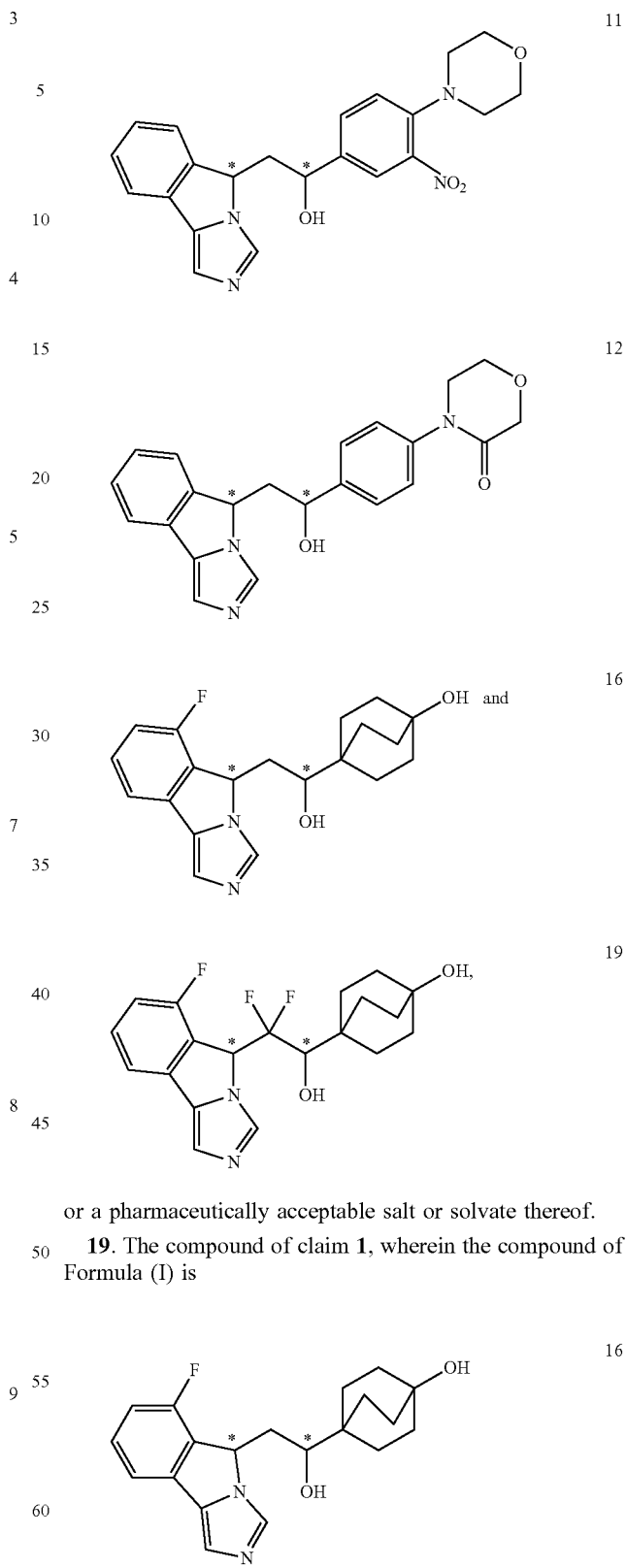
or a pharmaceutically acceptable salt or solvate thereof.
19. The compound of claim 1, wherein the compound of Formula (I) is
or its enantiomeric compounds.
20. The compound of claim 1, wherein the compound of Formula (I) is:

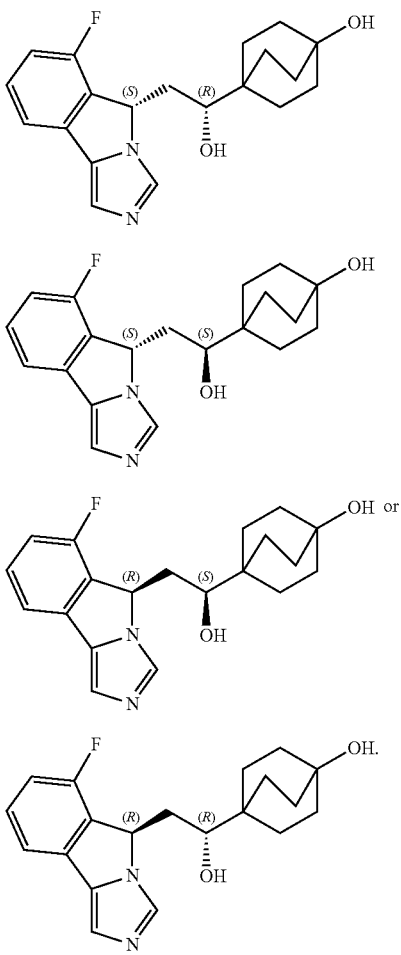

21. A method for preparing a pharmaceutical composition, comprising mixing the compound according to claim 1, or a pharmaceutically acceptable salt, or a solvate thereof and a pharmaceutically acceptable carrier to form a pharmaceutical composition.

22. A pharmaceutical composition, comprising a compound according to claim 1, or a pharmaceutically acceptable salt or a solvate thereof, and a pharmaceutically acceptable carrier or excipient.

23. A method for treating a disease or disorder mediated by IDO and/or TDO in a subject, comprising administering to the subject in need thereof a therapeutically effective amount of a compound according to claim 1, or a pharmaceutically acceptable salt, solvate, or composition thereof, wherein the disease or disorder mediated by IDO and/or TDO is selected from the group consisting of depression, amyotrophic lateral sclerosis, Huntington's disease, Alzheimer's disease, Parkinson's disease, cataracts, and multiple sclerosis.

24. The compound according to claim 1, wherein $R^4$ is bridged $C_8$-$C_{12}$ cycloalkyl, wherein the cycloalkyl is a carbocyclic bicyclic ring.

25. A pharmaceutical composition, comprising a compound according to claim 18, or a pharmaceutically acceptable salt or a solvate thereof, and a pharmaceutically acceptable carrier or excipient.

26. A method for treating a disease or disorder mediated by IDO and/or TDO in a subject, comprising administering to the subject in need thereof a therapeutically effective amount of a compound according to claim 18, or a pharmaceutically acceptable salt, solvate, or composition thereof, wherein the disease or disorder mediated by IDO and/or TDO is selected from the group consisting of depression, amyotrophic lateral sclerosis, Huntington's disease, Alzheimer's disease, Parkinson's disease, cataracts, and multiple sclerosis.

* * * * *